(12) United States Patent
Rajagopalan et al.

(10) Patent No.: US 12,721,954 B2
(45) Date of Patent: Sep. 1, 2026

(54) SYSTEM FOR TREATING A PATIENT

(71) Applicant: Fractyl Health, Inc., Lexington, MA (US)

(72) Inventors: Harith Rajagopalan, Wellesley Hills, MA (US); Jay Caplan, Boston, MA (US); Jason West, Boston, MA (US); Jacob Wainer, Brighton, MA (US); Michael Biasella, Medford, MA (US); J. Christopher Flaherty, Nottingham, NH (US)

(73) Assignee: Fractyl Health, Inc., Burlington, MA (US)

( * ) Notice: Subject to any disclaimer, the term of this patent is extended or adjusted under 35 U.S.C. 154(b) by 471 days.

(21) Appl. No.: 18/366,898

(22) Filed: Aug. 8, 2023

(65) Prior Publication Data

US 2023/0381425 A1 Nov. 30, 2023

Related U.S. Application Data

(63) Continuation of application No. PCT/US2022/016200, filed on Feb. 11, 2022.

(Continued)

(51) Int. Cl.
*A61M 5/32* (2006.01)
*A61K 9/00* (2006.01)

(Continued)

(52) U.S. Cl.
CPC ......... *A61M 5/3291* (2013.01); *A61K 9/0019* (2013.01); *A61M 25/02* (2013.01);

(Continued)

(58) Field of Classification Search
CPC ................ A61M 5/3291; A61M 25/02; A61M 2005/1787; A61M 2025/022;

(Continued)

(56) References Cited

U.S. PATENT DOCUMENTS 4,609,371 A 9/1986 Pizzino
5,084,044 A 1/1992 Quint (Continued)

FOREIGN PATENT DOCUMENTS

CA 2666661 C 1/2015
CN 1771888 A 5/2006

(Continued)

OTHER PUBLICATIONS

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.

(Continued)

*Primary Examiner* — Lauren P Farrar

(74) *Attorney, Agent, or Firm* — Wolf, Greenfield & Sacks, P.C.

(57) ABSTRACT

Provided herein are methods for providing a therapeutic benefit to a patient. A method of treating a patient with a metabolic disease and/or a pancreatic disease includes: selecting a patient with a metabolic disease and/or a pancreatic disease; selecting one or more pancreatic deposit sites; advancing a depositing device comprising a at least one depositing element to the selected one or more pancreatic deposit sites; and delivering a treatment agent through the at least one depositing element into the selected one or more pancreatic deposit sites. Systems and devices are also described.

13 Claims, 26 Drawing Sheets

Related U.S. Application Data

(60) Provisional application No. 63/280,383, filed on Nov. 17, 2021, provisional application No. 63/214,160, filed on Jun. 23, 2021, provisional application No. 63/148,551, filed on Feb. 11, 2021.

(51) Int. Cl.
*A61M 5/178* (2006.01)
*A61M 25/02* (2006.01)

(52) U.S. Cl.
CPC .............. *A61M 2005/1787* (2013.01); *A61M 2025/022* (2013.01)

(58) Field of Classification Search
CPC .. A61M 5/1452; A61M 5/14526; A61M 5/19; A61M 5/2053; A61M 5/3148; A61M 5/3286; A61M 5/3298; A61K 9/0019; A61K 38/00; A61B 17/3478
See application file for complete search history.

(56) References Cited

U.S. PATENT DOCUMENTS 5,190,540 A 3/1993 Lee, I
5,423,754 A 6/1995 Cornelius et al.
5,471,982 A 12/1995 Edwards et al.
5,496,311 A 3/1996 Abele et al.
5,515,100 A 5/1996 Nogo
5,542,928 A 8/1996 Evans et al.
5,549,559 A 8/1996 Eshel
5,575,772 A 11/1996 Lennox
5,704,934 A 1/1998 Neuwirth et al.
5,730,719 A 3/1998 Edwards
5,800,484 A 9/1998 Gough et al.
5,827,269 A 10/1998 Saadat
5,859,037 A 1/1999 Whitcomb et al.
5,869,037 A 2/1999 Crystal et al.
5,871,525 A 2/1999 Edwards et al.
5,879,347 A 3/1999 Saadat et al.
5,957,962 A 9/1999 Wallsten, I et al.
5,964,753 A 10/1999 Edwards
6,009,877 A 1/2000 Edwards
6,053,937 A 4/2000 Edwards et al.
6,056,744 A 5/2000 Edwards et al.
6,066,132 A 5/2000 Chen et al.
6,077,257 A 6/2000 Edwards et al.
6,112,123 A 8/2000 Kelleher et al.
6,293,909 B1 9/2001 Chu et al.
6,325,777 B1 12/2001 Zadno-Azizi et al.
6,325,798 B1 12/2001 Edwards et al.
6,338,726 B1 1/2002 Edwards et al.
6,358,245 B1 3/2002 Edwards et al.
6,402,744 B2 6/2002 Edwards et al.
6,405,732 B1 6/2002 Edwards et al.
6,409,723 B1 6/2002 Edwards
6,425,887 B1 7/2002 Mcguckin et al.
6,443,947 B1 9/2002 Marko et al.
6,544,226 B1 4/2003 Gaiser et al.
6,673,070 B2 1/2004 Edwards et al.
6,712,814 B2 3/2004 Edwards et al.
6,802,841 B2 10/2004 Utley et al.
6,905,496 B1 6/2005 Ellman et al.
6,962,587 B2 11/2005 Johnson et al.
6,974,456 B2 12/2005 Edwards et al.
7,077,841 B2 7/2006 Gaiser et al.
7,111,627 B2 9/2006 Stack et al.
7,122,031 B2 10/2006 Edwards et al.
7,125,407 B2 10/2006 Edwards et al.
7,156,860 B2 1/2007 Wallsten
7,165,551 B2 1/2007 Edwards et al.
7,241,295 B2 7/2007 Maguire
7,326,207 B2 2/2008 Edwards
7,371,215 B2 5/2008 Colliou et al.
7,387,626 B2 6/2008 Edwards et al.
7,422,587 B2 9/2008 Bek et al.
7,507,234 B2 3/2009 Utley et al.
7,507,238 B2 3/2009 Edwards et al.
7,530,979 B2 5/2009 Ganz et al.
7,556,628 B2 7/2009 Utley et al.
7,585,296 B2 9/2009 Edward et al.
7,632,268 B2 12/2009 Utley et al.
7,632,291 B2 12/2009 Stephens et al.
7,648,500 B2 1/2010 Edwards et al.
7,758,623 B2 7/2010 Dzeng et al.
7,762,977 B2 7/2010 Porter et al.
7,947,038 B2 5/2011 Edwards
7,959,627 B2 6/2011 Utley et al.
7,993,336 B2 8/2011 Jackson et al.
7,997,278 B2 8/2011 Utley et al.
8,012,149 B2 9/2011 Jackson et al.
8,066,689 B2 11/2011 Mitelberg et al.
8,152,803 B2 4/2012 Edwards et al.
8,177,853 B2 5/2012 Stack et al.
8,192,426 B2 6/2012 Stern et al.
8,251,992 B2 8/2012 Utley et al.
8,273,012 B2 9/2012 Wallace et al.
8,323,229 B2 12/2012 Shin et al.
8,364,237 B2 1/2013 Stone et al.
8,377,055 B2 2/2013 Jackson et al.
8,486,005 B2 7/2013 Yodfat et al.
8,641,711 B2 2/2014 Kelly et al.
8,740,894 B2 6/2014 Edwards
8,790,705 B2 7/2014 Geigle et al.
9,364,283 B2 6/2016 Utley et al.
9,555,020 B2 1/2017 Pasricha et al.
9,615,880 B2 4/2017 Gittard et al.
9,757,535 B2 9/2017 Rajagopalan et al.
9,844,641 B2 12/2017 Rajagopalan et al.
10,232,143 B2 3/2019 Rajagopalan et al.
10,299,857 B2 5/2019 Rajagopalan et al.
10,349,998 B2 7/2019 Levin et al.
10,610,663 B2 4/2020 Rajagopalan et al.
10,765,474 B2 9/2020 Kadamus et al.
10,864,352 B2 12/2020 Rajagopalan et al.
10,869,718 B2 12/2020 Rajagopalan et al.
10,980,590 B2 4/2021 Rajagopalan et al.
10,987,149 B2 4/2021 Rajagopalan et al.
11,878,128 B2 1/2024 Rajagopalan et al.
2002/0077594 A1 6/2002 Chien et al.
2002/0192162 A1 12/2002 Green
2003/0040804 A1 2/2003 Stack et al.
2003/0093072 A1 5/2003 Friedman
2003/0153905 A1 8/2003 Edwards et al.
2003/0233065 A1 12/2003 Steward et al.
2004/0082859 A1 4/2004 Schaer
2004/0087936 A1 5/2004 Stern et al.
2004/0133165 A1 7/2004 Duchon et al.
2004/0133256 A1 7/2004 Callister
2004/0148034 A1 7/2004 Kagan et al.
2004/0204768 A1 10/2004 Geitz
2004/0215180 A1 10/2004 Starkebaum et al.
2004/0215296 A1 10/2004 Ganz et al.
2004/0220559 A1 11/2004 Kramer et al.
2005/0048043 A1* 3/2005 Wilson .................. C12N 15/86
514/44 R
2005/0096638 A1 5/2005 Starkebaum et al.
2005/0154386 A1 7/2005 West et al.
2005/0165437 A1 7/2005 Takimoto
2005/0171524 A1 8/2005 Stern et al.
2005/0192652 A1 9/2005 Cioanta et al.
2005/0203489 A1 9/2005 Saadat et al.
2005/0222558 A1 10/2005 Baxter et al.
2005/0245943 A1 11/2005 Zvuloni et al.
2005/0251116 A1 11/2005 Steinke et al.
2005/0273090 A1 12/2005 Nieman et al.
2006/0070631 A1 4/2006 Scopton et al.
2006/0118127 A1 6/2006 Chinn
2006/0122099 A1 6/2006 Aoki
2006/0135963 A1 6/2006 Kick et al.
2006/0155261 A1 7/2006 Bek et al.
2006/0205992 A1 9/2006 Lubock et al.
2006/0247683 A1 11/2006 Danek et al.
2006/0293742 A1 12/2006 Dann et al.

(56) References Cited

U.S. PATENT DOCUMENTS

2007/0016262 A1 1/2007 Gross et al.
2007/0032788 A1 2/2007 Edwards et al.
2007/0100355 A1 5/2007 Bonde et al.
2008/0045785 A1 2/2008 Oyatsu
2008/0107744 A1 5/2008 Chu
2008/0119788 A1 5/2008 Winter
2008/0125760 A1 5/2008 Gilboa
2008/0125803 A1 5/2008 Sadamasa et al.
2008/0147056 A1 6/2008 Van Der Weide et al.
2008/0207994 A1 8/2008 Gonon
2008/0243112 A1 10/2008 De Neve
2008/0319504 A1 12/2008 Loushin et al.
2009/0012469 A1 1/2009 Nita
2009/0012518 A1 1/2009 Utley et al.
2009/0018533 A1 1/2009 Perkins et al.
2009/0048593 A1 2/2009 Ganz et al.
2009/0069805 A1 3/2009 Fischer et al.
2009/0270851 A1 10/2009 Babkin et al.
2010/0022891 A1 1/2010 Zuluaga et al.
2010/0030190 A1 2/2010 Singh
2010/0114087 A1 5/2010 Edwards et al.
2010/0114325 A1 5/2010 Yang et al.
2010/0168561 A1 7/2010 Anderson
2010/0168624 A1 7/2010 Sliwa
2010/0204673 A1 8/2010 Miller
2010/0204688 A1 8/2010 Hoey et al.
2010/0217151 A1 8/2010 Gostout et al.
2010/0256775 A1 10/2010 Belhe et al.
2010/0260703 A1 10/2010 Yankelson et al.
2011/0046537 A1 2/2011 Errico et al.
2011/0091564 A1 4/2011 Chu
2011/0106273 A1 5/2011 Belhe et al.
2011/0160648 A1 6/2011 Hoey
2011/0172659 A1 7/2011 Brannan
2011/0184401 A1 7/2011 Iwata et al.
2011/0319809 A1 12/2011 Smith
2012/0059364 A1 3/2012 Baust et al.
2012/0197245 A1 8/2012 Burnett et al.
2012/0271277 A1 10/2012 Fischell et al.
2012/0271301 A1 10/2012 Fischell et al.
2013/0071466 A1 3/2013 Chancellor et al.
2013/0178910 A1 7/2013 Azamian et al.
2014/0031773 A1 1/2014 Mikkaichi
2014/0074077 A1 3/2014 Lane
2014/0088529 A1 3/2014 Bengtson
2014/0121646 A1 5/2014 Lodin et al.
2014/0135661 A1 5/2014 Garrison et al.
2014/0163664 A1 6/2014 Goldsmith
2014/0255458 A1 9/2014 Li et al.
2014/0324037 A1 10/2014 Hoey et al.
2015/0045825 A1 2/2015 Caplan et al.
2015/0141987 A1 5/2015 Caplan et al.
2015/0148738 A1 5/2015 Caplan et al.
2015/0359594 A1 12/2015 Ben-Oren et al.
2016/0008050 A1 1/2016 Rajagopalan et al.
2016/0081745 A1* 3/2016 Rajagopalan ...... A61B 18/1492 606/41
2016/0310200 A1 10/2016 Wang
2016/0354144 A1 12/2016 Caplan et al.
2017/0007310 A1* 1/2017 Rajagopalan ........ A61B 5/0036
2017/0151416 A1 6/2017 Kutikov et al.
2017/0191035 A1 7/2017 Sia et al.
2018/0221622 A1 8/2018 Rajagopalan et al.
2020/0060758 A1 2/2020 Rajagopalan et al.
2020/0060942 A1 2/2020 Rajagopalan et al.
2020/0138505 A1 5/2020 Levin et al.
2020/0155217 A1 5/2020 Morneau et al.
2020/0261144 A1 8/2020 Caplan et al.
2020/0305972 A1 10/2020 Kadamus et al.
2020/0405388 A1 12/2020 Rajagopalan et al.
2021/0008336 A1 1/2021 Rajagopalan et al.
2021/0085390 A1 3/2021 Kadamus et al.
2021/0137995 A1 5/2021 Rajagopalan et al.
2021/0196341 A1 7/2021 Rajagopalan et al.
2021/0299404 A1 9/2021 Rajagopalan et al.
2021/0307816 A1 10/2021 Rajagopalan et al.
2022/0022932 A1 1/2022 Caplan et al.
2022/0054180 A1 2/2022 Rajagopalan et al.
2022/0071653 A1 3/2022 Mani et al.
2022/0117658 A1 4/2022 Rajagopalan et al.
2022/0265337 A1 8/2022 Rajagopalan et al.
2022/0304744 A1 9/2022 Kadamus
2022/0330998 A1 10/2022 Rajagopalan et al.
2024/0277946 A1 8/2024 Rajagopalan et al.

FOREIGN PATENT DOCUMENTS

CN 101212932 A 7/2008
EP 1698296 A1 9/2006
EP 1886634 A1 2/2008
EP 2662036 A1 11/2013
EP 3071286 A1 9/2016
JP 2002503512 A 2/2002
JP 2003520068 A 7/2003
JP 2004500184 A 1/2004
JP 2006509536 A 3/2006
JP 2006136726 A 6/2006
JP 2007502690 A 2/2007
JP 2008515464 A 5/2008
JP 2010142661 A 7/2010
JP 2010533036 A 10/2010
JP 2011517599 A 6/2011
JP 2013543423 A 12/2013
JP 2014503256 A 2/2014
KR 20080013945 A 2/2008
WO WO-9418896 A1 9/1994
WO WO-9912489 A2 3/1999
WO WO-0207628 A2 1/2002
WO WO-02058577 A1 8/2002
WO WO-02096327 A2 12/2002
WO WO-02102453 A2 12/2002
WO WO-03033045 A2 4/2003
WO WO-03092609 A2 11/2003
WO WO-2004064600 A2 8/2004
WO WO-2006020370 A2 2/2006
WO WO-2007044244 A2 4/2007
WO WO-2007067919 A2 6/2007
WO WO-2008002654 A2 1/2008
WO WO-2010042461 A1 4/2010
WO WO-2010125570 A1 11/2010
WO WO-2011060301 A1 5/2011
WO WO-2012009486 A2 1/2012
WO WO-2012099974 A2 7/2012
WO WO-2013130655 A1 9/2013
WO WO-2013134541 A2 9/2013
WO WO-2013159066 A1 10/2013
WO WO-2014022436 A1 2/2014
WO WO-2014026055 A1 2/2014
WO WO-2014055997 A1 4/2014
WO WO-2014070136 A1 5/2014
WO WO-2015038973 A1 3/2015
WO WO-2015077571 A1 5/2015
WO WO-2015148541 A1 10/2015
WO WO-2015185158 A1 12/2015
WO WO-2016011269 A1 1/2016
WO WO-2017004432 A1 1/2017
WO WO-2018089773 A1 5/2018
WO WO-2019018362 A1 1/2019
WO WO-2019136240 A1 7/2019
WO WO-2021081072 A1 4/2021
WO WO-2021146190 A1 7/2021
WO WO-2021146535 A1 7/2021
WO WO-2021188781 A1 9/2021
WO WO-2021262646 A1 12/2021
WO WO-2022174091 A1 8/2022

OTHER PUBLICATIONS

Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.

(56) References Cited

OTHER PUBLICATIONS

Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
EP12736438.8 The Extended European Search Report dated Nov. 22, 2016.
EP14844285.8 The Extended European Search Report dated Apr. 25, 2017.
EP20150391.9 The Extended European Search Report dated Aug. 20, 2020.
EP20159816.6 The Extended European Search Report dated Aug. 17, 2020.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report and search opinion dated Nov. 25, 2015 for EP Application No. 13777572.2.
European search report with written opinion dated Feb. 1, 2018 for EP Application No. 15822378.
European search report with written opinion dated Dec. 2, 2016 for EP Application No. 14807116.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 19 for U.S. Appl. No. 14/609,332.
Final Office action dated Jul. 10, 2019 for U.S. Appl. No. 15/274,948.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
Grikscheit, et al. Tissue-engineered small intestine improves recovery after massive small bowel resection. Ann Surg., 2004, 240:748-754.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
International search report and written opinion dated Oct. 23, 2015 for PCT/US2015/040775.
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
International search report with written opinion dated Jan. 9, 2018 for PCT/US2017/061074.
Miyawaki, et al. Inhibition of gastric inhibitory polypeptide signaling prevents obesity. Nat Med. Jul. 2002;8(7):738-42. Epub Jun. 17, 2002.
Notice of Allowance dated Jul. 7, 2017 for U.S. Appl. No. 15/274,764.
Notice of Allowance dated Sep. 14, 2017 for U.S. Appl. No. 15/274,809.
Office Action date Jul. 11, 2018 for U.S. Appl. No. 14/917,243.
Office Action date Aug. 9, 2018 for U.S. Appl. No. 14/673,565.
Office action dated Jan. 8, 2018 for U.S. Appl. No. 14/609,334.
Office Action dated Jan. 13, 2017 for U.S. Appl. No. 14/609,332.
Office action dated Feb. 29, 2016 for U.S. Appl. No. 14/609,334.
Office action dated Mar. 7, 19 for U.S. Appl. No. 13/945,138.
Office Action dated Mar. 7, 2017 for U.S. Appl. No. 15/274,764.
Office Action dated Mar. 7, 2017 for U.S. Appl. No. 15/274,809.
Office action dated Mar. 7, 2019 for U.S. Appl. No. 14/673,565.
Office action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office action dated Mar. 28, 2016 for U.S. Appl. No. 14/673,565.
Office action dated Apr. 4, 2018 for U.S. Appl. No. 15/156,585.
Office action dated May 16, 19 for U.S. Appl. No. 14/515,324.
Office action dated May 18, 2018 for U.S. Appl. No. 14/956,710.
Office Action dated May 31, 2017 for U.S. Appl. No. 15/274,764.
Office action dated Jun. 6, 2019 for U.S. Appl. No. 15/683,713.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
Office action dated Sep. 7, 2018 for U.S. Appl. No. 14/609,332.
Office Action dated Sep. 23, 2016 for U.S. Appl. No. 14/515,324.
Office action dated Oct. 4, 2018 for U.S. Appl. No. 14/515,324.
Office Action dated Oct. 7, 2016 for U.S. Appl. No. 13/945,138.
Office Action dated Nov. 2, 2017 for U.S. Appl. No. 15/156,585.
Office action dated Nov. 2, 2018 for U.S. Appl. No. 14/609,334.
Office Action dated Nov. 15, 2016 for U.S. Appl. No. 14/609,334.
Office action dated Nov. 16, 2017 for U.S. Appl. No. 14/609,332.
Office action dated Nov. 30, 2015 for U.S. Appl. No. 13/945,138.
Office action dated Nov. 30, 2017 for U.S. Appl. No. 14/673,565.
Office action dated Dec. 17, 2015 for U.S. Appl. No. 14/515,324.
Office action dated Dec. 18, 2017 for U.S. Appl. No. 14/515,324.
Office action dated Dec. 18, 2018 for U.S. Appl. No. 14/470,503.
Office action dated Dec. 19, 2017 for U.S. Appl. No. 13/945,138.
PCT/US14/66829 International Search Report dated Feb. 20, 2015.
PCT/US2019/012338 International Search Report dated Apr. 15, 2019.
PCT/US2022/016200 International Search Report and Written Opinion dated May 3, 2022.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
Tolman, et al. Spectrum of liver disease in type 2 diabetes and management of patients with diabetes and liver disease. Diabetes care 30.3 (2007): 734-743.
Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High vol. U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.

(56) References Cited

OTHER PUBLICATIONS

U.S. Appl. No. 14/917,243 Office Action dated Jun. 5, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Dec. 24, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 13/945,138 Office Action dated Dec. 10, 2019.
U.S. Appl. No. 14/515,324 Office Action dated Mar. 31, 2020.
U.S. Appl. No. 14/609,334 Office Action dated Jan. 8, 2020.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
Extended European Search Report mailed Dec. 20, 2024 for European Application No. 22753448.4.

* cited by examiner

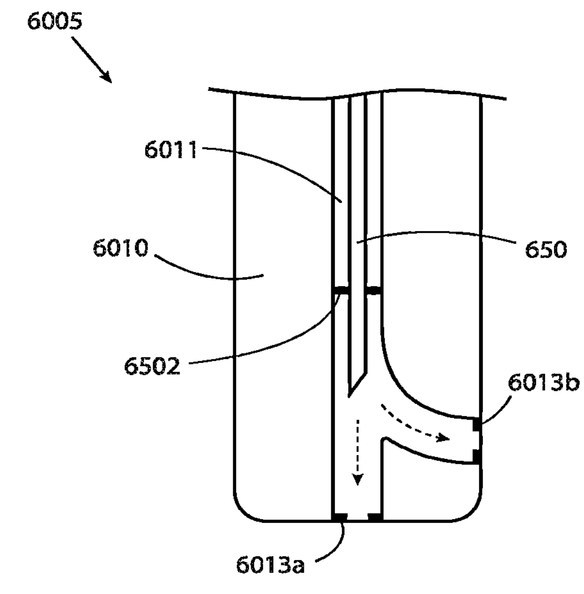
FIG 15A
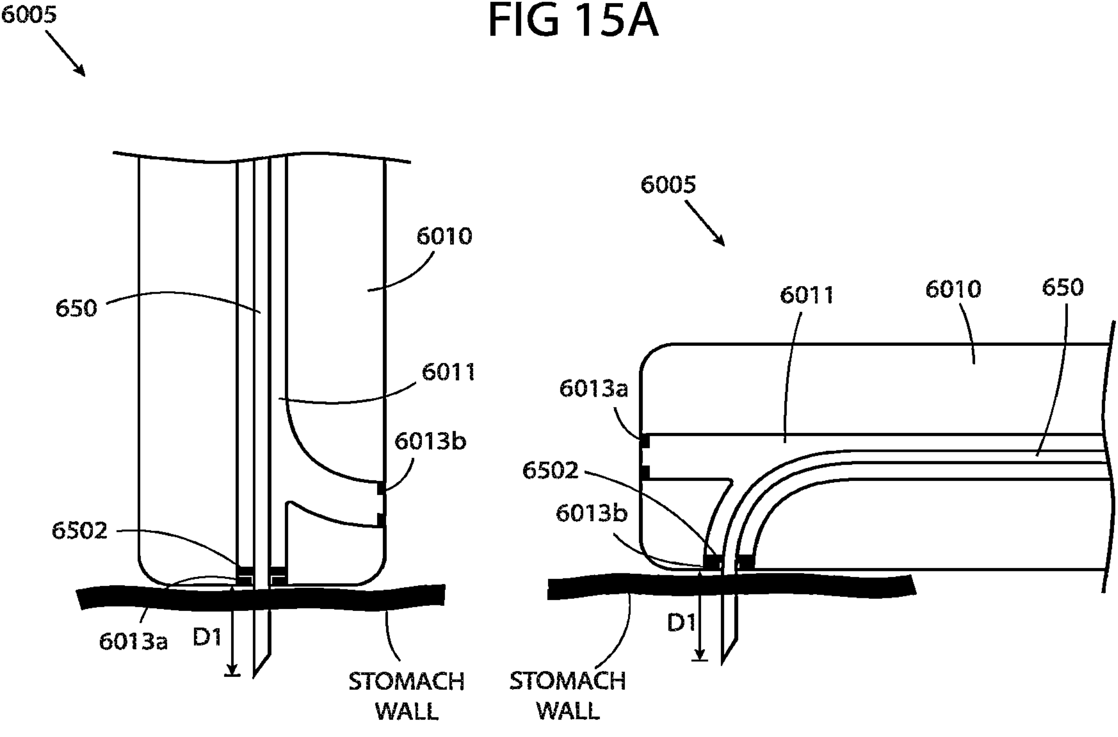
FIG 15B
FIG 15C

SYSTEM FOR TREATING A PATIENT

CROSS-REFERENCE TO RELATED APPLICATIONS

This application is a continuation of PCT Application No PCT/US22/16200, filed Feb. 11, 2022, which claims the benefit of: U.S. Provisional Patent Application Ser. No. 63/148,551, entitled “System for Treating a Patient”, filed Feb. 11, 2021; U.S. Provisional Patent Application Ser. No. 63/214,160, entitled “System for Treating a Patient”, filed Jun. 23, 2021; and U.S. Provisional Patent Application Ser. No. 63/280,383, entitled “System for Treating a Patient”, filed Nov. 17, 2021; the content of each of which is incorporated herein by reference in its entirety for all purposes.

This application is related to: U.S. patent application Ser. No. 16/438,362, entitled “Heat Ablation Systems, Devices and Methods for the Treatment of Tissue”, filed Jun. 11, 2019; U.S. patent application Ser. No. 14/515,324, entitled “Tissue Expansion Devices, Systems and Methods”, filed Oct. 15, 2014; U.S. patent application Ser. No. 16/711,236, entitled “Electrical Energy Ablation Systems, Devices and Methods for the Treatment of Tissue”, filed Dec. 11, 2019; U.S. patent application Ser. No. 14/673,565, entitled “Methods, Systems and Devices for Performing Multiple Treatments on a Patient”, filed Mar. 30, 2015; U.S. patent application Ser. No. 16/379,554, entitled “Methods, Systems and Devices for Reducing the Luminal Surface Area of the Gastrointestinal Tract”, filed Apr. 9, 2019; U.S. patent application Ser. No. 14/917,243, entitled “Systems, Methods and Devices for Treatment of Target Tissue”, filed Mar. 7, 2016; U.S. patent application Ser. No. 16/742,645, entitled “Intestinal Catheter Device and System”, filed Jan. 14, 2020; U.S. patent application Ser. No. 16/798,117, entitled “Systems, Devices and Methods for Performing Medical Procedures in the Intestine”, filed Feb. 21, 2020; U.S. patent application Ser. No. 16/400,491, entitled “Systems, Devices and Methods for Performing Medical Procedures in the Intestine”, filed May 1, 2019; U.S. patent application Ser. No. 16/905,274, entitled “Material Depositing System for Treating a Patient”, filed Jun. 18, 2020; U.S. patent application Ser. No. 17/021,798, entitled “Methods, Systems and Devices for Reducing the Luminal Surface Area of the Gastrointestinal Tract”, filed Sep. 15, 2020; International PCT Patent Application Serial Number PCT/US2020/056627, entitled “Systems, Devices, and Methods for Performing Medical Procedures in the Intestine”, filed Oct. 21, 2020; U.S. patent application Ser. No. 17/095,108, entitled “Systems, Devices and Methods for the Creation of a Therapeutic Restriction in the Gastrointestinal Tract”, filed Nov. 11, 2020; U.S. patent application Ser. No. 17/096,855, entitled “Methods and Systems for Treating Diabetes and Related Diseases and Disorders”, filed Nov. 12, 2020; International PCT Patent Application Serial Number PCT/US2021/013072, entitled “Tissue Treatment Devices, Systems, and Methods”, filed Jan. 12, 2021; International PCT Patent Application Serial Number PCT/US2021/013600, entitled “Automated Tissue Treatment Devices, Systems, and Methods”, filed Jan. 15, 2021; U.S. patent application Ser. No. 17/181,969, entitled “Methods and Systems for Treating Diabetes and Related Diseases and Disorders”, filed Feb. 22, 2021; U.S. patent application Ser. No. 17/192,671, entitled “Ablation Systems, Devices, and Methods for the Treatment of Tissue”, filed Mar. 4, 2021; International PCT Patent Application Serial Number PCT/US2021/022938, entitled “Systems, Devices and Methods for Treating Diabetes”, filed Mar. 18, 2021; U.S. patent application Ser. No. 17/214,157, entitled “Systems and Methods for Deposition Material in a Patient”, filed Mar. 26, 2021; U.S. patent application Ser. No. 17/222,480, entitled “Devices and Methods for the Treatment of Tissue”, filed Apr. 5, 2021; International PCT Patent Application Serial Number PCT/US2021/038371, entitled “Tissue Treatment System with Fluid Delivery Console”, filed Jun. 22, 2021; U.S. patent application Ser. No. 17/384,421, entitled “Systems, Devices and Methods for Performing Medical Procedures in the Intestine”, filed Jul. 23, 2021; U.S. patent application Ser. No. 17/490,947, entitled “Systems, Devices and Methods for Treating Metabolic Medical Conditions”, filed Sep. 30, 2021; U.S. patent application Ser. No. 17/494,277, entitled “Injectate Delivery Devices, Systems and Methods”, filed Oct. 5, 2021; U.S. patent application Ser. No. 17/516,503, entitled “Methods and Systems for Treating Diabetes and Related Diseases and Disorders”, filed Nov. 1, 2021; U.S. Provisional Patent Application Ser. No. 63/292,761, entitled “Methods and Systems for Treating Mucosal Hyperplasia and other Medical Conditions of a Patient”, filed Dec. 22, 2021; and U.S. patent application Ser. No. 17/568,145, entitled “Methods, Systems and Devices for Performing Multiple Treatments on a Patient”, filed Jan. 4, 2022; the contents of each of which is incorporated herein by reference in its entirety for all purposes.

TECHNICAL FIELD

The present invention relates generally to systems for treating a patient, in particular to systems that deliver a material that provides a therapeutic benefit to the patient.

BACKGROUND

The prevalence of metabolic and pancreatic diseases is growing worldwide. Specifically, Type 2 diabetes accounts for significant morbidity and mortality of the population, with and an estimated 50 million people expected to be living with Type 2 diabetes in the United States by 2035. However, approximately 50% of the people diagnosed with Type 2 diabetes in the United States have inadequately controlled disease despite the availability of numerous diagnostic and therapeutic treatments. There is a need for improved systems, methods, and devices for diagnosing and treating metabolic disease. There is an additional need for improved treatments of various diseases and disorders, such as treatment of diabetes.

BRIEF SUMMARY

According to an aspect of the present inventive concepts, a method of treating a medical condition of a patient, comprises selecting a patient for treatment, selecting a depositing device comprising a depositing element, and performing at least one injection comprising advancing the depositing element to a location proximate an at least one deposit site in the patient and delivering treatment agent into the at least one deposit site via the depositing element. The method treats the medical condition of the patient.

In some embodiments, the medical condition comprises a metabolic disease and/or a pancreatic disease.

In some embodiments, the medical condition comprises a medical condition selected from the group consisting of: Type 1 diabetes; Type 2 diabetes; insulin resistance; a metabolic condition; and combinations thereof.

In some embodiments, the medical condition comprises a medical condition selected from the group consisting of:

cystic fibrosis; chronic hyperinsulinemia; chronic pancreatitis; pancreatic cancer; and combinations thereof.

In some embodiments, the method is configured to minimize distribution of the treatment agent to non-target tissue. The non-target tissue can comprise non-target organs of the patient.

In some embodiments, the advancing the depositing element comprises advancing the depositing device into the patient through a working channel of an endoscopic ultrasound device.

In some embodiments, the at least one deposit site comprises one, two, or more locations of the pancreas and/or a blood vessel in fluid communication with the pancreas. The one, two, or more locations can be selected from the group consisting of: intraparenchymal space; anterior pararenal space; intraductal space; intraarterial space of an artery that feeds at least a portion of the pancreas; and combinations thereof. The advancing the depositing element can comprise advancing a distal end of the depositing device through the patient's mouth and through a wall of the patient's gastrointestinal tract to a location proximate the pancreas. The depositing device can be advanced through the working channel of an endoscope that has been advanced through the patient's mouth. The performing of the at least one injection can comprise delivering the treatment agent to: at least 20% of the volume of tissue of the pancreas; at least 10% or at least 20% of the islet cells of the pancreas; at least 10% or at least 20% of the alpha cells of the pancreas; and/or at least 10% or at least 20% of the beta cells of the pancreas. The method can be configured to minimize risk of the patient getting pancreatitis. The patient risk can be minimized to less than 5%, 3%, or 1%. The method can be configured to limit the impact of the treatment agent on a non-target organ to a level that is less than the level of the impact of the treatment agent on the pancreas. The at least one deposit site can comprise a non-cancerous portion of the pancreas. The at least one deposit site can comprise normal parenchymal tissue.

In some embodiments, the treatment agent comprises a gene therapy material. The gene therapy material can comprise adeno-associated virus-based gene therapy material.

In some embodiments, the treatment agent is delivered at a flow rate of no more than 5 mL/min. The treatment agent can be delivered at a flow rate of no more than 3 mL/min or 1 mL/min.

In some embodiments, the total volume of treatment agent delivered comprises a volume of at least 1 mL, a volume of no more than 25 mL, or both. Performing the at least one injection can comprise performing two or more injections in which the depositing element is advanced two or more times.

In some embodiments, the depositing element comprises one or more needles and/or at least one needle with multiple fenestrations, and each needle comprises a distal segment, and the distal segment comprises a maximum size of 25 gauge. The distal segment can comprise a maximum size of 27 gauge. The distal segment can comprise a length of at least 2 cm long.

In some embodiments, the performing of the at least one injection comprises performing a single injection only. The at least one injection can further comprise performing a second delivery of the treatment agent to at least on deposit site.

In some embodiments, the performing of the at least one injection comprises performing multiple injections at different deposit sites. A first injection can be performed at a first deposit site, and at least a second injection can be performed at a second deposit site different than the first deposit site. The performing of the at least one injection can comprise performing no more than seven injections. The performing of the at least one injection can comprise performing no more than five injections, or no more than three injections.

In some embodiments, the method further comprises performing a flush procedure during which a flush material is delivered into the depositing element. The depositing element can comprise a lumen defining a lumen volume, and the volume of the flush material delivered into the depositing element can comprise a volume at or below the lumen volume. The flush material can comprise a material selected from the group consisting of: mineral oil; lipiodol; and combinations thereof.

In some embodiments, the method further comprises delivering a tissue-disseminating agent to the at least one deposit site prior to and/or during the performing of the at least one injection of the treatment agent to the at least one deposit site. The tissue-disseminating agent can be delivered separately from the delivery of the treatment agent. The tissue-disseminating agent can be delivered simultaneously with the delivery of the treatment agent. The tissue-disseminating agent can be co-formulated with the treatment agent.

According to another aspect of the present inventive concepts, a system for treating a medical condition of a patient, comprises a treatment agent and a depositing device comprising a depositing element. The depositing element is configured to perform at least one injection comprising: advancing the depositing element to a location proximate at least one deposit site in the patient; and delivering the treatment agent into the at least one deposit site via the depositing element. The system is configured to treat the medical condition of the patient.

In some embodiments, the medical condition comprises a condition selected from the group consisting of: a metabolic condition; pancreatic disease; Type 1 diabetes; Type 2 diabetes; insulin resistance; cystic fibrosis; chronic hyperinsulinemia; chronic pancreatitis; pancreatic cancer; and combinations thereof.

In some embodiments, the system further comprises a console operably attachable to the depositing device, and the console is configured to control one or more parameters of the at least one injection performed by the depositing device.

In some embodiments, the system further comprises an access device for advancing the depositing device into the patient. The access device can comprise an ultrasound-guided endoscope.

In some embodiments, the system further comprises a syringe, and the syringe is removably attachable to the depositing device, and the syringe comprises the treatment agent prior to the treatment agent being delivered by the depositing element to the at least one deposit site. The system can further comprise a syringe drive configured to cause the treatment agent to exit the syringe and be delivered by the depositing element into the at least one deposit sites, and the syringe driver can be configured to cause the treatment agent to be delivered to the at least one deposit site at a flow rate of no more than 5 mL/min. The syringe drive can be configured to cause the treatment agent to be delivered to the at least one deposit site at a flow rate of no more than 3 mL/min, or no more than 1 mL/min. The system can further comprise a conduit that fluidly attaches the syringe to the depositing device. The conduit can comprise a length of no more than 10 cm. The depositing device, the syringe, and/or the conduit can comprise a sealed fluid pathway configured to prevent the treatment agent from exiting the fluid pathway when one of the depositing device, syringe, and/or conduit is detached from another of the depositing device, syringe, and/or conduit. The system can further comprise a second syringe and a flush material, and the second syringe can be configured to deliver the flush material to the depositing element.

In some embodiments, the depositing element comprises at least one needle comprising a luminal wall surrounding a lumen that extends through the needle. The luminal wall can comprise a material selected from the group consisting of: stainless steel; nickel-titanium alloy; titanium; cobalt chromium; fused silica; polyethylene; polypropylene; polyether ether ketone (PEEK); polytetrafluoroethylene (PTFE); a fluoropolymer; a sol-gel nanocomposite; a material comprising a hydrophobic coating and/or a hydrophilic coating; and combinations thereof. The at least one needle can comprise a distal segment with a diameter of no more than 25 gauge. The distal segment can comprise a length of at least 2 cm. The distal segment can comprise a diameter of no more than 27 gauge.

In some embodiments, the treatment agent comprises a gene therapy material. The gene therapy material can comprise an adeno-associated virus-based gene therapy material.

According to another aspect of the present inventive concepts, a method comprising advancing a depositing device comprising at least one depositing element to at least one pancreatic deposit site in a patient having a metabolic disease and/or a pancreatic disease, and delivering a treatment agent through the at least one depositing element into the at least one pancreatic deposit site. The at least one depositing element can comprise at least one needle positioned on a distal portion of the depositing device. The distal end of the depositing device can be delivered into the patient through the mouth, and advanced through a wall of the gastrointestinal tract to a location proximate the pancreas. The depositing device can be delivered through a working channel of a gastrointestinal endoscope that has been delivered through the mouth of the patient. The depositing device can be delivered alongside a gastrointestinal endoscope that has been delivered through the mouth of the patient.

In some embodiments, the metabolic disease is selected from the group consisting of: Type 1 diabetes; Type 2 diabetes; nonalcoholic fatty liver disease (NAFLD); nonalcoholic steatohepatitis (NASH); obesity; and combinations thereof.

In some embodiments, the pancreatic disease is selected from the group consisting of: pancreatitis; pancreatic cancer; hyperinsulinism; and combinations thereof.

In some embodiments, the at least one pancreatic deposit site is selected from the group consisting of: intraparenchymal space; anterior pararenal space; intraductal space; intraarterial space of an artery that feeds at least a portion of the pancreas; and combinations thereof.

In some embodiments, the delivering of a treatment agent comprises at least a first delivery in which a minimum volume of the treatment agent is delivered into the pancreatic parenchyma, and the minimum volume of treatment agent comprises a volume sufficient to cause at least a portion of the volume of the treatment agent to exit into the anterior pararenal space, spread, and re-enter the pancreas. The method can further comprise at least a second delivery of the treatment agent to at least one additional deposit site proximate the tail of the pancreas.

In some embodiments, the delivering of a treatment agent comprises at least a first delivery in which a minimum volume of treatment agent is delivered into the pancreatic parenchyma, and the minimum volume of the treatment agent comprises a volume of at least 2 ml, at least 3 ml, and/or at least 5 ml.

In some embodiments, the depositing device is advanced to the at least one pancreatic deposit site under image guidance. The image guidance can comprise: endoscopic ultrasound guidance; computerized tomography (CT) guidance; and/or magnetic Resonance Imaging (MRI) guidance.

In some embodiments, the at least one pancreatic deposit site comprises locations within 10 cm, 7.5 cm, 5 cm, and/or 3 cm of a portion of the pancreas, and the portion of the pancreas comprises the tail, the neck, the body, the head, and/or the uncinate process.

In some embodiments, the treatment agent and/or the at least one depositing element is configured to be visualized by an imaging device, and the method further comprises visualizing the treatment agent and/or the at least one depositing element with the imaging device to confirm proper delivery of the treatment agent.

In some embodiments, the method further comprises delivering an imaging agent through the at least one depositing element and visualizing the delivery of the imaging agent with an imaging device to confirm subsequently proper delivery of the treatment agent.

In some embodiments, the method further comprises pre-loading the depositing device with the treatment agent. The treatment agent can be loaded into the depositing device from the distal end of the depositing device.

In some embodiments, the delivering of a treatment agent is performed at a pressure of at least 3 mmHg.

In some embodiments, the delivering of a treatment agent is performed at a pressure of no more than 25 mmHg.

In some embodiments, the delivering of a treatment agent is performed at a flow rate of at least 1 ml/min.

In some embodiments, the delivering of a treatment agent is performed at a flow rate of no more than 5 ml/min.

In some embodiments, the at least one depositing element comprises multiple fenestrations along its length.

In some embodiments, the method further comprises confirming the at least one depositing element is in a proper location prior to delivering the treatment agent.

In some embodiments, the method further comprises the delivery of a permeability-enhancing agent prior to the delivery of the treatment agent and/or simultaneously with the delivery of the treatment agent. The delivery of the permeability-enhancing agent can be performed locally and/or intravenously. The permeability-enhancing agent can comprise an agent selected from the group consisting of: hyaluronidase; collagenase; losartan; and combinations thereof.

In some embodiments, the treatment agent comprises a coformulation of the treatment agent and the permeability-enhancing agent.

In some embodiments, the treatment agent is a gene therapy agent. The gene therapy agent can comprise a non-viral vector comprising a polynucleotide comprising a gene of interest. The non-viral vector can be selected from the group consisting of: plasmids, bacterial artificial chromosomes, yeast artificial chromosomes, and minicircles. The gene therapy agent can comprise a viral vector comprising a polynucleotide comprising a gene of interest. The viral vector can be selected from the group consisting of retrovirus vectors, adenovirus vectors, Herpes simplex virus (HSV) vectors, and adeno-associated virus (AAV) vectors. The viral vector can be an AAV vector. The AAV vector can comprise an AAV vector genome comprising the polynucleotide comprising a gene of interest. The AAV vector can further comprise an AAV capsid protein. The AAV capsid protein can be selected from the group consisting of AAV1, AAV2, AAV3, AAV4, AAV5, AAV6, AAV7, AAV8, AAV9, AAV10, AAV11, Rh10, Rh74, AAV-2i8, AAV-DJ, AAV-LK03, AAV-KP1, AAV-KP2, and AAV-KP3 capsid proteins and variants thereof.

In some embodiments, the method further comprises heating tissue proximate the at least one pancreatic deposit site to a temperature above 39° C. prior to, during, and/or after the delivery of the treatment agent.

In some embodiments, the method further comprises delivering a dissemination-blocking material that is configured to prevent undesired dissemination of the treatment agent to non-target locations. The dissemination-blocking material can comprise a viscous substance and/or a polymer.

In some embodiments, the method further comprises positioning a blocking element in the patient, and the blocking element is configured to prevent undesired dissemination of the treatment agent to non-target locations.

In some embodiments, the method further comprises removing at least a portion of the treatment agent from a deposit site location after the delivery of the treatment agent begins.

In some embodiments, the method further comprises removing all of the treatment agent.

According to another aspect of the present inventive concepts, a method comprising endoscopically delivering a gene therapy agent to an intraparenchymal space of the pancreas of a patient having a metabolic disease and/or a pancreatic disease. The delivering can comprise advancing a depositing device comprising at least one depositing element through the mouth and through a wall of the gastrointestinal tract to the intraparenchymal space of the pancreas. The depositing device can be delivered through a working channel of a gastrointestinal endoscope that has been delivered through the mouth of the patient. The depositing device can be delivered alongside a gastrointestinal endoscope that has been delivered through the mouth of the patient.

In some embodiments, the gene therapy agent comprises an adeno-associated virus (AAV) vector. The AAV vector can comprise (a) an AAV capsid protein and (b) an AAV vector genome comprising a polynucleotide comprising a gene of interest. The AAV capsid protein can be selected from the group consisting of AAV1, AAV2, AAV3, AAV4, AAV5, AAV6, AAV7, AAV8, AAV9, AAV10, AAV11, Rh10, Rh74, AAV-2i8, AAV-DJ, AAV-LK03, AAV-KP1, AAV-KP2, and AAV-KP3 capsid proteins and variants thereof.

In some embodiments, the patient has Type 2 diabetes.

In some embodiments, the gene of interest encodes a glucoregulatory hormone (i.e., a hormone involved in the modulation of circulating blood glucose levels). The glucoregulatory hormone can be selected from glucagon, GLP-1, oxyntomodulin, glicentin, glicentin-related polypeptide (GRPP), major proglucagon fragment, intervening peptide 1 (IP-1), intervening peptide 2 (IP-2), GLP-2, glucose-dependent insulinotropic peptide (GIP), peptide tyrosine (PYY), Cholecystokinin (CCK), somatostatin, oxyntomodulin, Ghrelin, amylin, glucagon, leptin, follistatin, insulin-like growth factor 1 (IGF1), vasoactive intestinal peptide (VIP), and growth hormone 1 (GH1), and peptides, variants and fusions thereof.

According to another aspect of the present inventive concepts, a method of treating a patient with a metabolic disease and/or a pancreatic disease comprises: selecting a patient with a metabolic disease and/or a pancreatic disease; selecting one or more pancreatic deposit sites; advancing a depositing device comprising a at least one depositing element to the selected one or more pancreatic deposit sites; and delivering a treatment agent through the at least one depositing element into the selected one or more pancreatic deposit sites. The method is configured to achieve a therapeutic benefit for the patient.

In some embodiments, the at least one depositing element comprises one, two, or more needles positioned on a distal portion of the depositing device.

In some embodiments, the distal end of the depositing device is delivered into the patient through the mouth, and advanced through a wall of the gastrointestinal tract to a location proximate the pancreas. The depositing device can be delivered through a working channel of a gastrointestinal endoscope that has been delivered through the mouth of the patient. The depositing device can be delivered alongside a gastrointestinal endoscope that has been delivered through the mouth of the patient.

In some embodiments, the method treats a metabolic disease of the patient selected from the group consisting of: Type 2 diabetes; NAFLD; NASH; obesity; and combinations thereof.

In some embodiments, the method treats a pancreatic disease of the patient selected from the group consisting of: pancreatitis; pancreatic cancer; hyperinsulinism; and combinations thereof.

In some embodiments, the selected one or more pancreatic deposit sites comprise one or more sites selected from the group consisting of: intra-parenchymal space; anterior pararenal space; intraductal space; intra-arterial space of an artery that feeds at least a portion of the pancreas; and combinations thereof.

In some embodiments, the delivering of the treatment agent comprises at least a first delivery in which a minimum volume of the treatment agent is delivered into the pancreatic parenchyma, and the minimum volume of treatment agent comprises a volume sufficient to cause at least a portion of the volume of the treatment agent to exit into the anterior pararenal space, spread, and re-enter the pancreas. The method can further comprise at least a second delivery of the treatment agent to one or more additional deposit sites proximate the tail of the pancreas.

In some embodiments, the delivering of the treatment agent comprises at least a first delivery in which a minimum volume of treatment agent is delivered into the pancreatic parenchyma, and the minimum volume of the treatment agent comprises a volume of at least 2 mL, at least 3 mL, and/or at least 5 mL.

In some embodiments, the depositing device is advanced to the selected one or more pancreatic deposit sites under image guidance. The image guidance can comprise: ultrasound guidance (e.g. endoscopic ultrasound guidance); CT guidance; and/or MRI guidance.

In some embodiments, the therapeutic benefit is achieved for a time period of at least 6 months.

In some embodiments, the selected one or more pancreatic deposit sites comprise locations within 10 cm, 7.5 cm, 5 cm, and/or 3 cm of a portion of the pancreas, and the portion of the pancreas comprises the tail, the neck, the body, the head, and/or the uncinate process.

In some embodiments, the treatment agent and/or the at least one depositing element is configured to be visualized by an imaging device, and the method further comprises visualizing the treatment agent and/or the at least one depositing element with the imaging device to confirm proper delivery of the treatment agent.

In some embodiments, the method further comprises delivering an imaging agent through the at least one depositing element and visualizing the delivery of the imaging agent with an imaging device to confirm subsequently proper delivery of the treatment agent.

In some embodiments, the method further comprises pre-loading the depositing device with the treatment agent. The treatment agent can be loaded into the depositing device from the distal end of the depositing device.

In some embodiments, the delivering of the treatment agent is performed at a pressure of at least 3 mmHg.

In some embodiments, the delivering of the treatment agent is performed at a pressure of no more than 25 mmHg.

In some embodiments, the delivering of the treatment agent is performed at a flow rate of at least 1 mL/min.

In some embodiments, the delivering of the treatment agent is performed at a flow rate of no more than 5 mL/min.

In some embodiments, the at least one depositing element comprises multiple fenestrations along its length.

In some embodiments, the method further comprises confirming the at least one depositing element is in a proper location prior to delivering the treatment agent.

In some embodiments, the method further comprises the delivery of a permeability-enhancing agent prior to the delivery of the treatment agent and/or simultaneously with the delivery of the treatment agent. The delivery of the permeability-enhancing agent can be performed locally and/or intravenously. The permeability-enhancing agent can comprise an agent selected from the group consisting of: hyaluronidase; collagenase; losartan; and combinations thereof. The treatment agent can comprise a coformulation of the treatment agent and the permeability-enhancing agent.

In some embodiments, the method further comprises heating tissue proximate the selected one or more pancreatic deposit sites to a temperature above 39° C. prior to, during, and/or after the delivery of the treatment agent.

In some embodiments, the method further comprises delivering a dissemination-blocking material that is configured to prevent undesired dissemination of the treatment agent to non-target locations. The dissemination-blocking material can comprise a viscous substance and/or a polymer.

In some embodiments, the method further comprises positioning a blocking element in the patient, and the blocking element is configured to prevent undesired dissemination of the treatment agent to non-target locations.

In some embodiments, the method further comprises removing at least a portion of the treatment agent from a deposit site location after the delivery of the treatment agent begins.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

BRIEF DESCRIPTION OF THE DRAWINGS

FIGS. 15A-15C illustrate side sectional views of the distal portion of a depositing device, consistent with the present inventive concepts.

DETAILED DESCRIPTION OF THE DRAWINGS

Figure 1:
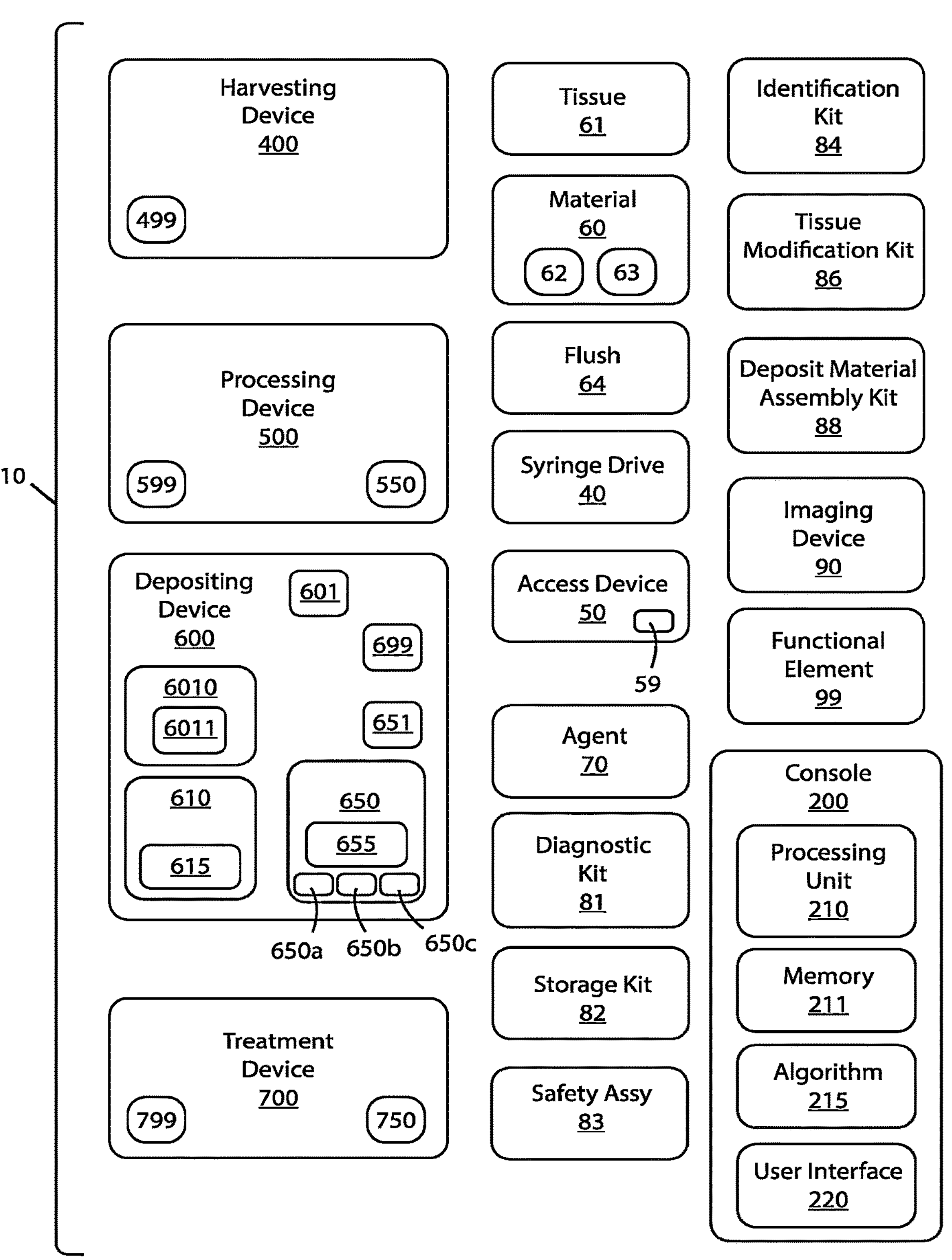
FIG. 1 illustrates a system for depositing material at a deposit site of a patient, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one, two, or more of these.

As used herein, the term "proximate" shall include locations relatively close to, on, in and/or within a referenced component, anatomical location, or other location. As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

In this specification, unless explicitly stated otherwise, "and" can mean "or," and "or" can mean "and." For example, if a feature is described as having A, B, or C, the feature can have A, B, and C, or any combination of A, B, and C. Similarly, if a feature is described as having A, B, and C, the feature can have only one or two of A, B, or C.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold. within a threshold range of values and/or outside a threshold range of values, to cause a desired effect (e.g. efficacious therapy) and/or to prevent or at least reduce the effects of (hereinafter "prevent" or "reduce") an undesired event (e.g. a device and/or clinical adverse event).

In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. "Positive pressure" includes pressure above room pressure or simply a pressure that is greater than another pressure, such as a positive differential pressure across a fluid pathway component such as a valve. "Negative pressure" includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function. In some embodiments, a functional element comprises one or more elements constructed and arranged to perform a function selected from the group consisting of: deliver energy; extract energy (e.g. to cool a component); deliver a pharmaceutical drug or other agent; manipulate a system component or patient tissue; record or otherwise sense a parameter such as a patient physiologic parameter or a patient anatomical parameter; and combinations of one or more of these. A functional element can comprise a fluid, such as an ablative fluid (as described hereabove) comprising a liquid or gas configured to ablate or otherwise treat tissue. A functional element can comprise a reservoir, such as an expandable balloon configured to receive an ablative fluid. A "functional assembly" can comprise an assembly constructed and arranged to perform a function, such as is described hereabove. In some embodiments, a functional assembly is configured to deliver energy and/or otherwise treat tissue (e.g. a functional assembly configured as a treatment assembly). Alternatively or additionally, a functional assembly can be configured to record one or more parameters, such as a patient physiologic parameter; a patient anatomical parameter; a patient environment parameter; and/or a system parameter. A functional assembly can comprise an expandable assembly. A functional assembly can comprise one or more functional elements.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, thermal energy such as heat energy and/or cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one, two, or more of these.

As used herein, the term "fluid" can refer to a liquid, gas, gel, and/or any flowable material, such as a material which can be propelled through a lumen and/or opening.

As used herein, the term "tissue modification procedure" refers to a procedure performed on tissue to modify a property of the tissue treated and/or tissue proximate the tissue treated ("treated tissue" herein). A tissue modification procedure can comprise a procedure in which a treatment agent, such as a gene therapy material or other agent is delivered to tissue. A tissue modification procedure can result in necrosis and/or removal of tissue, after which "replacement tissue" develops in the place of the removed tissue, the replacement tissue having different properties than the tissue that was removed. A tissue modification procedure can result in a reduction in surface area of the treated tissue (e.g. a reduction in the luminal surface area of an inner wall of tubular tissue), such as to modify secretions and/or absorptions of the tissue. A tissue modification procedure can include: delivery of energy to tissue (e.g. delivery of ablative heat, ablative cold, and/or ablative electromagnetic energy); mechanical removal and/or disruption of tissue; chemical ablation of tissue; and combinations of one, two, or more of these. Treated tissue or replacement tissue ("treated tissue" herein) can have modified properties including but not limited to: modification of one or more absorptive properties of the tissue; modification of one or more secretive properties of the tissue; modification of neuronal signaling of the tissue; and combinations of one, two or more of these. Effects of the tissue modification procedure can occur acutely and/or it can take place over time, such as days, weeks or months. In some embodiments, a tissue modification procedure includes injecting one or more materials into the submucosal tissue of a GI lumen, such as to expand a submucosal tissue layer, for example a full (360°) or partial circumferential expansion of an axial segment of the GI tract. These tissue expansion procedures can cause a relatively acute result (e.g. less than 30 minutes), such as to perform a subsequent mucosal ablation procedure wherein the expanded tissue acts as a safety margin of tissue during the ablation, protecting the underlying layers from damage. In some embodiments, the full or partial circumferential submucosal tissue expansion is performed to cause luminal narrowing at the axial segment, such as is described in applicant's co-pending application U.S. patent application Ser. No. 17/095,108, entitled "Systems, Devices and Methods for the Creation of a Therapeutic Restriction in the Gastrointestinal Tract", filed Nov. 11, 2020, the contents of which are incorporated herein by reference in its entirety. This luminal narrowing can be configured to last for a prolonged period of time, such as at least 1 day, at least 1 week, and/or at least one month. This luminal narrowing can be performed to restrict food intake of the patient, and/or for other purposes.

As used herein, the term "ablative temperature" refers to a temperature at which tissue necrosis or other desired tissue treatment occurs (e.g. a temperature sufficiently hot or sufficiently cold to cause tissue necrosis or any desired effect). As used herein, the term "ablative fluid" refers to one or more liquids, gases, gels or other fluids whose thermal properties cause tissue necrosis and/or another desired tissue treatment (e.g. one or more fluids at an ablative temperature). Alternatively or additionally, "ablative fluid" refers to one or more fluids whose chemical properties (at room temperature, body temperature or otherwise) cause tissue necrosis or another desired tissue treatment. A treatment element (e.g. a functional element) of the present inventive concepts can comprise one or more ablative fluids and/or comprise one or more elements that deliver one or more ablative fluids (e.g. deliver the fluids onto a tissue surface and/or into a volume of tissue).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Obesity and Type 2 Diabetes are twin epidemics associated with a Western Diet and sedentary lifestyle, and both of which are increasing in prevalence at startling rates. A normal endocrine pancreas produces insulin in response to glucose intake, but in patients with Type 2 diabetes, the insulin production capacity of the pancreas is significantly reduced and is no longer sufficient to control blood glucose.

Type 1 Diabetes is also a disease of the pancreas, in which the patient's immune system attacks the insulin-producing beta cells within the pancreas, leading to significantly reduced insulin production capacity and insufficient control of blood glucose.

Cystic fibrosis (CF) is the most common genetic disorder and causes a significant damage in secretory epithelial cells due to mutations in the CTFR gene. CF in the pancreas can cause pancreatic exocrine insufficiency and consequent digestive dysfunction in the intestine, abdominal pain, an increased risk of acute pancreatitis, and a significant decrease in the quality of life.

Ex vivo gene therapy techniques have been tested in animal models to attempt to improve pancreatic function, for example to cause transgenic overexpression of hepatocyte growth factor in the endocrine pancreas to stimulate insulin production. The ex vivo approach requires a complicated removal of pancreatic cells, ex vivo transduction, and reimplantation. Intraperitoneal injection of gene therapy agents is known to enable gene therapy in rodent models, as the pancreas is accessible to the peritoneal cavity. However, in humans, the pancreas is not accessible to the peritoneal cavity. To date, the rate of gene therapy transduction of the pancreas with an intravenous delivery of gene therapy agents has been shown to be well below therapeutic thresholds.

According to the American Cancer Society, the five year survival rate for localized pancreatic cancer is 39%. Chemotherapy, using an intravenous infusion of gemcitabine or other agents, is an established therapy for pancreatic cancer. However, dosage is limited by systemic delivery and consequent off-target effects. Local drug delivery systems, such as gemcitabine-eluting membranes, have been implanted in the pancreas of mice as a means of providing local delivery of chemotherapeutic agents, but this requires both an implantable device and a complicated pancreatic surgery.

Pancreatitis is inflammation of the pancreas that can worsen over time and lead to permanent damage to the pancreas. Chronic pancreatitis eventually impairs a patient's ability to digest food and produce pancreatic hormones. Intra-pancreatic trypsinogen activation is believed to contribute to the pathogenesis of both acute and chronic pancreatitis. Trypsin inhibitors have demonstrated effectiveness in mouse models of pancreatitis. However, systemic trypsin inhibition is known to interfere with normal digestion, leading to malnutrition, delayed growth, and other metabolic and digestive disorders.

A total pancreatectomy with intraportal islet cell autotransplant is increasingly being offered to patients with chronic pancreatitis (CP). Intraportal delivery of pancreatic islets is an established therapy to restore some endocrine function to patients that have received a total pancreatectomy. Currently, the intraportal islet cell autotransplant procedure is performed with either a surgical approach or a transabdominal percutaneous approach. Complications of the current approaches include bleeding, thrombosis, and iatrogenic injury to anatomical structures.

Provided herein are systems and methods for implanting or otherwise depositing material (e.g. material including a treatment agent) at a deposit site of a patient (e.g. a mammalian patient), such as to provide a therapeutic benefit to the patient. The systems and methods can be configured to treat a "medical condition" of the patient, such as one, two, three or more diseases, disorders, and/or other medical conditions of a patient. The system includes a depositing device for the depositing material at a deposit site. The deposited material can comprise a treatment agent comprising a gene therapy material (e.g. a material comprising a gene therapy vector and/or a gene editing vector), and/or a material that is based on tissue harvested at a harvest site with a harvesting device of the system. Alternatively or additionally, the deposited material can comprise a treatment agent comprising an oncolytic virus, a cell therapy, antisense oligonucleotides, aptamers, small interfering RNAs, microRNAs, and/or messenger RNAs. The deposited material "modifies" tissue (e.g. modifies existing tissue and/or causes new tissue to be generated), and the modified tissue is configured to treat the medical condition of the patient. The systems of the present inventive concepts can be configured to maximize efficacy of the delivery of one or more materials to a deposit site (e.g. target tissue) of a patient, while minimizing patient risk as well as preventing or at least reducing the delivery of the one or more materials to undesired (e.g. off-target) tissue locations. In some embodiments, a treatment agent, such as an agent comprising at least a gene therapy material, is delivered to the pancreas of a patient to provide a therapeutic benefit to the patient. The treatment material can be delivered to at least 20% of the volume of the pancreas (e.g. the volume of the pancreatic tissue), and the treatment material can be delivered at a relatively slow flow rate. Therapeutic benefit can be achieved with minimal risk of pancreatitis, and while avoiding any significant distribution of the treatment agent to non-target organs.

Referring now to FIG. 1, a schematic view of a system for depositing a material at a deposit site of a patient is illustrated, consistent with the present inventive concepts. System 10 includes depositing device 600. Depositing device 600 comprises a device for performing a treatment procedure comprising implanting, placing, seeding, inserting, spraying, topically applying, and/or otherwise depositing ("depositing" herein) a treatment agent, such as material 60 shown and described herebelow, at a "deposit site" of a patient. The deposit site can comprise one, two, or more sites on and/or within a patient (e.g. on the patient's skin and/or within the body of the patient, respectively). After the depositing of material 60, tissue at the deposit site is modified, and tissue at locations proximate the deposit site is modified. These tissue modifications can include but are not limited to: creation of new tissue; gene modification and/or other modification of existing tissue; treatment of tissue with a pharmaceutical or other agent (e.g. treatment with an anti-pancreatitis pharmaceutical agent); destruction of tissue (e.g. via a chemotherapy agent); other modification of tissue; and combinations of these. The modified tissue (e.g. tissue including material 60 and/or tissue void of material 60) comprises "resultant tissue" herein. Properties of the resultant tissue can be driven by or otherwise based on material 60 (e.g. properties including expression of one or more proteins by the resultant material). Generation of the resultant tissue by the systems, devices, and methods of the present inventive concepts can provide a therapeutic benefit used to treat one or more medical conditions of the patient.

In some embodiments, system 10 delivers a gene therapy material (also referred to herein as a "gene therapy agent") to tissue at or otherwise proximate target tissue that is to be modified by the gene therapy material. The gene therapy delivered by system 10 can deliver a material 60 comprising a gene therapy vector (e.g. a gene therapy vector which carries and adds a new transgene to a cell) and/or a material 60 comprising a gene editing vector (e.g. a gene editing vector which carries a gene editing sequence and modifies an existing gene in a cell). In some embodiments, system 10 delivers a material 60 comprising both a gene therapy vector and a gene editing vector. Alternatively or additionally, material 60 can comprise a treatment agent comprising an oncolytic virus, a cell therapy, antisense oligonucleotides, aptamers, small interfering RNAs, microRNAs, and/or messenger RNAs. In some embodiments, a material 60 comprising a gene editing vector comprises a virus-based, a lipid nanoparticle-based, and/or a plasmid-based vector. In these embodiments (e.g. when material 60 comprises a plasmid-based vector), depositing device 600, an access device (e.g. an endoscope or other access device 50 as described herebelow) and/or another component of system 10 can comprise a functional element (e.g. functional element 699 of device 600, and/or a functional element 59 of an access device 50) that comprises an electroporation delivery element and/or sonoporation delivery element that is used prior to, during, and/or subsequent to the delivery of material 60. For example, electroporation and/or sonoporation can be delivered by these functional elements (e.g. electrodes and/or ultrasound transducers, respectively) to cause electrical and/or mechanical perturbation of the cell membrane (e.g. transient membrane permeabilization) allowing the uptake of large molecules in the vicinity of the energy delivery.

Depositing device and/or other components of system 10 can be configured to avoid passing through (e.g. and undesirably damaging) certain tissue, "non-target tissue" herein, such as certain blood vessels, ducts, organ tissue, and the like (e.g. tissue that is not be treating by system 10). Depositing device 600 can also be configured to prevent or at least reduce delivery of material 60 to an undesired location, also referred to as "non-target tissue" herein, including tissue that is on (e.g. skin) and/or within the patient, such as to avoid undesired effects that material 60 may have on the non-target tissue. In some embodiments, depositing device 600 is configured to minimize distribution of material 60 to one or more non-target tissue locations, such as one or more "non-target organ" locations, as described herein.

Material 60 can comprise a gene therapy material, such as a gene therapy vector and/or a gene editing vector. In some embodiments, material 60 comprises a gene editing vector comprising an RNA vector. In some embodiments, system 10 delivers a gene editing vector directly to the target tissue (e.g. organ tissue) to prevent or at least reduce ("prevent" or "reduce" or "minimize" herein) systemic delivery of the gene editing vector (e.g. to prevent undesired delivery of the gene editing vector to the venous system or other undesired location, such as to prevent an undesired delivery that would cause undesired transduction of off-target organs).

In some embodiments, system 10 includes a device for harvesting tissue of the patient, harvesting device 400 shown, which can be configured to harvest tissue, tissue 61 described herebelow, at a "harvest site" of the patient. The harvest site can include one, two, or more patient tissue locations such as one or more locations on the skin of the patient, and/or one or more locations within the patient's body. In some embodiments, system 10 includes a device, processing device 500 shown, that can be configured to process tissue 61. Processing device 500 comprises one or more elements for processing tissue 61, processing element 550 shown. Processing device 500 can be used to process tissue 61 after its harvest by harvesting device 400. In some embodiments, processing device 500 is configured to treat in-situ tissue prior to its harvest. In some embodiments, system 10 does not include harvesting device 400, such as when target tissue is modified by a gene therapy material (e.g. a gene therapy vector and/or a gene editing vector), and no tissue of the patient is harvested in order to provide a therapeutic benefit. In some embodiments, system 10 includes one or more treatment devices, treatment device 700 shown. Treatment device 700 is configured to treat tissue at a "treatment site" of the patient. The treatment site can include one or more locations on the skin of the patient, and/or one or more locations within the patient's body. In some embodiments, treatment device 700 treats tissue of a deposit site and/or tissue proximate a deposit site, such as when performing a tissue treatment procedure (e.g. of tissue at or otherwise proximate a deposit site, or remote from a deposit site) prior to the depositing of material 60 at a deposit site.

System 10 can include one or more consoles, console 200 shown. Console 200 can operably attach (e.g. fluidly, electrically, pneumatically, hydraulically, optically, and/or acoustically attach) to one or more of devices 400, 500, 600, and/or 700. Console 200 can comprise a microcontroller or other central processing unit, processing unit 210 shown. System 10 can comprise one or more algorithms, algorithm 215. Processing unit 210 can comprise one or more electronic elements, electronic assemblies, and/or other electronic components, such as components selected from the group consisting of: memory storage components; analog-to-digital converters; rectification circuitry; state machines; microprocessors; microcontrollers; filters and other signal conditioners; sensor interface circuitry; transducer interface circuitry; and combinations thereof. In some embodiments, processing unit 210 comprises a memory storage component, memory 211 shown, that can include instructions, such as instructions used by processing unit 210 to perform an algorithm, such as algorithm 215. In some embodiments, algorithm 215 includes a bias, such as a bias toward or away from false-positives or false-negatives. In some embodiments, algorithm 215 includes a bias configured to cause a trajectory used to advance a component of system 10 toward and/or away from an object. For example, algorithm 215 can include a bias to tend to cause a planned trajectory and/or an actual trajectory of depositing element 650 and/or a portion of depositing device 600 (e.g. the distal portion of device 600) to tend to travel away from particular tissue or other anatomical locations of a patient, such as to tend to cause the associated trajectory to tend to avoid certain tissue types and/or anatomical locations, as described herein. In some embodiments, console 200 comprises one or more user interfaces, user interface 220 shown, such as a user interface including one or more user input and/or user output components (e.g. a display such as a touchscreen display).

Figure 2:
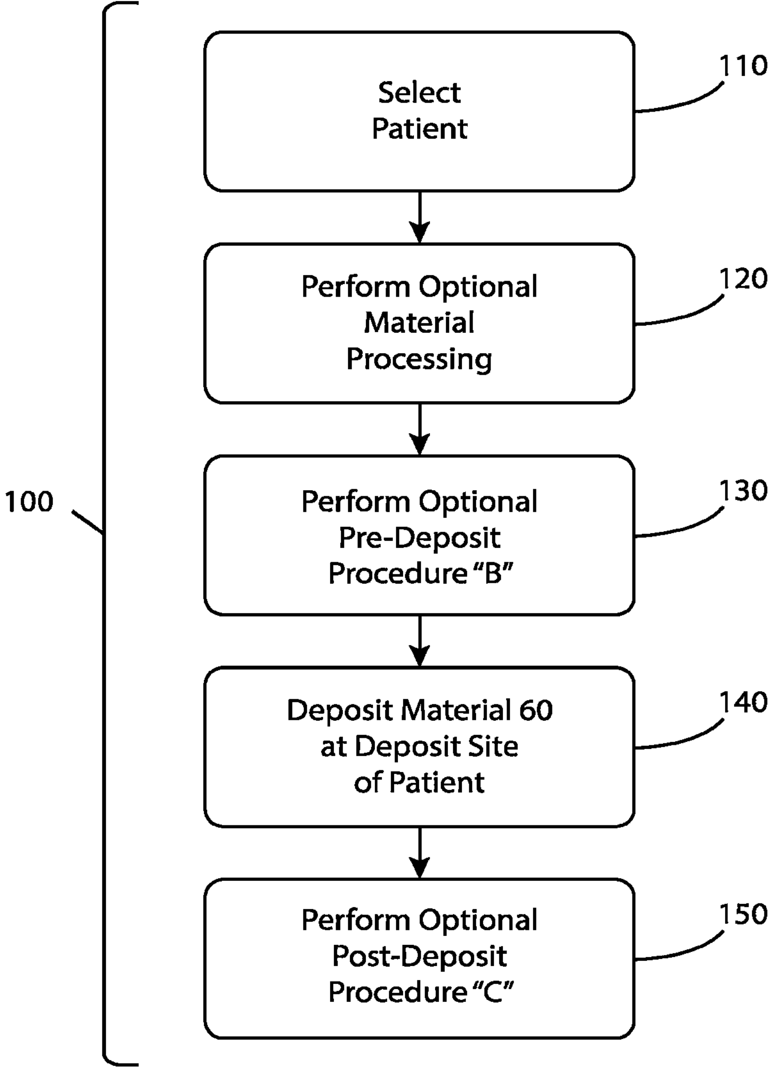
FIG. 2 illustrates a flow chart of another method for depositing material at a deposit site of a patient, consistent with the present inventive concepts.

In some embodiments, system 10 is configured to provide a treatment as described herebelow in reference to FIG. 2. System 10 can be configured to treat one, two, three, or more medical conditions selected from the group consisting of: Type 2 diabetes; Type 1 diabetes; Double diabetes; gestational diabetes; other forms of diabetes; hyperglycemia; pre-diabetes; monogenic diabetes; maturity onset diabetes of the young; impaired glucose tolerance; insulin resistance; hyperinsulinemia; hypoinsulinemia; non-diabetic hypoglycemia; elevated albuminuria; non-alcoholic fatty liver disease (NAFLD); non-alcoholic steatohepatitis (NASH); obesity; obesity-related disorder; polycystic ovarian syndrome; hypertriglyceridemia; hypercholesterolemia; hyperglucagonemia; psoriasis; gastroesophageal reflux disease; coronary artery disease; stroke; transient ischemic attack; cognitive decline; dementia; Alzheimer's Disease; neuropathy; diabetic nephropathy; retinopathy; heart disease; diabetic heart disease; heart failure; diabetic heart failure; hirsutism; hyperandrogenism; fertility issues; menstrual dysfunction; cancer; liver cancer; ovarian cancer; breast cancer; endometrial cancer; cholangiocarcinoma; adenocarcinoma; glandular tissue tumor; stomach cancer; colorectal cancer; prostate cancer; diastolic dysfunction; hypertension; myocardial infarction; microvascular disease related to diabetes; anorexia nervosa; anorexia; a binge eating disorder; a hyperphagic state; hyperphagia; polyphagia; Prader Willi syndrome; an obesity-related genetic disorder; hypoglycemia; hypoglycemia that presents after a bariatric procedure (referred to as "post-bariatric hypoglycemia"); recurrent obesity post-bariatric surgery; recurrent metabolic disease post-bariatric surgery; iron overload conditions such as hemochromatosis types 1-4 and/or bantu siderosis; hypercholesterolemia; pancreatic cancer; short bowel syndrome; sleep apnea; arthritis; rheumatoid arthritis; general lipodystrophy (e.g. congenital, Berardinelli-Seip syndrome, acquired, and/or Lawrence syndrome); familial or acquired partial lipodystrophy (e.g. Barraquer-Simons syndrome and/or Köbberling-Dunnigan syndrome); congenital leptin deficiency; lipoprotein lipase deficiency (e.g. familial chylomicronemia syndrome, chylomicronemia, chylomicronemia syndrome, and/or hyperlipoproteinemia type Ia); Hemophilia A; Hemophilia B; Gaucher's disease; Fabry disease; Alpha-1 antitrypsin deficiency; galactosemia (e.g. type 1, 2, and/or 3); Menkes disease; Wilson's disease; microvillus inclusion disease; congenital tufting enteropathy; chronic gastroparesis; eosinophilic intestinal disease; cystic fibrosis; exocrine pancreatic insufficiency; partial pancreatectomy; Crohn's disease, inflammatory bowel disease (IBD); eosinophilic esophagitis; Celiac disease; familial apolipoprotein E deficiency; aromatase deficiency, acute pancreatitis, chronic pancreatitis, pancreatic cancer, pancreatic metastases, congenital hyperinsulinism and combinations of these. In some embodiments, system 10 is configured to treat at least two, or at least three of the above medical conditions.

As used herebelow and otherwise herein, "producing a substance X" and its derivatives shall include: producing substance X; producing an analog of substance X; producing an agonist of substance X; activating production of substance X; activation of a receptor of substance X; and/or activating downstream signaling pathways that are triggered via the activation of the receptor for substance X. Producing substance X can include constitutive production of substance X or regulated production of substance X, such as nutrient-responsive production and/or secretion of substance X.

As used herebelow and otherwise herein, "reducing a substance X" and its derivatives shall include: removing or at least reducing substance X; sequestering substance X; providing agents that counteract substance X; sequestering, reducing, or eliminating the production of substance X;

inhibiting or blocking a receptor of substance X; and/or reducing or inhibiting downstream signaling pathways influenced by a receptor of substance X.

As used herebelow and otherwise herein, the term "gene disruption" and its derivatives refer to a procedure which eliminates or at least reduces the production of functional gene products from one, both, or multiple alleles of the gene. Gene disruptions can be produced by specific targeting of a gene locus via DNA editing technologies such as CRISPR/Cas9, Zinc-finger nucleases, or TALENs, which have both DNA-binding activity that allow targeting of a specific DNA sequence or sequences as well as DNA-cleaving activity that introduces double-stranded DNA breaks that are then repaired predominantly by non-homologous end joining (NHEJ). NHEJ can lead to imprecise DNA repair whose mutations lead to effective gene disruption.

In some embodiments, the patient has Type 1 or Type 2 diabetes, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has double diabetes, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has gestational diabetes, and a treatment of the present inventive concepts can be performed to modify pancreatic tissue (e.g., pancreatic islet cells) in order to achieve one or more of the following effects: produce GLP-land/or insulin, such as constitutive and/or nutrient-responsive GLP-1 and/or insulin.

In some embodiments, the patient has hyperglycemia, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has pre-diabetes, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has monogenic diabetes, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has maturity onset diabetes of the young, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has impaired glucose tolerance, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has insulin resistance, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has hyperinsulinemia, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has hypoinsulinemia and/or relative beta cell insulin-production failure, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has non-alcoholic fatty liver disease (NAFLD) and/or non-alcoholic steatohepatitis (NASH), and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient is obese and/or has an obesity related disorder, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has polycystic ovarian syndrome (PCOS), and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has hypertriglyceridemia, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has hypercholesterolemia, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has coronary artery disease or a history of stroke and/or transient ischemic attack, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

In some embodiments, the patient has cognitive decline and/or dementia and/or Alzheimer's disease, and a treatment of the present inventive concepts can be performed to modify pancreatic tissue (e.g., pancreatic islet cells) in order to achieve one or more of the following effects: produce GLP-1 and/or insulin, such as constitutive and/or nutrient-responsive GLP-1 and/or insulin.

Material 60 can comprise one or more treatment agents, such as a treatment agent that includes cell genetic, viral and/or other material as described herein, that is mixed with a fluid, such as saline or other biocompatible fluid. In some embodiments, material 60 is mixed with a fluid comprising a volume of at least 1 μL, such as at least 5 μL, 10 μL, 15 μL and/or 20 μL. In some embodiments, material 60 is mixed with a fluid that is visualizable (e.g. includes a material that can be visualized under X-ray, MRI, and/or ultrasound visualization), as described herein.

In some embodiments, material 60 can include a chemotherapeutic agent such as gemcitabine, cisplatin, 5-fluorouracil (5-FU), Oxaliplatin, paclitaxel, capecitabine, Irinotecan, Altretamine, Cyclophosphamide, Etoposide, Ifosfamide, Liposomal doxorubicin, Melphalan Pemetrexed, Topotecan, Vinorelbine, or other chemotherapeutic agents or combinations of these.

In some embodiments, material 60 includes viral genetic material that can transduce into cells proximate to the deposit site and modifies and/or otherwise generates ("modifies" or "generates" herein) resultant tissue, such as when the deposited material 60 transduces pancreatic islet cells after deposit of material 60 into the pancreas, pancreatic duct, and/or other deposit site. Transduced islet cells are genetically modified by the viral genetic material that has been delivered.

Material 60 can be deposited at one or more deposit sites to modify and/or otherwise generate resultant tissue in one or more locations, such as when depositing material into the pancreas, pancreatic duct, and/or bile duct to transduce tissue into multiple locations within the pancreas and/or bile duct, gallbladder, and/or liver.

Depositing device 600, harvesting device 400, and/or treatment device 700 (singly or multiply, "devices 600, 400, 700") can each be configured to be introduced into the body via a natural orifice (e.g. via the mouth or rectum), or via a skin incision (e.g. in an open surgical procedure or a minimally invasive surgical procedure). Devices 600, 400, 700 can comprise one or more catheters, endoscopes, flexible probes, laparoscopic tools, syringes, and/or other flexible and/or rigid elongate devices ("catheter" or "catheters" herein). Device 600 can comprise a long (e.g. greater than 110 cm) flexible device (e.g. flexible probe or flexible syringe, "syringe" herein) that fits through a lumen, conduit, and/or other "working channel" of an access device (e.g. access device 50 described herein), such as an endoscope working channel (e.g. a working channel of less than 4.2 mm diameter, such as less than 3.8 mm or less than 3.2 mm in diameter). Device 600 can comprise a syringe that has at least one distal chamber configured to hold material 60. In some embodiments, device 600 is configured to avoid waste of material 60, such as by leaving undelivered portions of material within device 600 (e.g. not ejecting all of material 60 from device 600), and/or to avoid requiring an additional fluid and/or an undesired volume of fluid (e.g. flush material) to clear material 60 from device 600 (e.g. from one or more lumens of device 600). In some embodiments, device 600 comprises a plunger (e.g. a syringe plunger as described herein) configured to deliver (e.g. force or otherwise deliver) material 60 from the device. The plunger can comprise a plunger selected from the group consisting of: a mechanical plunger, such as a flexible plunger; a flexible plunger with stiffening capability; a hydraulic plunger, such as a plunger positioned in a distal portion of device 600 and configured to be actuated using hydraulic fluid filling a lumen of device 600; a plunger comprising a sliding element configured to separate a distal chamber (e.g. a chamber for holding material 60) from a hydraulic chamber; and combinations of these. Device 600 can be configured to be delivered (e.g. inserted into the patient) under fluoroscopic guidance. In some embodiments, device 600 comprises one or more radiopaque markers and/or a radiopaque shaft so that it can be visualized fluoroscopically. Device 600 can include at least two lumens, for example device 600 can include one lumen for receiving a syringe or plunger and one lumen for receiving contrast material and/or a guidewire. In some embodiments, device 600 can comprise a configuration of two lumens in a shape approximating a smile ("smiley lumens"), two circular lumens, and/or two D-shaped lumens. Device 600 can comprise one or more lumens configured for: receiving a vacuum, such as a desufflation lumen; delivering a contrast material; depositing or otherwise delivering material 60; receiving a guidewire; enabling pressure monitoring within the patient (e.g. by fluidly connecting an area within the patient to a pressure monitor outside the patient); enabling steering of device 600, such as by receiving a steering cable; and combinations of these. Device 600 can be configured to be delivered over a guidewire. Device 600 can include an occluding mechanism (not shown, but such as a balloon) that is positioned around a distal portion of device 600 (e.g. around a of device 600 proximal to depositing element 650) and configured to prevent or at least reduce backflow of material 60 (e.g. prevent backflow of material 60 out of the pancreas and/or pancreatic duct). Alternatively or additionally, an occluding mechanism (or other mechanism of device 600) can be configured to apply suction to a luminal wall (e.g. a full circumferential portion of a luminal wall), such as to draw the wall and the shaft of device 600 toward each other (e.g. creating a seal around device 600). In some embodiments, device 600 includes an occluding mechanism that is configured to be hydraulically activated, for example when the occluding mechanism is configured to be inflated or otherwise expanded hydraulically. The occluding mechanism can be fluidly connected to a fluid conduit of device 600. In some embodiments, the occluding mechanism is expanded via a conduit external to device 600. Device 600 can be steerable in at least one direction. Device 600 can have a torque transfer mechanism that can be configured to change the direction of steering in response to a torsional force (e.g. a force provided by a torque cable). Device 600 can have variable stiffness along its length (e.g. comprise a shaft with a stiffer proximal portion than distal portion). In some embodiments, device 600 comprises an atraumatic distal tip. Device 600 can include a chamber (e.g. not shown, such as a chamber in a distal tip or other distal portion of device 600) that is sized and arrange to allow insertion of a container that contains material 60 (e.g. a container that is also used to transport material 60), such as to simplify the process of loading device 600 with material 60. Material 60 can be loaded into device 600 in a manner similar to loading a conventional syringe, where the plunger is first fully depressed, then the tip of device 600 is placed into a container with the material 60 so that a lumen is in contact with material 60, after which the plunger is withdrawn to draw material 60 into device 600. The distal end of device 600 can be configured to attach to one or more needles, depositing element 650 shown, such as one or more needles configured to puncture tissue. Depositing element 650 can comprise a flexible needle, and/or it can comprise a needle that includes one or more flexible portions (e.g. a flexible distal portion). Depositing element 650 can comprise one or more needles that include one or more orifices for delivering the material 60, such as one or more fenestrations along the length of one or more depositing elements 650 (e.g. along the length of one or more needles) and/or an opening on the distal end of one or more depositing elements 650. The lumen of depositing element 650 can be in fluid communication with the chamber containing material 60. The lumen of the depositing element 650 can also be in fluid communication with one or more of the other lumens of device 600, such a lumen configured to deliver an imaging agent (e.g. to depositing element 650). The proximal end of device 600 can include markings that are used to indicate the location of the plunger relative to the distal end. The distal end of device 600 can have a stop that prevents the plunger from exiting the device. The proximal end of the plunger can be configured to be depressed manually, and/or it can be configured to be controlled by a component (e.g. a motor of system 10 such as via algorithm 215) that provides linear force in at least a forward direction, such as both a forward direction and a backward direction. The proximal end of device 600 can be configured to be manually steered and/or it can be configured to be robotically steered. The proximal end of device 600 can be configured to measure the pressure of fluid in the device 600 and/or the pressure proximate a deposit site (e.g. when the deposit site comprises a duct or natural body lumen), such as via a sensor-based functional element 699. The proximal end of device 600 can be configured to control pressure of the fluid within a deposit site (e.g. within a duct, for example by controlling the syringe distal-facing element). Additionally or alternatively, device 600 can be configured to monitor the pressure within the deposit site, for example via a device lumen and/or by depositing a known volume of material 60 into the deposit site. In some embodiments, system 10 is configured to measure, monitor, control, and/or limit the pressure in which material 60 is delivered to a deposit site. For example, system 10 can be configured to measure and/or control the pressure within the tissue into which material 60 is delivered (e.g. to maintain a pressure within the tissue at a maximum of 8 mmHg, such as a maximum of no more than 5, 3, or 0 mmHg). In order to prevent this pressure maximum from being exceeded, system 10 can measure, monitor and/or control a pressure within one or more components of system 10, such as within a syringe and/or within a depositing device 600, such as within a fluid pathway of a syringe and/or a device 600, whereby that measured, monitored, and/or controlled pressure can be correlated to the pressure of material 60 within the tissue (e.g. within the deposit site). In some embodiments, a second syringe can be attached to a second fluid lumen of device 600, such as a lumen configured to deliver an imaging agent, a diluent, a viscous fluid, and/or a fluid that becomes a gel within the body. The second syringe can be controlled manually and/or automatically (via processing unit 210 and/or algorithm 215)), such as is in a manner as described for the first syringe. In these embodiments, the first syringe can be configured to control the volume of material 60 delivered to the patient, while the second syringe can be used to manage the pressure of the delivered materials. In some embodiments, delivery of material 60 can be performed at an elevated pressure, such as to improve contact of material 60 (e.g. a virus) with the intended treatment site. Alternatively or additionally, system 10 can include a pressure sensor, a flow rate monitor, and/or volume sensor that produces a signal that is used by system 10 (e.g. by an algorithm 215) to regulate the amount, rate, and/or pressure of injectate (e.g. material 60) within device 600 and/or within the pancreas, pancreatic duct, and/or other deposit site. Alternatively or additionally, system 10 can include a sensor (e.g. a sensor-based functional element 699 and/or other functional element of system 10) such as a pressure sensor or impedance sensor to determine whether device 600 is in contact with a target tissue location. A sensor-based functional element 699 of device 600 and/or another sensor of system 10 can assess the pressure of an occluding element (e.g. a balloon positioned around a distal portion of device 600) to ensure adequate occlusion of the duct has occurred. An algorithm of system 10 (e.g. algorithm 215 described herein) can be configured to ensure that the material is only delivered into the pancreas and/or pancreatic duct if the pressure of the occluding element positioned around device 600 is above a threshold value (e.g. via an analysis of one or more images processed by algorithm 215, one or more pressure sensor signals, and/or other information collected by system 10).

In some embodiments, depositing device 600 comprises one or more syringes, syringe 610 shown, each comprising one or more chambers, chamber 615. Chamber 615 can hold one or more materials, such as material 60 and/or an agent (e.g. agent 70 Described herebelow). Each depositing element 650 of device 600 can be operably attached (e.g. at least fluidly attached) to at least one chamber 615 of at least one syringe 610. Each depositing element 650 can comprise one or more lumens, lumens 655 shown, extending therethrough.

In some embodiments, system 10 includes flush 64, which can comprise one, two, or more fluids configured to displace other fluids (e.g. air and/or material 60) from a lumen 655 of depositing element 650. Flush 64 can comprise saline or other materials that are relatively innocuous. In some embodiments, lumen 655 (e.g. comprising one, two, or more lumens) of depositing element 650 is filled with flush 64 prior to insertion of depositing device 600 into a patient, such as to ensure no air is present within some or all of the lumens of lumen 655. Additionally or alternatively, flush 64 can be injected into lumen 655 of depositing element 650 to deliver any remaining injectate (e.g. material 60) from the lumen and into the patient.

In some embodiments, system 10 includes an assembly for actuating (e.g. driving in one or more directions) the plunger of a syringe, syringe drive 40. Syringe drive 40 can comprise a syringe pump or other mechanism for mechanically driving a plunger through the barrel of a syringe. In some embodiments, syringe drive 40 comprises a pressure source configured to fluidly attach to a syringe to pneumatically drive a plunger through the barrel of a syringe. Various embodiments of syringe drive 40 are described herein in reference to FIGS. 17A-17E.

In some embodiments, the deposit site comprises one or more locations of the pancreas, as described herein, for example when material 60 comprises a gene therapy material configured to transduce the pancreas. In some embodiments, material 60 comprises a material (e.g. a material delivered to the anterior pararenal space) that is configured to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas. Depositing device 600 can be configured to access the pancreas through a gastrointestinal wall, such as a wall of the stomach. In these embodiments, system 10 can be configured to perform image-guided access (e.g. endoscopic ultrasound-guided access) of the pancreas, such as to aid in the delivery of material 60. Material 60 can be delivered to the pancreas at a relatively slow flow rate, as described herein.

In some embodiments, the deposit site comprises a pancreatic duct. Depositing device 600 can be constructed and arranged to remove material from the duct prior to depositing material 60. For example, device 600 can remove pancreatic enzymes from the duct prior to depositing material 60 into the duct. In some embodiments, device 600 comprises a lumen for aspirating material from the deposit site prior to the deposit. The lumen can be operably connected to a syringe, pump, or other vacuum source (e.g. a vacuum source of console 200, when console 200 is operably attached to the proximal end of device 600). In some embodiments, the vacuum is applied in a closed loop fashion, such as to control the volume of material aspirated and/or the pressure (e.g. negative pressure) to be applied to the deposit site during the aspiration. In some embodiments, the lumen used for aspiration can also be used for irrigation, such as when the lumen is also operably attached to a source of irrigation fluid. Alternatively or additionally, device 600 can comprise a separate lumen for providing irrigation. In some embodiments, irrigation fluid is provided by a computer-controlled (e.g. controlled by algorithm 215) pumping assembly of console 200.

In some embodiments, the deposit site comprises the anterior pararenal space, for example when material 60 comprises a gene therapy material configured to transduce the pancreas. In some embodiments, material 60 comprises a material (e.g. a material delivered to the anterior pararenal space) that is configured to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas. Depositing device 600 can be configured to access the anterior pararenal space via the duodenum or via the stomach of the patient. In these embodiments, system 10 can be configured to perform image-guided access (e.g. endoscopic ultrasound-guided access) of the anterior pararenal space, such as to aid in the delivery of material 60.

In some embodiments, a method of depositing material 60 into the anterior pararenal space includes positioning the patient in an orientation selected to control the flow of material 60 (e.g. after being deposited by depositing device 600) to a desired location via gravity. For example, when the patient is positioned in a prone position, material 60 that is injected into the anterior pararenal space may "pool" proximate the pancreas (which is positioned downward in the anterior pararenal space when in the prone position). Additionally or alternatively, other patient positions can be selected, for example, left lateral, right lateral, and/or supine.

In some embodiments, depositing device 600 is configured to recirculate material 60 within the anterior pararenal space. For example, device 600 can be configured to access the anterior pararenal space via two access locations, and to inject material 60 via the first location and to aspirate material 60 via the second location. System 10 can optionally be configured to recycle the aspirated material 60 and to reinject via the first location to recirculate the material 60 within the space. In some embodiments, the recirculation of material 60 is performed at a rate selected to allow transduction of material 60 while still providing a consistent flow of material 60 throughout the space.

In some embodiments, the deposit site comprises multiple sites in the anterior pararenal space, such as when one or more deposit sites are located in the peri-pancreatic space. In some embodiments, the pen-pancreatic space can be accessed by depositing device 600 using a transgastric approach, for example to access deposit sites proximate the pancreatic body and/or the pancreatic tail. Additionally or alternatively, the peri-pancreatic space can be accessed by device 600 using a trans-duodenal approach, for example to access deposit sites proximate the pancreatic head.

As used herein, "injection" shall describe an advancement of a depositing element 650 of depositing device 600 into and/or otherwise proximate a deposit site, after which material 60 in delivered into the deposit site. In some embodiments, system 10 is configured to perform an initial injection (e.g. via a depositing element 650 of depositing device 600) proximate a deposit site. This initial injection can be analyzed, such as visually by an operator of system 10 and/or in a calculated manner (e.g. algorithmically) by algorithm 215, such as by analyzing image data captured by a one or more imaging devices, imaging device shown, to confirm proper placement of device 600 (e.g. the distal portion of device 600 relative to the desired deposit site. In some embodiments, an initial injection via device 600 (e.g. of a flush material, such as a radiopaque, ultrasonically reflective, fluid including a dye, and/or other visualizable material) is configured to generate a bleb of tissue which can be visualized by imaging device 90. If this initial injection is determined to be in the proper location, material 60 can be subsequently injected into the deposit site (e.g. without repositioning device 600 between the initial injection and the subsequent injection).

In some embodiments, system 10 is configured to perform an initial aspiration (e.g. via device 600) proximate a potential deposit site. This initial aspiration can be analyzed, such as visually by an operator of system 10 and/or in an automated arrangement by system (e.g. via algorithm 215), such as to confirm that the placement of device 600 is not in a blood vessel or other undesired location. If the initial injection is determined to be not in a blood vessel or other undesired location, material 60 can be subsequently injected into the deposit site (e.g. without repositioning device 600 between the initial injection and the subsequent injection).

Devices 600, 400, 700 can each comprise a catheter configuration, such as a catheter that includes an elongate flexible shaft. The shaft can comprise an insertable length, such as a length of at least 100 cm, 130 cm, or 150 cm, respectively. In some embodiments, harvesting device 400 comprises a longer length than depositing device 600, such as when harvesting device 400 accesses the ileum (e.g. via the mouth) and depositing device 600 accesses the duodenum and/or jejunum (e.g. via the mouth). In some embodiments, harvesting device 400 comprises a shorter length than depositing device 600, such as when harvesting device 400 accesses the colon (e.g. via the rectum) and depositing device 600 accesses the duodenum and/or jejunum (e.g. via the mouth). In some embodiments, harvesting device 400 comprises a shorter length than depositing device 600, such as when harvesting device 400 accesses the duodenum (e.g. via the mouth) and depositing device 600 accesses the jejunum (e.g. via the mouth).

Devices 600, 400, 700 can be configured to be introduced into the patient: through an endoscope or other access device 50 (e.g. through a working channel of an endoscope); alongside an endoscope or other access device 50 (e.g. through a scope-attached sheath and/or over a guidewire); through a laparoscopic port or port of another access device 50; and/or via another body access device 50 described herein.

Depositing device 600 can comprise one, two, or more devices configured to deposit material 60 at a deposit site of a patient. Depositing device 600 can comprise one or more elements for depositing material 60, depositing element 650 shown (e.g. one, two, three, or more needles, as described herein). Depositing device 600 can include two or more devices that are similar and/or dissimilar (e.g. when a first depositing device 600 and a second depositing device 600 comprise dissimilar lengths, and/or dissimilar depositing elements 650). The material deposited by depositing device 600, material 60 shown in FIG. 1 and described herebelow, can include tissue 61, processed tissue (e.g. tissue 61 processed as described herein), an agent (e.g. a pharmaceutical agent or other agent 62 as described herein), and/or other material (e.g. a material configured to provide and/or support a diagnostic or therapeutic benefit). Material 60 can comprise a gene therapy material, as described herein.

Material 60 can be deposited at one, two, or more deposit sites of a patient. Deposit sites can include, but are not limited to: pancreatic duct, hepatic duct, common bile duct, cystic duct, pancreas (e.g. head, body, tail, uncinate process), anterior pararenal space, anterior/posterior and superior/inferior pancreaticoduodenal arteries, inferior pancreatic artery, dorsal pancreatic artery, the great pancreatic artery, caudal pancreatic artery, common hepatic artery, splenic artery or other arteries feeding the pancreas.

In some embodiments, depositing element 650 comprises at least two depositing elements 650*a,b*, such as at least three depositing elements 650*a,b,c*. The multiple depositing elements 650 can be configured to deposit material 60 simultaneously and/or sequentially. Depositing element 650 can comprise one, two, three, or more needles through which material 60 can be deposited at one, two, or more deposit sites. Alternatively or additionally, depositing element 650 can comprise one, two, three, or more fluid jets through which material 60 is deposited at one or more deposit sites. In some embodiments, depositing element 650 comprises one or more material 60 depositing elements 650 positioned on an expandable element, such as an inflatable balloon, a flexible basket or cage, a series of radially deployable arms, and/or an unfurlable sheet. In some embodiments, depositing device 600 is configured to lift tissue (e.g. expansion of submucosal and/or other tissue via injection into the tissue of a fluid such as a balanced salt solution such as normal saline), prior to the depositing of material 60.

In some embodiments, depositing device 600 is configured to maintain material 60 at the deposit location (e.g. prevent the migration of material 60 from the deposit site). For example, agent 70 can comprise a gel configured to be delivered by depositing device 600 on top of the delivered material 60. In some embodiments, system 10 comprises a functional element 99 comprising a sleeve configured to be placed over the material 60 (e.g. a sleeve placed in a lumen whose wall has received material 60).

In some embodiments, material 60 includes a carrier element, carrier element 63 described herein, such as an adhesive, clip, stent, tubular structure, and/or other element configured to "carry" material 60, and depositing device 600 deploys carrier element 63 (e.g. at a deposit site) to deposit material 60.

In some embodiments, depositing device 600 is configured to deposit material 60 along one or more deposit sites that collectively comprise a cumulative length of at least 25 mm. In some embodiments, material 60 is deposited at one or more deposit sites that comprise a surface with a cumulative surface area (e.g. surface area of the inner wall of one or more segments of the GI tract) of at least 50 $cm^2$, at least 100 $cm^2$, or at least 250 $cm^2$ (e.g. material 60 is deposited into one or more "patches" that cover 1% to 100% of that surface area).

In some embodiments, depositing device 600 is of similar construction and arrangement to a depositing device described in applicant's co-pending application U.S. patent application Ser. No. 16/742,645, entitled "Intestinal Catheter Device and System", filed Jan. 14, 2020, the contents of which is incorporated herein by reference in its entirety for all purposes.

In some embodiments, depositing device 600 and/or one or more depositing elements 650 can be advanced and/or retracted manually, such as by an endoscopist, nurse, or other clinician operator. Alternatively or additionally, device 600 and/or one or more depositing elements 650 can be configured to be advanced and/or retracted via a motorized controller (e.g. a controller connected to the proximal end of device 600 which can be activated by an operator). The force required to advance and/or retract device 600 and/or depositing element 650 can be monitored by system 10 (e.g. by one or more force sensor-based functional elements of device 600 or other system 10 component) during the advancement and/or retraction of depositing element 650. In some embodiments, the movement of an element 650 is stopped if the force exceeds (e.g. is above) a threshold (e.g. indicating that too much resistance has been met or that the device has malfunctioned). Additionally or alternatively, the movement can be stopped if the force is below a threshold (e.g. indicating that depositing element 650 may have entered a space such as the anterior pararenal space, a pancreatic duct, or a pancreatic vessel, and/or that the device has malfunctioned). In some embodiments, a distal portion of device 600 and/or other component of system 10 is configured to be steered (e.g. robotically steered) through a lumen of a body conduit and/or through tissue. Steering of device 600 can be performed via output of algorithm 215 (e.g. where algorithm 215 provides advancement, retraction, and/or steering instructions to a user and/or where algorithm 215 provides advancement, retraction, and/or steering control signals to a robotic mechanism of system 10). In some embodiments, algorithm 215 is configured to provide such instructions and/or control signals that cause device 600 to avoid passing through certain non-target tissue and/or other tissue to be avoided, such as ducts, arteries, and/or veins (e.g. when algorithm 215 causes device 600 to avoid these non-target tissue locations by a safety margin distance (also referred to as "safety margin" herein), such as a safety margin distance of at least 1 mm, 2 mm, or 4 mm). In some embodiments, the level (e.g. the distance) of the safety margin distance is entered into system by an operator.

In some embodiments, system 10 is configured to monitor the pressure and/or the flow rate of material 60 during a depositing step (e.g. by monitoring the change in syringe volume over time). In some embodiments, system 10 is configured to control the delivery of material 60 during a depositing step to achieve and/or maintain: a pressure of at least 3 mmHg; a pressure of no more than 25 mmHg; a flow rate of at least 0.1 mL/min, such as at least 0.3 mL/min, 0.5 mL/min, or 1 mL/min; and/or a flow rate of no more than 5 mL/min, such as no more than 2.5 mL/min or 1 mL/min. In some embodiments, depositing device 600 comprises multiple depositing elements 650 (e.g. multiple needles 6530 shown in FIG. 11B) and/or at least one single depositing element 650 comprises multiple openings (e.g. openings 6503 shown in FIG. 10). In these embodiments, the minimum and/or maximum flow rates of delivery can be increased (e.g. increased as compared to a single-opening delivery of material for example multiplied by the number of depositing elements 650 through which material 60 is being delivered. Alternatively or additionally, if depositing element 650 is moved during a depositing step (e.g. depositing element 650 is pulled back through the pancreatic tissue as material 60 is deposited), the minimum and/or maximum flow rates can be increased (e.g. increased as compared to a similar procedure in which the depositing element remains stationary during delivery of material 60). In some embodiments, system 10 can be configured to apply a small positive injection pressure to a syringe filled with a material other than material 60, after depositing element 650 is advanced into the wall of the GI tract, without causing fluid flow. For example, as depositing element 650 (e.g. an opening of element 650) travels from a high resistance space to a low resistance space (e.g. into the pararenal space), the resistance to flow will decrease and the fluid will automatically begin to flow. System 10 can be configured to monitor the change in the fluid flow rate (or pressure) and to notify the operator to stop advancing depositing element 650. Alternatively or additionally, system 10 can be configured to automatically stop advancing depositing element 650 when the change in flow rate is recognized (e.g. when depositing element 650 is being advanced under motorized control).

As described herein, depositing device 600 can be introduced into the patient via the patient's mouth. In some embodiments, depositing device 600 and an access device, access device 50 shown (e.g. a gastrointestinal endoscope comprising one or more working channels) are each introduced through the patient's mouth. In these embodiments, depositing device 600 can be introduced through a working channel of access device 50, and/or alongside access device 50.

In some embodiments, the distal end of depositing device 600 is advanced through a wall of the gastrointestinal (GI) tract and into a location proximate the pancreas, for example such that one or more depositing elements 650 are positioned for subsequent delivery of material 60 to one or more deposit sites proximate the pancreas. In these embodiments, depositing device 600 can be inserted into the patient via the mouth, either within or alongside an access device 50, as described herein.

In some embodiments, depositing device 600 comprises a needle-tipped catheter (e.g. a catheter comprising a depositing element 650 comprising a needle extending and/or extendable from the distal end of the catheter). For example, depositing element 650 can comprise a needle configured to extend from the distal end of depositing device 600. Depositing device 600 can be configured to be inserted into the patient via an image-guided device (e.g. an endoscopic ultrasound device), for example when imaging device 90 and/or access device 50 comprise an image-guided device, such as an endoscopic ultrasound device. The access device 50 can comprise a working channel (e.g. a lumen) extending therethrough, and it can be constructed and arranged to slidingly receive device 600. In some embodiments, system 10 is configured to perform endoscopic ultrasound-guided fine needle injection (EUS-FNI), such as injection of material 60 into the pancreas or other body location via an access device 50 comprising an endoscopic ultrasound device. In some embodiments, depositing element 650 comprises a needle comprising a gauge of 25, 26, 27, or greater (e.g. since gauge magnitude is inverse to diameter magnitude, a diameter of no more than that of a 25 gauge needle), such as a maximum diameter for the distal-most segment of the needle (e.g. a distal-most segment comprising a length of at least 2 cm). In some embodiments, depositing element 650 comprises a needle including one or more holes along the length of the needle (e.g. as well as at the distal end of the needle). In some embodiments, material 60 is deposited through these holes (e.g. as well as out the distal end of element 650), such that material 60 is more thoroughly diffused into the deposit site via depositing element 650.

In some embodiments, depositing device 600 comprises a reservoir configured to hold material 60 prior to injection of material 60 into the depositing site (e.g. one, two, or more deposit sites). In some embodiments, system 10 comprises a pumping mechanism configured to pump material 60 from the reservoir through depositing element 650 into the deposit site. In some embodiments, depositing device 600 comprises a syringe (e.g. as described herein) configured to hold material 60 prior to injection. In some embodiments, the syringe comprises one or more travel-limiting elements, "TLEs" herein, which are configured to limit the travel of the plunger of the syringe, such as to control the amount of material 60 delivered when the plunger is depressed (e.g. depressed until stopped by the TLE). In some embodiments, the TLEs are removable (e.g. sequentially between injections), such that multiple injections can be performed (e.g. injections at different deposit sites), and the amount of material 60 deposited during each injection is controlled by the TLEs. In some embodiments, the TLEs are configured such that each injection delivers similar amounts of material 60. Alternatively or additionally, the TLEs can be configured such that the injection volumes are different for one or more deliveries of material 60, for example when a first injection comprises a larger dose than subsequent injections. In some embodiments, the reservoir of depositing device 600 can be separate from a pneumatic or mechanical plunger system (e.g. a syringe-based system), such as to reduce dead space.

In some embodiments, depositing device 600 is configured to inject material 60 into one or more deposit sites of the pancreas and/or the anterior pararenal space via the stomach, for example when device 600 and/or an access device 50 through which device 600 is inserted comprises an endoscopic ultrasound device and/or other image-guided device, and depositing element 650 comprises a needle configured to advance through and extend from a distal portion (e.g. the distal end) of device 600. Material 60 can be delivered to one or more deposit sites of the pancreas and/or the anterior pararenal space by positioning the distal end of access device 50 and/or depositing device 600 against the stomach wall nearest to the deposit sites and advancing depositing element 650 into the deposit site. In some embodiments, depositing element 650 comprises a mechanical stop positioned to limit the advancement of the element 650 from device 600 (e.g. to limit the penetration depth of the depositing element 650). In some embodiments, the penetration depth allowed by the mechanical stop is based on the estimated thickness of the stomach wall proximate the deposit site (e.g. based on image data or a priori clinical data). In some embodiments, the penetration depth is adjustable by adjusting the location of the mechanical stop. In some embodiments, the injection angle (e.g. the angle depositing element 650 exits device 600) can be adjusted, for example: a direct injection (e.g. along the axis of device 600), a lateral injection approximately perpendicular to the axis of device 600, and/or at some angle therebetween.

In some embodiments, system 10 comprises treatment device 700. Treatment device 700 can comprise one, two, or more devices configured to ablate, remove, modify, expand, and/or otherwise treat tissue at a treatment site of a patient (e.g. a deposit site or other anatomical location of a patient). Treatment device 700 comprises one or more elements for treating tissue of the patient, treatment element 750 shown. Treatment device 700 can include two or more devices that are similar and/or dissimilar (e.g. when a first treatment device 700 and a second treatment device 700 comprise dissimilar lengths and/or dissimilar treatment elements 750). In some embodiments, treatment device 700 comprises a first treatment device 700*a* that causes tissue to necrose (e.g. via delivery of thermal energy, such as heat energy and/or cryogenic energy; electrical energy; and/or a chemical agent to tissue), and a second treatment device 700*b* that provides an abrasive force to the necrosed tissue. The second treatment device 700*b* can be used in the same clinical procedure as first treatment device 700*a* is used, or in a subsequent clinical procedure (e.g. a second clinical procedure 1, 2, or more days after the first clinical procedure). In these embodiments, tissue can be removed proximate (e.g. at and/or near) one or more deposit sites at which material 60 is to be deposited (e.g. deposited using depositing device 600).

The tissue treated by treatment device 700 can include mucosal tissue; submucosal tissue; tissue comprising at least one stem cell; tissue comprising at least one stem cell of the mucosa; tissue comprising at least one mucosal crypt containing a stem cell; and/or mucosal tissue comprising at least one stem-cell containing crypt. Tissue treated by treatment device 700 can include tissue of one or more anatomical locations selected from the group consisting of: the gastrointestinal tract; the mouth; the esophagus; the stomach; the duodenum; the jejunum; the ileum; the colon; an organ; the brain; the lungs; the liver; the bladder; the kidneys; the heart; the intestines; the skin; the peritoneal cavity; and combinations of one, two, or more of these. Tissue treated by treatment device 700 can comprise tissue that activates and/or deactivates hormonal signals and/or signaling pathways. In some embodiments, tissue treated by treatment device 700 does not include tissue of (e.g. treatment device 700 avoids adversely effecting tissue from): the lower esophageal sphincter; the pylorus; the ampulla of Vater; the ileocecal valve; and combinations of one, two, or more of these.

Treatment element 750 can comprise one, two, three, or more treatment elements configured to ablate, remove, resurface, denature, and/or otherwise effect tissue, such as mucosal tissue. Treatment element 750 can deliver an ablative fluid to treat the tissue (e.g. an ablative fluid applied directly to the tissue or delivered to a balloon placed in contact with tissue). Treatment element 750 can deliver energy to tissue, such as electrical energy; magnetic energy; chemical energy; sound energy; and/or light energy. In some embodiments, treatment element 750 comprises multiple treatment elements arranged in a circumferential pattern and/or a single element that treats a circumferential segment of tubular tissue (e.g. delivers energy and/or an agent to the full circumferential wall of a segment of intestine). The depositing of material 60 can occur before and/or after the use of treatment element 750, such as by injecting material 60 into the submucosa and subsequently performing a treatment with treatment element 750, and/or by performing a treatment with element 750 and then depositing material 60. Treating and depositing steps can be performed in the same procedure or in different procedures. These steps can be performed within minutes of one another, within 3 days, and/or within 5 days.

In some embodiments, treatment device 700 is of similar construction and arrangement to a device described in applicant's co-pending application U.S. patent application Ser. No. 16/742,645, entitled "Intestinal Catheter Device and System", filed Jan. 14, 2020, the contents of which is incorporated herein by reference in its entirety for all purposes.

As described hereabove, system 10 can further comprise one, two, or more devices configured to provide access within the patient, access device 50. Access device 50 can comprise an endoscope (e.g. an endoscopic ultrasound device), an endoscope-attached sheath, a laparoscopic port, a vascular introducer, and/or another patient access device. Access device 50 can further comprise one or more guidewires, for example one or more guidewires over which devices 600, 400, and/or 700 are introduced into the patient (e.g. and subsequently withdrawn from the patient), such as by using standard "over the wire" clinical techniques. Access device 50 can comprise a camera, such as camera and a display, such as when access device 50 comprises an endoscope including a camera. Access device 50 can comprise other imaging assemblies, such as an ultrasound imaging assembly (e.g. when access device 50 comprises an ultrasonically guided endoscope).

In some embodiments, depositing device 600 comprises access device 50, such as when access device 50 comprises an endoscope (e.g. an ultrasound-guided endoscope as described herein). For example, access device 50 can be integral to device 600, or vice versa, such as when the two components function as a single assembly (e.g. a single assembly advanced through the mouth of the patient into the stomach or small intestine).

Access device 50 can comprise one or more functional elements, functional element 99 shown. In some embodiments, functional element 99 comprise one, two, or more electrodes, and/or one, two or more ultrasound transducers, such as to deliver electrical energy (e.g. radiofrequency energy and/or electroporation energy) and/or ultrasound energy (e.g. ultrasound energy and/or sonoporation energy), respectively. In some embodiments, functional element 99 is configured to deliver electrical and/or sound energy to increase the update of material 60 through cellular walls of tissue (e.g. pancreatic tissue) into which material 60 is to be delivered. Functional element 99 can comprise one or more pressure sensors, such as one or more pressure sensors that produce a signal that is used by system 10 (e.g. via algorithm 215) to measure, monitor, and/or control the pressure in which material 60 is delivered by depositing device 600 into the patient (e.g. to limit the pressure, or any pressure increases, at the deposit site, as described herein). In some embodiments, functional element 99 comprises a source of vacuum, such as a source of vacuum configured to change (e.g. decrease) the pressure within one or more system 10 components, and/or within the patient (e.g. decrease the pressure at a deposit site of the patient and/or at a location proximate a deposit site). In some embodiments, functional element 99 comprises a fluid processing assembly configured to modify the state of material 60, such as a fluid processing assembly selected from the group consisting of: heater; chiller; centrifuge; agitator; fluid separator; and combinations of these.

System 10 can further comprise one or more devices configured to provide visualization of the patient to an operator, imaging device 90. In some embodiments, depositing device 600, access device 50, and/or another component of system 10 comprises imaging device 90 (e.g. imaging device 90 is integral to that component). Imaging device 90 can comprise an imaging device selected from the group consisting of: a camera such as an endoscopic camera; an MRI imager; a CAT scan imager; a fluoroscopic imager; an X-ray imager; an ultrasound imager such as an endoscopic or catheter-based ultrasound imager; and combinations of these. In some embodiments, material 60 comprises a radiopaque material and/or an ultrasonically reflective material, for example a material configured to be imaged by imaging device 90 when imaging device 90 comprises an X-ray or fluoroscopic imager, or an ultrasound imager, respectively. For example, material 60 can comprise a gene therapy material (e.g. a solution) including a chemical additive configured to be visible via an imaging device 90 (e.g. via X-ray imaging and/or ultrasound imaging modalities). Alternatively or additionally, material 60 can comprise a dye or other visualizable material, such as to be visualized via a camera. In some embodiments, the visualizable additive can be added to material 60 during the manufacturing of material 60 (e.g. at the time of packaging of material 60), and/or in a clinical setting (e.g. by a clinician, nurse, and/or other operator of system 10), prior to material 60 being deposited into the patient.

In some embodiments, imaging device 90 comprises an endoscopic ultrasound device configured to provide an endoscopic ultrasound (EUS) image (e.g. when access device 50 and/or depositing device 600 comprises imaging device 90). Alternatively or additionally, imaging device 90 comprises an ultrasound device and/or other imaging device configured to be positioned external to the patient's body during use (e.g. during imaging). In some embodiments, collected images (e.g. endoscopic ultrasound images) are analyzed (e.g. by algorithm 215 of system 10) and annotated to show one or more vessels or other anatomical features of interest (e.g. related to the advancement of depositing device 600 and/or other component of system 10 advanced through internal locations of the patient), such as features selected from the group consisting of: arteries, veins, the splenic vein; one or more ducts, such as the pancreatic duct; and combinations of these. Ultrasound images collected by system 10 (e.g. EUS images) can comprise multiple image types, such as standard ultrasound images and/or doppler ultrasound images. In some embodiments, collected ultrasound images (e.g. EUS images) comprise video. Analysis and annotation can be performed by system 10 in real-time (or near real-time, such as within 1 second of the image being captured, "real-time" herein). In some embodiments, system 10 enables an operator of system 10 to annotate one or more images, such as by using a pointing device (e.g. a computer mouse and/or a touch screen stylus) to identify and/or outline one or more anatomical features on a screen (e.g. a display of user interface 200 of console 200 or other display of system 10). Alternatively or additionally, an image analysis algorithm of system 10 (e.g. algorithm 215 described herein), such as a machine learning algorithm or other AI algorithm, automatically identifies and highlights these features on a screen. In some embodiments, system 10 enables the operator to correct or adjust the classification of any regions identified by the algorithm. In some embodiments, system 10 and/or the operator identifies target areas to be treated in one or more collected images (e.g. an EUS image), such as images including one, two, or more target areas to be treated, prior to performing the treatment. System 10 can be configured to document a treatment plan, such as a plan identifying particular regions to be treated. System 10 can be configured to document treatment plans for individual portions of a target area, such as the pancreas, such as for identifying one, two, or more deposits sites within the head, body, tail, and/or uncinate process of the pancreas. In some embodiments, system 10 (e.g. automatically by algorithm 215) and/or the operator (e.g. manually) can identify in the image (e.g. an EUS image) non-target areas to be avoided (e.g. avoided for delivery of material 60 and/or avoided as a pathway of introduction of depositing device 600). In some embodiments, an image analysis is performed (e.g. automatically by algorithm 215 of system 10 and/or manually by an operator) to recognize and track depositing element 650 or another portion of device 600 as it is advanced towards and/or into the tissue. In some embodiments, the operator is warned if depositing device 600 (e.g. depositing element 650) is advanced near and/or toward and/or into a non-target region, and/or beyond a target region. In some embodiments, the operator is warned if the projected path of depositing element 650 is not aimed at a target region. In some embodiments, system 10 is configured to automatically advance depositing element 650 to the target region, for example under motorized control of advancement. In some embodiments, system 10 is configured to prevent advancement (e.g. prevent automatic advancement) of depositing element 650 to a non-target region.

In some embodiments, imaging device 90 comprises a computed tomography (CT) device that is configured to provide a computed tomography (CT) image. In some embodiments, one or more CT images, and/or other images collected by system 10, are analyzed (e.g. by algorithm 215 of system 10) and annotated, such as to show one or more vessels or other anatomical features of interest, such as features selected from the group consisting of: arteries, veins, the splenic vein; one or more ducts, such as the pancreatic duct; and combinations of these. In some embodiments, collected CT or other images can comprise a series of images such as a video. Analysis and annotation can be performed in real-time (or near real-time, such as within 1 second of the image being captured). In some embodiments, system 10 enables an operator of system 10 to annotate one or more images (e.g. manually or in a semi-automated arrangement), such as by using a pointing device (e.g. a computer mouse and/or a touch screen stylus), such as to identify and/or outline one or more anatomical features on a display (e.g. a display of system 10). Alternatively or additionally, an image analysis algorithm of system 10 (e.g. algorithm 215 described herein), such as a machine learning algorithm or other AI algorithm, can automatically identify and note (e.g. highlight) these features on a display. In some embodiments, system 10 enables the operator to correct or adjust any regions identified by the algorithm (e.g. automatically identified by algorithm 215). In some embodiments, system 10 and/or the operator identifies target areas to be treated (e.g. identifies one or more deposit sites for depositing of material 60 by depositing device 600) in an image (e.g. a CT image), such as when one, two, or more target areas to be treated (e.g. one, two, or more deposit site) are identified (e.g. an noted in one or more images) prior to performing the treatment (e.g. depositing material 60). System 10 can be configured to document a treatment plan, such as a plan identifying one or more regions to be treated (e.g. identifying one or more deposit sites in which material 60 can be deposited by depositing device 600). System 10 can be configured to document (e.g. and store) treatment plans for particular deposit sites, such as for deposit sites comprising individual portions of the pancreas, such as for the head, body, tail, and/or uncinate process of the pancreas. In some embodiments, system 10 and/or the operator can identify in one or more images (e.g. CT images) one or more non-target areas in which treatment is to be avoided (e.g. material 60 is not to be deposited and/or depositing device 600 is not to travel through). In some embodiments, an image (e.g. a CT image) is captured after depositing element 650 and/or other portion of device 600 is advanced towards and/or into the tissue of the particular deposit site, such as to confirm that depositing element 650 and/or other portion of device 600 is in the right location. In some embodiments, an image analysis is performed to recognize and/or track depositing element 650 and/or other portion of deice 600 as it is advanced towards and/or into the tissue. In some embodiments, system 10 is configured to alert the operator if depositing element 650 is advanced near and/or toward a non-target region and/or to a location beyond a target region. In some embodiments, system 10 is configured to alert the operator if the projected depositing element 650 path is not aimed at (e.g. not sufficiently directed toward) a target region. In some embodiments, system 10 is configured to automatically advance depositing element 650 to the target region, for example under motorized control of advancement. In some embodiments, system 10 is configured to prevent advancement (e.g. prevent automatic advancement) of depositing element 650 to a non-target region.

In some embodiments, system 10 is configured to allow an operator to create registration data comprising data representing the location of device 600 on one or more images, such as images captured by imaging device 90. The registration data can comprise sets of data representing various locations and/or orientations of device 600 in the patient in the performance of a treatment procedure. Registration data can be collected prior to a treatment procedure, at the beginning of a treatment procedure, and/or any time throughout the treatment procedure. The registration data collected can be used to align an image (e.g. a fluoroscopic or EUS image captured just prior to a treatment procedure) with a previously defined treatment plan (e.g. a treatment plan as described herein). For example, "pre-treatment image data" comprising a set of one or more images of the patient's anatomy can be created by a first imaging device 90 (e.g. a CT imager) at a time prior to a treatment procedure (e.g. hours or days prior to a treatment procedure). A treatment plan can be created in which three to ten registration points are created in the pre-treatment image data (e.g. 3D data); the registration points representing various anatomical landmarks (e.g. branches of ducts or vessels) of the patient's anatomy. The treatment plan can also include registration points created in the pre-treatment image data that represent various locations to be treated using system 10. At the beginning of and/or during the treatment procedure, a second imaging device 90 (e.g. a fluoroscope and/or an EUS imager) can be used to create "treatment image data" representing additional images of the patient's anatomy. System 10 (via algorithm 215) can integrate the registration data of the pre-treatment image data into the treatment image data (e.g. via a registration of the two sets of image data). System 10 can be further configured to provide a display of the treatment image data to an operator of system 10, such as when the registration points are shown as an overlay on the treatment image data. The display, including the overlay, can be used by an operator to guide the treatment. In some embodiments, system 10 is configured to automatically and/or semi-automatically ("automatically" herein) guide the treatment, such as by robotic control of device 600 based on the registration data (e.g. and continuously updated images of the patient's anatomy and device 600 as provided by second imaging device 90). In some embodiments, algorithm 215 is configured to provide command signals to a robotic control portion of system 10, such as when algorithm 215 is configured to advance the distal portion of device 600 through certain tissue locations while avoiding passing through other tissue locations (e.g. avoiding ducts, arteries, and/or veins as described herein). In some embodiments, algorithm 215 is configured to avoid certain tissue locations by a safety margin distance, such as a safety margin distance of at least 1 mm, at least 2 mm, or at least 4 mm.

In some embodiments, material 60 does not include tissue 61, such as is described herebelow in reference to method 100 of FIG. 2. For example, material 60 can comprise a transgenic virus, a gene therapy material (e.g. one or more gene therapy vectors and/or one or more gene editing vectors), and/or other tissue modifying material that is applied to and/or within a deposit site. The material 60 can be delivered to a deposit site proximate to tissue that is intended to be transduced. For example, material 60 can be delivered to the pancreas and/or pancreatic duct in order to transduce pancreatic cells, including pancreatic islet cells (pancreatic islet alpha and/or beta cells) and/or pancreatic acinar (exocrine) cells. As another example, material 60 can be delivered to the hepatic duct or bile duct in order to transduce the ductal epithelium and/or the gallbladder and/or liver hepatocytes.

In some embodiments, material 60 comprises one or more agents, such as agent 62 described herein.

In some embodiments, agent 62 comprises a permeability-enhancing agent that is delivered prior to and/or simultaneous with the delivery of one or more other portions of material 60. Agent 62 can be separate from the other portions of material 60 (e.g. the therapeutic portion of material 60), and/or co-formulated with the other portions of material 60. In some embodiments, agent 62 comprises a permeability-enhancing agent that is delivered locally (e.g. to a location proximate the deposit location of other portions of material 60), and/or systemically (e.g. intravenously). In some embodiments, agent 62 comprises a permeability-enhancing agent selected from the group consisting of: hyaluronidase; collagenase; losartan; and combinations of these.

In some embodiments, agent 62 comprises a dissemination-blocking material (e.g. a polymer and/or a viscous material), such as a material that is configured to prevent undesired dissemination of material 60 to non-target locations. In these embodiments, the dissemination-blocking material can be delivered to one or more locations proximate a deposit site.

In some embodiments, agent 62 comprises a blocking element, such as an implant (e.g. a temporary and/or chronic implant) that is configured to prevent undesired dissemination of material 60 to non-target locations.

In some embodiments, material 60 includes one or more carrier elements 63, where each of which can be configured to aid in the depositing of material 60 and/or to maintain material 60 at the deposit site, such as when carrier element 63 comprises a temporary or chronic implant.

For example, carrier element 63 can comprise a deployment device, carrier **63*a*, such as a stent-like device onto which the other materials of material 60 (e.g. tissue 61 and/or a gene therapy material) is deposited, the stent-like device deployed within a lumen (e.g. the lumen of the small intestine or other body lumen) at the deposit site location. Carrier 63*a* can comprise a full or partial circumferential tubular structure, such as a structure seeded with tissue 61. Carrier 63*a*** can comprise a tubular structure comprising a hydrogel.

Alternatively or additionally, carrier element 63 can comprise an adhesive, adhesive **63*b*, such as an adhesive gel, such as an adhesive gel used to secure material 60 to the deposit site and/or to secure multiple components of material 60** together.

Alternatively or additionally, carrier element 63 can comprise a coating or wrap, coating 63*c*, such as a coating or wrap configured to prevent material 60 from migrating from the deposit site (e.g. at an undesired time). In some embodiments, carrier element 63 comprises a carrier 63*a*, and a coating 63*c* configured as a protective coating or other protecting element. In some embodiments, carrier element 63 comprises a coating 63*c* that is applied to a deposit site in one or more procedures performed after the depositing of material 60 at the deposit site (depositing of a material 60 with or without coating 63*c*), as described herebelow in reference to Step 170 of FIG. 2. In these embodiments, carrier 63*a* protects other components of material 60 (e.g. tissue 61 and/or a gene therapy material), such as to prevent undesired migration of material 60.

In some embodiments, carrier element 63 comprises a hemostatic gel. Carrier element 63 can be configured to promote engraftment of material 60 to target tissue. In some embodiments, carrier element 63 comprises a material including molecules configured to self-assemble into polymer chains in the presence of certain ions, for example a molecule such as RADA16. In some embodiments, carrier element 63 can comprise a concentration of RADA16 of approximately 0.5%, 1%, 1.25%, 2.5%, or 5%. Material 60 can also comprise saline, a sucrose solution, and/or a basal medium, such as DMEM (Dulbecco's Modified Eagle Medium). In some embodiments, carrier element 63 is applied topically (e.g. by depositing device 600 delivering carrier element 63 onto tissue), and/or it can be injected into a treatment site (e.g. injected by depositing device 600 with and/or after the depositing of material 60 by depositing device 600). Carrier element 63 can be delivered to the treatment site via the same lumen of device 600 in which material 60 is delivered, or via a separate lumen, for example to prevent premature polymerization of carrier element 63.

Agent 62 can comprise one or more pharmaceutical drugs, nutrients (e.g. hexoses, lipids, and/or amino acids), vitamins (e.g. water-soluble vitamins such as ascorbic acid), buffering agents, chemicals, fillers, and/or other agents that are included in material 60. In some embodiments, agent 62 comprises one or more agents selected from the group consisting of: antibiotic; adhesive agent such as a bioadhesive agent; a trophic agent (e.g. a growth factor or other factor used to promote wound healing); a shielding agent (e.g. an agent configured to protect one or more components of material 60 after depositing); and combinations of one, two, or more of these.

In some embodiments, one or more agents 62 are included in a process for creating material 60 at a time that is proximate the time that material 60 is deposited at a deposit site (e.g. a deposit site comprising one or more deposit sites), such as a time within 8 hours of the depositing of material 60 at a deposit site.

In some embodiments, system 10 includes one or more pharmaceutical drugs or other agents, agent 70 shown, that can be delivered to the patient prior to the depositing of material 60, and/or after the depositing of material 60, such as is described herebelow in reference to FIG. 2. Agent 70 can be delivered to the patient orally, transdermally, via an injection (e.g. a subcutaneous, intramuscular, epidural, and/or intrathecal injection); and/or intravascularly (e.g. intravenously and/or intraarterially).

In some embodiments, agent 70 comprises one or more: antibiotics; probiotics; and/or prebiotics.

In some embodiments, agent 70 comprises one or more of: an anti-inflammatory agent, a steroid, an NSAID, and/or an immunosuppressant.

In some embodiments, agent 70 comprise a tissue-disseminating agent, such as hyaluronidase collagenase, losartan, and/or the like. The tissue-disseminating agent can be injected (e.g. via depositing device 600) prior to and/or simultaneously with material 60.

In some embodiments, system 10 comprises one or more functional elements. For example, depositing device 600 can comprise one or more functional elements, functional element 699 shown. In some embodiments, system 10 comprises treatment device 700, and described herein, and treatment device 700 can comprise one or more functional elements, functional element 799 shown. In some embodiments, system 10 comprises harvesting device 400, as described herein, and harvesting device 400 can comprise one or more functional elements, functional element 499 shown. In some embodiments, system 10 comprises processing device 500, as described herein, and processing device 500 can comprise one or more functional elements, functional element 599 shown. Functional elements 499, 599, 699, and/or 799 can comprise one, two, or more sensors, transducers, and/or other functional elements as described herein. In some embodiments, functional element 699 comprises one or more valves, such as one or more valves in the various flow pathways of depositing device 600, such as valve 2356 described in reference to FIG. 22 herein. These one or more valves can be configured to prevent material 60 and/or another material present within the flow pathways of depositing device 600 from inadvertently and/or undesirably exiting device 600 (e.g. exiting device 600 and into the patient).

In some embodiments, system 10 includes diagnostic kit 81 shown, which can include one or more components configured to perform an analysis, such as an analysis to determine the potential safety and efficacy of the delivery of material 60 to a patient. Diagnostic kit 81 can include components (e.g. equipment and/or supplies) configured to perform one or more diagnostic tests on the patient to assess the physiologic response to proteins and/or peptides that would be produced by transgenic cells receiving material 60 in the body. For example, diagnostic kit 81 can assess the circulating levels of a hormone and/or deliver a therapeutic peptide and/or hormone to the patient and assess the circulating levels of that delivered therapeutic peptide and/or hormone and/or the physiologic effects of that therapeutic, such as to determine the patient's candidacy for the procedure.

In some embodiments, system 10 includes a diagnostic kit 81 which includes one or more components configured to perform an analysis, such as an analysis of one or more patients (e.g. analysis of tissue of a patient, e.g. a tissue donor patient), and/or an analysis of material 60. Diagnostic kit 81 can include components (e.g. equipment and/or supplies) configured to perform multiple tests during the creation of material 60 and/or the depositing of material 60 into a patient (e.g. a recipient of donor tissue and/or autologous tissue).

In some embodiments, diagnostic kit 81 comprises components used to perform a screening endoscopy, such as when diagnostic kit 81 comprises an endoscope. The endoscopy can be used to screen out patients with cancer, an infection, and/or other gastrointestinal pathology.

Diagnostic kit 81 can comprise one or more components configured to perform a "tissue test", such as a test to determine whether desired and/or undesired conditions of the tissue are present. In some embodiments, a sample of tissue is tested to confirm the absence of: infected tissue; undesired bacteria; endotoxins and/or other toxins; cancerous tissue; *mycoplasma*; undesired proteins (e.g. GIP, GLP-1, and/or other incretins, such as a test including a response to a glucose-based stimulus); a virus; undesired bacteria; *E. coli*; an adventitious agent; and/or other undesirable tissue characteristic. For example, this testing can be used to screen for a medical condition (e.g. disease and/or disorder) selected from the group consisting of: cancer (e.g. cancer of the GI tract); infection (e.g. an infection of the GI tract); presence of *Clostridium difficile* bacteria (*C. difficile*); HIV; Hepatitis virus A, B, and/or C; syphilis; tuberculosis; and combinations of one, two, or more of these. Alternatively or additionally, a tissue test performed using diagnostic kit 81 can comprise a test of tissue to confirm desired characteristics of the tissue are present, such as to confirm tissue is from a particular donor, and/or to confirm the presence of desired material, such as a material selected from the group consisting of: desired proteins (e.g. GIP, GLP-1, and/or other incretins, such as a test including a response to a glucose-based stimulus); immune cells; stem cells; enteroendocrine cells; a genetic sequence; an mRNA expression; cell surface antigens; and combinations of these. A tissue test comprising a donor confirmation test performed using diagnostic kit 81 can comprise a test selected from the group consisting of: DNA test; mRNA assay; proteomics assay; flow cytometry assay; immunohistochemical analysis; enzyme-linked immunosorbent assay (ELISA); and combinations thereof. In some embodiments, diagnostic kit 81 comprises components configured to perform a test for *mycoplasma* and/or virus, and the kit 81 is used to test a culture in which material 60 is expanded.

Diagnostic kit 81 can include components configured to assess a parameter related to an expansion of tissue, components configured to assess a quantity of tissue (e.g. a quantity of cells present in a sample), and/or components configured to assess a concentration and/or ratio of one or more substances in tissue. For example, during and/or after material 60 expansion (e.g. an expansion of material 60 comprising harvested tissue), diagnostic kit 81 can be configured to assess a parameter (e.g. to confirm adequate quantity and/or confirm other desired expansion parameter) selected from the group consisting of: cell growth rate; organoid growth rate; organoid density (e.g. in growth substrate); morphometry of organoids, including a quantification of the number of buds and/or crypts in the organoids; cell culture media secretions (e.g. GIP, GLP-1, insulin and/or other marker peptide not normally secreted by this cell type); and combinations of these. Diagnostic kit 81 can include components to assess a tissue parameter selected from the group consisting of: number of crypts in a tissue sample; basement membrane matrix seeding density (e.g. derived from crypt count); presence and/or concentration of immune cells; fraction of Lgr5+ cells relative to other cell types; spatial distribution of cells (e.g. distribution of cells in an organoid such as distribution of: stem cells at the ends of crypt buds; Paneth cells immediately adjacent to Lgr5+ stem cells; and differentiated cells clustered near the central cystic area of an organoid); and combinations of these.

In some embodiments, diagnostic kit 81 is configured to perform one or more tests to determine successful modification of cells. For example, diagnostic kit 81 can comprise components configured to perform a test (e.g. of material 60 comprising harvested tissue) selected from the group consisting of: PCR-based test; reporter proteins (e.g. eGFP) test; his-tagging test (e.g. of a reporter protein and/or of an otherwise functional protein of interest); antibiotic selection test (e.g. a test for resistance to puromycin); a test for modified surface/transmembrane proteins; a test for secreted peptides and/or hormones; a test of the body's potential physiologic response to material 60 on insulin resistance, beta cell function, glucose control, weight; and combinations of these.

In some embodiments, diagnostic kit 81 is configured to perform one or more tests on byproducts produced during the creation of material 60 (e.g. material 60 comprising harvested tissue), such as to avoid losing a portion of material 60 to testing. For example, diagnostic kit 81 can include components configured to perform an FACS analysis on trypsinized waste tissue, such as to determine a ratio of K cells to L cells or ratio of GIP producing cells to GLP-1 producing cells, such as to confirm identity of the donor.

In some embodiments, diagnostic kit 81 is configured to perform a test to determine safety and/or efficacy of material 60 prior to implantation into a patient. For example, diagnostic kit 81 can comprise components configured to confirm a parameter level selected from the group consisting of: endotoxin and/or other toxin levels are below a threshold; bioburden is below a threshold; *mycoplasma* level below a threshold; adventitious agent below a threshold; cell viability above a threshold, such as above a threshold of 70%; percentage of Lgr5+ cells above a threshold, such as above a threshold of 1%, or 2%, or 30%; percentage of Paneth above a threshold, such as above a threshold of 1%, or 2%, or 30%; transduction copies per cell above a threshold; potency above a threshold; and combinations of these. In some embodiments, diagnostic kit 81 can include components configured to assess potency of material 60. For example, the potency assessment can include a quantified expression of incretins and/or an expression ratio of one incretin to another (e.g. expressions that can be compared to a threshold to determine adequacy of material 60). Alternatively or additionally, the assessment can comprise a quantification of the number of cells, crypts, and/or organoids present in the sample. Diagnostic kit 81 can include components configured to provide identity information (e.g. anatomical location information) of the material 60, such as by quantifying and/or detecting markers of source tissue from cells other than enteroendocrine cells. For example, presence of fatty acid binding proteins (that are produced abundantly by enterocytes in the duodenum) would indicate duodenal tissue versus distal intestinal tissue. Diagnostic kit 81 can include components configured to perform a blood test, such as a blood test of one or more patients (e.g. a donor patient and/or a recipient patient). Blood tests of a patient can be used to evaluate that patient's suitableness for the procedure (e.g. a tissue harvesting procedure and/or a material 60 implantation procedure). Blood tests that evaluate circulating levels of hormones, presence of particular antibodies, and/or some other blood borne marker can be performed, such as to assess applicability of the patient, to perform dosimetry calculations, and/or to assess projected success of the treatment.

In some embodiments, system 10 includes safety assembly 83 shown, which can include one or more components configured to assure the safety and/or efficacy of material prior to its implantation in a patient. In some embodiments, safety assembly 83 comprises one or more components configured to confirm that tissue 61 and/or material 60 is not exposed to an undesired temperature (e.g. including at a high or low temperature for an undesired amount of time), at an undesired pressure, at an undesired force, at an undesired pH level; or at another undesired physical state, such as when safety assembly 83 comprises one or more temperature, pressure, force, pH, and/or other sensors and safety assembly 83 is configured to accompany tissue 61 during its storage and/or transportation (e.g. travel from one location to another location). For example, safety assembly 83 can comprise a color strip configured to change colors when an undesired condition is met (e.g. an undesired temperature). Safety assembly 83 can comprise a tensile force indicator, such as a string or other filament that is positioned between two containers containing tissue 61 and/or material such that breakage of the filament is indicative of an undesired force having been imparted on the containers.

Safety assembly 83 can comprise one or more components configured to destroy material 60 if an adverse condition is detected (e.g. by one or more sensors of safety assembly 83), such as to absolutely prevent material 60 from being deposited in a patient. For example, safety assembly 83 can include a portion of a tissue modification kit, tissue modification kit 86 shown, the portion including genetic material that can be included (e.g. inserted into) material 60 to cause the death of a cell when undesired (e.g. unsafe) conditions are encountered, such as is described herein.

In some embodiments, system 10 includes an identification kit, ID kit 84 shown, which can include one or more components configured to identify tissue 61 and/or material prior to the depositing of material 60 into a patient. The ID provided by ID kit 84 can be configured to travel with tissue 61 and/or material 60 during its transportation between settings, and/or during processing. ID kit 84 can provide traceability information that is compatible with clinical electronic record systems (e.g. such as through the use of unique barcodes identifying the material and/or the intended patient). ID kit 84 can provide identifiers that are applied to one or more storage containers of a storage kit, storage kit 82 shown (e.g. one or more lockable storage containers). In some embodiments, ID kit 84 can include identifiers (e.g. serial numbers or other identifiers) for one or more components of system 10 used to create material 60 and/or deposit material 60 in a patient (e.g. identifiers for harvesting device 400, processing device 500, depositing device 600, and/or treatment device 700).

In some embodiments, system 10 includes a kit for assembling material 60, deposit material assembly kit 88 shown, which can include one or more pieces of equipment, materials, containers, and/or other components configured to assemble material 60.

Deposit material assembly kit 88 can include one or more preservatives (e.g. cryopreservative), one or more antibiotics (e.g. penicillin), growth enhancers, growth inhibitors, media, and/or other materials for combining with material 60 (e.g. for storage and/or transportation). Alternatively, the additive can be introduced at locations proximate the deposit site, in a separate step from delivering material 60 (e.g. prior to, during, and/or after the delivery of material 60 to the deposit site).

In some embodiments, deposit material assembly kit 88 (and/or storage kit 82), includes a container and associated storage medium for storing a portion of material 60, portion 60', that is not to be deposited in the patient. Retention of portion 60' can be used as a "backup", in instances where a subsequent depositing of material 60 is desired.

System 10 can be configured to treat a metabolic disease and/or a pancreatic disease. In some embodiments, material 60 is delivered to one or more deposit sites comprising pancreatic deposit sites. Depositing device 600 can comprise one, two or more distally positioned depositing elements 650 (e.g. one or more needles) positioned on the distal end and/or at least a distal portion of device 600. The one, two or more depositing elements 650 can be configured to be visualized, and/or material 60 can be configured to be visualized (e.g. via ultrasound and/or fluoroscopy), such as a visualization performed just prior to, during, and/or after the delivery of material 60 to each deposit site. Depositing device 600 can be configured to be advanced to one or more deposit sites under image guidance (e.g. as provided by ultrasound imaging such as endoscopic ultrasound imaging, CT imaging, and/or MRI imaging). Depositing device 600 can be configured to deposit material 60 at one or more pancreatic deposit sites, as described herein, such as to achieve a therapeutic benefit for the patient (e.g. a benefit achieved that achieves an efficacy duration of at least 6 months), such as a therapeutic benefit provided in treating a patient afflicted with Type 1 diabetes, Type 2 diabetes, NAFLD, NASH, PCOS, obesity, pancreatitis, pancreatic cancer, and/or hyperinsulinism. The pancreatic deposit sites can include one, two, or more sites selected from the group consisting of: intra-parenchymal space; anterior pararenal space; intraductal space; intra-arterial space of an artery that feeds at least a portion of the pancreas; and combinations of these. The one or more pancreatic deposit sites can comprise locations within 10 cm, 7.5 cm, 5 cm, and/or 3 cm of a portion of the pancreas, such as when the portion of the pancreas comprises the tail, the neck, the body, the head, and/or the uncinate process of the pancreas.

In some embodiments, depositing device 600 is configured to deliver material 60 to one or more deposit sites comprising the pancreatic parenchyma. In these embodiments, a minimum volume of material 60 can be delivered into the intra-parenchymal space (e.g. in a single delivery or multiple deliveries to be performed). The minimum volume can be configured such as to cause at least a portion of the volume of material 60 to exit into the anterior pararenal space, spread, and re-enter the pancreas. The minimum volume of this material 60 delivery can comprise a volume of at least 2 mL, 3 mL, and/or 5 mL. In some embodiments, one or more additional deliveries of material 60 are also performed, such as deliveries to one or more additional deposit sites proximate the tail of the pancreas.

Depositing device 600 can be pre-loaded with material 60 (e.g. one or more treatment agents that are loaded into device 600 prior to device 600 being advanced into the patient). In some embodiments, material 60 is loaded into the distal end of depositing device 600. System 10 can be configured to allow an operator to confirm the proper location of the one or more depositing elements 650 prior to, during, and/or after the delivery of material 60 to a deposit site.

In some embodiments, depositing device 600 (e.g. via a functional element 699 comprising a heating element) and/or another component of system 10 is configured to heat tissue proximate the one or more deposit sites (e.g. one, two, or more pancreatic deposit sites), such as to heat the tissue to a temperature of at least 39° C. prior to, during, and/or after the delivery of material 60 to the one or more deposit sites.

In some embodiments, system 10 is configured to allow an operator to remove at least a portion of material 60 that has been deposited into the patient. For example, depositing device 600 and/or another component of system 10 can be configured to allow an operator to remove all or a portion of the amount of material 60 that has been previously delivered to the patient (e.g. using a functional element 699 and/or other functional element of system 10 that is configured to provide a vacuum).

Depositing device 600 can comprise materials that are configured to be sterilized, such that depositing device 600 can be sterilized prior to use (e.g. in a manufacturing process). In some embodiments, depositing device 600 comprises an insertable length (e.g. insertable into the patient's GI tract via the mouth) comprising a length between 135 cm and 210 cm, such as between 150 cm and 190 cm.

Depositing device 600 can comprise a handle, handle 601 shown. Handle 601 can be similar to positioning assembly 6050 described in reference to FIGS. 16A-16D and otherwise herein. Handle 601 can be configured to adjust the distance that depositing element 650 (e.g. one or more needles and/or fluid jets) extends beyond the distal end of depositing device 600, such as an extension distance of no more than 12 cm, such as no more than 8 cm. Handle 601 can comprise one or more adjustable locking portions that can be positioned to set the distance that depositing element 650 extends. The one or more locking portions can be temporarily affixed to handle 601, such as with one or more fixation elements such as set screws. Handle 601 can comprise one or more guide elements, such as one or more guide rails including a lip engagement portion. The guide elements can be configured to prevent depositing element 650 from being pulled out of handle 601, and/or to keep depositing element 650 from rotating. Handle 601 can comprise a conduit configured to slidingly receive at least a portion of depositing element 650, for example a stainless steel or an aluminum conduit.

Handle 601 can include one or more syringe adapters for attaching one or more syringes 610 to depositing device 600. The syringe adapters can be located at a proximal portion of handle 601. In some embodiments, one or more of the syringe adapters can comprise a luer lock adapter. The syringe adapters can include one or more one-way valves (e.g. a functional element 599 comprising one or more check valves and/or other valves) that prevent backward flow through the syringe adapter. The syringe adapters can provide haptic feedback to the operator, for example feedback that is provided when syringe 610 is properly connected.

In some embodiments, handle 601 comprises a locking mechanism that is configured to prevent translation of depositing element 650 relative to handle 601.

In some embodiments handle 601 is configured to operably attach to an access device 50, such as to an endoscope.

Handle 601 can comprise an advancement mechanism configured to advance depositing element 650, such as via rotation and/or translation of at least a portion of the advancement mechanism. The advancement mechanism can comprise a threaded channel, and a rotating member that is attached to depositing element 650 and configured to rotate within the channel. In some embodiments, the advancement mechanism is constructed and arranged to advance depositing element 650 an extension distance, such as a distance between 5 cm and 50 cm, such as between 10 cm and 20 cm.

Depositing device 600 can comprise an elongate filament, shaft 6010, which can comprise one or more lumens, lumen 6011 shown. One or more lumens 6011 of shaft 6010 can operably attach (e.g. at least fluidly attach) to depositing element 650. In some embodiments, device 600 (e.g. shaft 6010) comprises one, two, three, or more lumens. For example, device 600 can comprise a lumen 6011*a* for delivering material 60 to depositing element 650. This lumen 6011*a* can comprise an inner diameter of no less than 0.05 mm and/or it can comprise an inner diameter of no greater than 1 mm. Device 600 can comprise a lumen 6011*b* for delivering flush 64 (e.g. saline, an imaging agent such as contrast, or a polymerizing agent) to depositing element 650. This lumen 6011*b* can comprise an inner diameter of no less than 0.05 mm, and/or it can comprise an inner diameter of no greater than 1 mm. Depositing device 600 can comprise stylet 651, such as is described herein. Depositing device 600 can comprise a lumen 6011*c* for slidingly receiving stylet 651, as described herein, such as a stylet configured to stiffen device 600 and/or to prevent ingress of fluids or other materials into device 600 during advancement (e.g. advancement of depositing element 650 into tissue). In some embodiments, a lumen 6011 receives (e.g. slidingly receives) depositing element 650, for example a depositing element 650 comprising an elongate shaft and a distal needle tip. A lumen 6011 can operably attach to a vacuum source (e.g. on its proximal end), such as to provide aspiration at the distal end of depositing device 600, for example aspiration used to assess if device 600 (e.g. depositing element 650) has punctured a blood vessel. In some embodiments, device 600 uses aspiration to hold a portion of device 600 against tissue (against the stomach wall). In some embodiments, vacuum applied to a lumen 6011 prevents or at least limits tenting of tissue while depositing element 650 is inserted into tissue.

Shaft 6010 can comprise a textured outer surface configured to lower friction and/or to help prevent kinking of shaft 6010. In some embodiments, shaft 6010 comprises a cross-sectional shape including one or more projections, such as when shaft 6010 comprise a star-like shape. In some embodiments, shaft 6010 can comprise a wound coil on and/or otherwise proximate its outer surface. In some embodiments, shaft 6010 can comprise a coating, such as a coating configured to create a bumped surface. Shaft 6010 can comprise a length between 125 cm and 200 cm, such as between 140 cm and 180 cm. At least a portion of shaft 6010 can extend through at least a portion of handle 601. In some embodiments, shaft 6010 comprises a material similar to depositing element 650. In some embodiments, shaft 6010 comprises a biocompatible material such as polyether ether ketone (PEEK). In some embodiments, depositing element 650 is fixedly positioned on the distal end of shaft 6010 such that element 650 extends from the distal end of shaft 6010.

In some embodiments, shaft 6010 comprises a sheath, such as a sheath which is configured to slidingly receive depositing element 650. Shaft 6010 can comprise a lubricious or other low-friction material, for example polyoxymethylene (POM) or polytetrafluoroethylene (PTFE). In some embodiments, shaft 6010 comprises a lubricant, such as a parylene coating and/or a coating applied using vapor deposition. Shaft 6010 can comprise an outer diameter between 1.4 mm and 3.5 mm, such as between 1.8 mm and 2.2 mm. Shaft 6010 can comprise an inner diameter (i.e. the diameter of lumen 6011) between 0.25 mm and 2 mm, such as between 0.5 mm and 1 mm. Shaft 6010 can comprise a length between 130 cm and 190 cm, such as between 135 cm and 170 cm. In some embodiments, shaft 6010 is slidingly received within a lumen of an access device 50 (e.g. an endoscope). In some embodiments, handle 601 is configured to fixedly attach to the proximal portion of shaft 6010 and the proximal portion of access device 50. Handle 601 can be configured to adjust the longitudinal orientation of shaft 6010 relative to access device 50. For example, handle 601 can adjust the relative longitudinal positions (e.g. the relative position of the distal end of shaft 6010 and the distal end of access device 50) up to 8 cm. In some embodiments, handle 601 comprises a set screw that locks the relative longitudinal position of shaft 6010 and access device 50.

In some embodiments, depositing element 650 comprises a needle with a gauge between 18G and 34G, such as between 22G and 30G. Depositing element 650 can comprise a shaped distal tip (e.g. a beveled distal tip). For example, depositing element 650 can comprise an anti-coring tip shape, such as a hanging bevel, a tapered conical shape, or a side channel conical shape. Depositing element 650 can comprise a single bevel or multiple bevels. In some embodiments, the shape of the distal tip of depositing element 650 is configured to alter the path of depositing element 650 as it is inserted into tissue, for example to cause depositing element 650 to follow a curved path by causing uneven forces on depositing element 650 while interacting with the tissue. Depositing element 650 can comprise (e.g. at least the inner surface of depositing element 650 can comprise) a material selected from the group consisting of: stainless steel; nickel-titanium alloy; titanium; cobalt-chromium alloy; fused silica, polyethylene; polypropylene; polyether ether ketone (PEEK); polytetrafluoroethylene (PTFE); fluoropolymer; a sol-gel nanocomposite; a material with a hydrophobic and/or hydrophilic coating; and combinations of these. In some embodiments depositing element 650 comprises a surface that has been modified (e.g. during manufacture of depositing element 650), such as a surface modification configured to increase the visibility of depositing element 650 (e.g. via ultrasonic or X-ray imaging). For example, depositing element 650 can comprise a surface modification selected from the group consisting of: bead and/or sand blasting; laser etching; dimpling; corrugation; a coating, such as a radiopaque coating; a physical vapor deposition (PVD) coating, such as a gold PVD coating; and combinations of these. In some embodiments, depositing element 650 comprises a shape selected from the group consisting of: straight; curved; corkscrew; and combinations of these. In some embodiments, the distal diameter of depositing element 650 can be chosen to be smaller than the minimum diameter than can be visualized by an imaging device (e.g. imaging device 90), such as by endoscopic ultrasound imaging device.

As described herein, depositing device 600 can comprise an elongate tool, stylet 651. Stylet 651 can comprise a diameter that is between 0.2 mm and 0.5 mm less than the inner diameter of depositing element 650 and/or a lumen 6011. Stylet 651 can be removable from depositing device 600 (e.g. by an operator of system 10). In some embodiments, depositing device 600 and stylet 651 are configured such that the position of stylet 651 relative to device 600 can be adjusted during a clinical procedure. For example, stylet 651 can be advanced from a first position to a second position in which the tip of stylet 651 is proximate the tip of depositing element 650. In some embodiments, depositing device 600 comprises a biasing mechanism (e.g. a mechanism including a spring) configured to bias stylet 651 towards the first position when stylet 651 is advanced beyond the first position (e.g. a position where the distal end of stylet 651 is approximately 5 mm from the distal end of depositing element 650). Stylet 651 can comprise a material selected from the group consisting of: stainless steel; nickel-titanium; cobalt-chromium; and combinations of these. In some embodiments, stylet 651 comprises a gold tip.

In some embodiments, syringe 610 comprises multiple chambers, such as two or more parallel chambers or concentric chambers. In some embodiments, syringe 610 comprises a pre-filled syringe (e.g. filled in a manufacturing process, filled in a hospital pharmacy or other non-patient setting, or otherwise filled prior to the performance of the clinical procedure in which material 60 is deposited in a patient). In some embodiments, device 600 is constructed and arranged to accept a pre-filled cartridge comprising a material to be injected (e.g. material 60 or flush 64). For example, handle 601 can include a port that operably engages a pre-filled chamber such that the pre-filled material can be injected via depositing element 650. In some embodiments, syringe 610 comprises a material selected from the group consisting of: glass; plastic; stainless steel; and combinations of these.

In some embodiments, syringe drive 40 is constructed and arranged to fill and/or empty syringe 610. Syringe drive 40 can be operated in an open-loop and/or a closed-loop arrangement, for example a closed-loop arrangement based on a desired flow rate and/or pressure (e.g. a flow rate of no more than 5 mL/min, such as no more than 3 mL/min or 1 mL/min, such as when delivering material 60 to the pancreas). In some embodiments, operation of syringe drive 40 is operator controlled, such as manually via console 200. Syringe drive 40 can provide feedback (e.g. haptic feedback and/or audible feedback), such as to confirm proper engagement with syringe 610.

System 10 can be configured to maximize efficacy of the delivery of a treatment agent, material 60, to a deposit site (e.g. target tissue) of a patient, while minimizing patient risk as well as preventing or at least reducing the delivery of material 60 to undesired (e.g. off-target) tissue locations. In some embodiments, material 60 comprises at least a gene therapy material, and material 60 is delivered to the pancreas of a patient to provide a therapeutic benefit to the patient (e.g. treat a medical condition of the patient, such as insulin resistance, Type 1 diabetes, Type 2 diabetes, and/or another medical condition as described herein). System 10 can be configured to achieve a therapeutic benefit while minimizing risk of pancreatitis, and while avoiding any significant distribution of the treatment agent to non-target organs (e.g. and thus avoiding the undesired side effects that may ensue). In these embodiments, material 60 can be delivered by depositing device 600 to a minimum volume of tissue, such as to deliver to a volume of tissue selected from the group consisting of: at least 20% of the volume of the pancreas (e.g. the volume of the pancreatic tissue); at least 10% or 20% of the islet cells of the pancreas; at least 10% or 20% of the alpha cells of the pancreas; at least 10% or 20% of the beta cells of the pancreas; at least 10% or 20% of the pancreatic exocrine cells; at least 10% or 20% of the ductal epithelial cells of the pancreas; and combinations of these. In these embodiments, material 60 can be delivered by depositing device 600 to a maximum volume of tissue, such as to deliver to a volume of tissue selected from the group consisting of: at less than 60%, such as less than 50%, of the volume of the pancreas (e.g. the volume of the pancreatic tissue); less than 60%, such as less than 50%, of the islet cells of the pancreas; less than 60%, such as less than 50%, of the alpha cells of the pancreas; less than 60%, such as less than 50%, of the beta cells of the pancreas; less than 60%, such as less than 50%, of the pancreatic exocrine cells; less than 60%, such as less than 50%, of the ductal epithelial cells of the pancreas; and combinations of these. System 10 can be configured to deliver material 60 using endoscopic ultrasound (EUS) guided injection (e.g. EUS fine needle injection), such as when access device 60 comprises an endoscopic ultrasound device, and depositing device 600 is configured to be delivered to the pancreas via a working channel of the access device 600. System 10 can be configured to deliver material at a flow rate below a maximum, such as a maximum flow rate of no more than 5 mL/min, such as no more than 3 mL/min, or 1 mL/min. Depositing element 650 of depositing device 600 can comprise one or more needles, such as one or more needles with a gauge (e.g. a diameter of a distal-most segment, such as a segment of at least 2 cm) of no larger than 25, such as no larger than 27. An operator can deliver material 60 to the pancreas via multiple injections using depositing device 600, such as a number of injections that does not exceed 7 total injections, such as no more than 5, 3, or 1 total injections. The total amount of material delivered to the pancreas can comprise a volume that does not exceed 25 mL such as a total volume of no more than 15 mL. In some embodiments, the total amount of material 60 delivered to the pancreas comprises a total volume of at least 1 mL, such as a total volume of at least 5 mL. In some embodiments, the total amount of material 60 delivered to the pancreas comprises a volume between 0.010 $mL/cm^3$ and 0.6 $mL/cm^3$ relative to the volume of the pancreas. System 10 can be configured to deliver material 60 to a deposit site that comprises non-cancerous tissue, such as when material 60 is delivered by depositing to a non-cancerous portion of the pancreas. System 10 can be configured to deliver material 60 to the "normal" parenchyma. System 10 can be configured to delivery material 60, such as a material 60 comprising a gene therapy material, to the pancreas or other tissue location to treatment Type 1 diabetes, Type 2 diabetes, and/or other medical condition as described herein. In some embodiments, material 60 comprises a gene therapy material that comprises an adeno-associated virus-based (AAV-based) gene therapy material, such as when material 60 is delivered to the pancreas and/or other organ of the patient. System 10 can be configured to flush (e.g. allow an operator to flush) depositing element 650 with a small volume (e.g. a volume less than the volume of the lumen of depositing element 650) of flush material, flush 64, after delivery of material 60 into tissue (e.g. into the pancreas). Flush 64 can comprise one or more fluids with a relatively high viscosity, for example, a viscosity of at least 0.015 poise, at least 0.02 poise, or at least 0.03 poise, such as mineral oil, lipiodol, and/or other material as described herein. In some embodiments, flush 64 comprises a viscosity of no more than 0.10 poise, such as no more than 0.07 poise, or no more than 0.05 poise. As described hereabove, system 10 can be configured to deliver material 60 to the pancreas while minimizing risk of pancreatitis. For example, risk of pancreatitis for a patient can comprise a risk of no more than 5%, such as no more than 3% or 1%. As described hereabove, system 10 can be configured to limit the effects that material has on non-target organs or other non-target tissue. For example, in embodiments in which material 60 is delivered to the pancreas (e.g. to treat insulin resistance and/or diabetes as described herein), system to can be configured to have an effect on other organs (e.g. the liver, kidney, heart, gonads, brain, and/or other organ) that is less than the effect achieved in the pancreas. System 10 can be configured to deliver a tissue-disseminating agent (e.g. an agent 70 comprising a tissue-disseminating agent), such as hyaluronidase collagenase, or the like. The tissue-disseminating agent can be injected (e.g. via depositing device 600) prior to and/or simultaneously with material 60. Alternatively or additionally, material 60 can be co-formulated with a tissue-disseminating and/or a dissociating agent such as hyaluronidase, collagenase, or the like, to improve the distribution of material 60 to the pancreas.

As described herein, system 10 can comprise an access device 50 comprising a endoscopic ultrasound device, and depositing device 600 can be configured to be introduced to a tissue location such as the pancreas through a working channel of the access device 50. Depositing device 600 can include and/or can be operably attachable (e.g. at least fluidly attachable) to a reservoir, such as syringe 610 or another syringe as described herein. Material 60 (e.g. a gene therapy material and/or other treatment agent) can be included in the syringe, and/or material 60 can be drawn into the syringe by an operator. A syringe driving assembly, such as syringe drive 40 or other syringe drive as described herein, can be configured to cause the syringe and depositing element 650 of depositing device 600 to deliver material 60 into tissue (e.g. the pancreas) at a relatively slow flow rate, such as a flow rate of no more than 5 mL/min, such as no more than 3 mL/min, or 1 mL/min. Controller 200 can be configured to activate the syringe drive via a flexible drive conduit (e.g. conduit 2402 described in reference to FIG. 20B herein). In some embodiments, the flexible drive conduit comprises a length of at least 10 cm, such as to provide a minimum separation distance between at least a portion of the syringe drive (e.g. a motorized portion of the syringe drive) and the syringe containing material 60. Depositing element 650 can comprise one or more needles, and at least the inner surface of each needle (e.g. the luminal wall) can comprise a material selected from the group consisting of: stainless steel; nickel-titanium alloy; titanium; cobalt chromium; fused silica; polyethylene; polypropylene; polyether ether ketone (PEEK); polytetrafluoroethylene (PTFE); a fluoropolymer; a sol-gel nanocomposite; a material comprising a hydrophobic coating and/or a hydrophilic coating; and combinations of these. Depositing element 650 can comprise one or more needles, such as one or more needles with a gauge (e.g. a diameter of a distal-most segment, such as a segment of at least 2 cm) of no larger than 25, such as no larger than 27. In some embodiments, system 10 comprises a reservoir, such as syringe 610 or other syringe as described herein, that can be at least fluidly connected to depositing element 650 of depositing device 600, via a conduit, such as tube 2355 described in reference to FIG. 22 and otherwise herein. The reservoir and/or depositing device 600 can be configured such that when the reservoir is detached, depositing device 600, the conduit, and/or the reservoir are configured to prevent leakage of material 60 outside of internal pathways of some or all of these components. For example, depositing device 600, the conduit, and/or the reservoir can each comprises one or more valves or other sealing elements configured to prevent egress of material 60 from the associated device. In some embodiments, system 10 comprises a second syringe (e.g. such as syringe 610*a* described in reference to FIG. 9) which be configured to store and/or deliver flush material, such as flush 64 or other flush material as described herein. The flush material syringe can be configured to be removably attached to depositing element 650 of depositing device 600. In some embodiments, material 60 of system 10 comprises a gene therapy material that comprises an adeno-associated virus-based (AAV-based) gene therapy material, such as when material 60 is delivered to the pancreas and/or other organ of the patient.

In some embodiments, system 10 is configured to deliver a material 60 (e.g. a material 60 comprising an AAV-based and/or other gene therapy material) to tissue of the patient, such as to the pancreas. In these embodiments, system 10 can be configured to treat diabetes, such as Type 1 or Type 2 diabetes. Alternatively or additionally, material 60 can be delivered (e.g. to the pancreas), to treat one or more of multiple diseases affecting the pancreas. In some embodiments, material 60 comprises non-gene therapy agents. In some embodiments, delivery of material 60 be system 10 is configured to treat a medical condition selected from the group consisting of: diabetes such as Type 1 diabetes and/or Type 2 diabetes; cystic fibrosis; chronic hyperinsulinemia; chronic pancreatitis; a pancreatic cancer; and combinations of these. In some embodiments, system 10 is configured to perform endoscopic ultrasound guided injection of material 60, as described herein, into the portal vein, such as to deliver material 60 to the liver.

As described herein, system 10 can be configured to treat various medical conditions of a patient. A depositing device 600 comprising at least one depositing element 650 (e.g. at least one needle, at least one fluid jet, and/or at least one other element configured to deliver material 60 and/or other materials) can be advanced to at least one deposit site (e.g. at least one site in the pancreas) to a patient, such as a patient having a metabolic disease and/or a pancreatic disease. Material 60 can be delivered through the at least one depositing element 650 into the at least one pancreatic deposit site. In some embodiments, the at least one depositing element 650 comprises at least one needle positioned on a distal portion of the depositing device 600. In some embodiments, the distal end of depositing device 600 is delivered into the patient through the mouth, and advanced through a wall of the gastrointestinal tract to a location proximate the pancreas. In some embodiments, depositing device 600 is delivered through a working channel of an access device 50 comprising a gastrointestinal endoscope that has been delivered through the mouth of the patient. Alternatively, depositing device 600 can be delivered alongside an access device 50 comprising a gastrointestinal endoscope that has been delivered through the mouth of the patient. In some embodiments, system 10 treats a metabolic disease selected from the group consisting of: Type 1 diabetes; Type 2 diabetes; nonalcoholic fatty liver disease (NAFLD); nonalcoholic steatohepatitis (NASH); obesity; and combinations thereof. Alternatively or additionally, system 10 can treat a pancreatic disease selected from the group consisting of: pancreatitis; pancreatic cancer; hyperinsulinism; and combinations thereof. In some embodiments, the at least one pancreatic deposit site is selected from the group consisting of: intraparenchymal space; anterior pararenal space; intraductal space; intraarterial space of an artery that feeds at least a portion of the pancreas; and combinations thereof. In some embodiments, the delivering of material 60 (e.g. a treatment agent) comprises at least a first delivery in which a minimum volume of material 60 is delivered into the pancreatic parenchyma, and wherein the minimum volume of material 60 comprises a volume sufficient to cause at least a portion of the volume of material 60 to exit into the anterior pararenal space, spread, and re-enter the pancreas. At least a second delivery of material 60 to at least one additional deposit site proximate the tail of the pancreas can be performed. In some embodiments, the delivering of material 60 comprises at least a first delivery in which a minimum volume of material 60 is delivered into the pancreatic parenchyma, and wherein the minimum volume of the treatment agent comprises a volume of at least 2 ml, at least 3 ml, and/or at least 5 ml. In some embodiments, depositing device 600 is advanced to the at least one pancreatic deposit site under image guidance. The image guidance can comprise: endoscopic ultrasound guidance; computerized tomography (CT) guidance; and/or magnetic resonance imaging (MRI) guidance. In some embodiments, the at least one pancreatic deposit site comprises locations within 10 cm, 7.5 cm, 5 cm, and/or 3 cm of a portion of the pancreas, and the portion of the pancreas can comprise the tail, the neck, the body, the head, and/or the uncinate process. In some embodiments, material 60 and/or the at least one depositing element 650 is configured to be visualized by an imaging device (e.g. imaging device 90 and/or an imaging component of access device 50). Material 60 and/or the at least one depositing element 650 can be visualized with the imaging device to confirm proper delivery of material 60. In some embodiments, an imaging agent (e.g. an agent 70, agent 62, and/or other component of system 10 comprising an imaging agent) can be delivered through the at least one depositing element 650. The delivery of the imaging agent can be visualized with an imaging device (e.g. imaging device 90 and/or an imaging component of access device 50) to confirm (e.g. confirm after the delivery of at least a portion of material 60 has occurred) that a proper delivery of material 60 has occurred. In some embodiments, material 60 is pre-loaded into depositing device 600. Material 60 can be loaded into depositing device 600 from the distal end of depositing device 600. In some embodiments, system 10 is configured to deliver material 60 at a pressure of at least 3 mmHg. In some embodiments, system 10 is configured to delivery material 60 at a pressure of no more than 25 mmHg. In some embodiments, system 10 is configured to deliver material at a flow rate of at least 1 ml/min. In some embodiments, system 10 is configured to deliver material 60 at a flow rate of no more than 5 ml/min. In some embodiments, the at least one depositing element 650 comprises multiple fenestrations along its length. In some embodiments, the location (e.g. the anatomical location) of the at least one depositing element 650 is confirmed prior to delivering material 60. In some embodiments, system 10 comprises a permeability-enhancing agent (e.g. an agent 70, an agent 62, and/or another agent of system 10 comprising a permeability-enhancing agent). The permeability-enhancing agent can be delivered prior to the delivery of material 60 and/or simultaneously with the delivery material 60. System 10 can deliver the permeability-enhancing agent locally and/or intravenously. The permeability-enhancing agent can comprise an agent selected from the group consisting of: hyaluronidase; collagenase; losartan; and combinations thereof. Material can comprise a coformulation of a treatment agent and another agent, such as a permeability-enhancing agent (e.g. material 60 can comprise a coformulation comprising a gene treatment material and an agent 62 comprising a permeability-enhancing agent and/or other agent). As described herein, material 60 can comprise a gene therapy material (also referred to as a "gene therapy agent"). The gene therapy material can comprise a non-viral vector comprising a polynucleotide comprising a gene of interest. The non-viral vector can comprise a material that is selected from the group consisting of: plasmids; bacterial artificial chromosomes; yeast artificial chromosomes; minicircles; and combinations of these. The gene therapy material can comprise a viral vector comprising a polynucleotide comprising a gene of interest. The viral vector can comprise a material that is selected from the group consisting of: retrovirus vectors; adenovirus vectors; Herpes simplex virus (HSV) vectors; adeno-associated virus (AAV) vectors; and combinations of these. In some embodiments, material 60 comprises a viral vector such as an AAV vector. The AAV vector can comprise an AAV vector genome comprising a polynucleotide comprising a gene of interest. The AAV vector can further comprise an AAV capsid protein. The AAV capsid protein can comprise a capsid protein selected from the group consisting of AAV1; AAV2; AAV3; AAV4; AAV5; AAV6; AAV7; AAV8; AAV9; AAV10; AAV11; Rh10; Rh74; AAV-2i8; AAV-DJ; AAV-LK03; AAV-KP1; AAV-KP2; AAV-KP3; and variants of any of these; and combinations of these. System 10 can be configured to heat tissue proximate the at least one pancreatic deposit site, such as heating performed to heat the tissue to a temperature above 39° C. prior to, during, and/or after the delivery of material 60. System 10 can be configured to deliver a dissemination-blocking material (e.g. an agent 62, 70, and/or other agent of system 10 comprising a dissemination-blocking material) that is configured to prevent undesired dissemination of material 60 to non-target locations. The dissemination-blocking material can comprise a viscous substance and/or a polymer. System 10 can comprise a blocking element, such as when agent 62, functional element 99, and/or another component of system 10 comprises a blocking element. The blocking element (e.g. a temporary or chronic implant) can be positioned in the patient, such that the blocking element can prevent undesired dissemination of material 60 to non-target locations. In some embodiments, at least a portion of material 60 is removed from a deposit site location after the delivery of material 60 begins. In some embodiments, all, or at least a majority (e.g. greater than 50%) of the amount of material 60 delivered into the patient is removed As described herein, system 10 can be configured to deliver (e.g. endoscopically deliver) material 60 (e.g. a gene therapy agent, also referred to as gene therapy material) to an intraparenchymal space of the pancreas of a patient having a metabolic disease and/or a pancreatic disease. The delivering can comprise: advancing depositing device 600 comprising at least one depositing element 650 through the mouth and through a wall of the gastrointestinal tract to the intraparenchymal space of the pancreas. Depositing device 600 can be delivered through a working channel of an access device 50 (e.g. a gastrointestinal endoscope) that has been delivered through the mouth of the patient. Depositing device 600 can be delivered alongside an access device 50 (e.g. a gastrointestinal endoscope) that has been delivered through the mouth of the patient. Material 60 can comprise a gene therapy agent that comprises an adeno-associated virus (AAV) vector. The AAV vector can comprise: (a) an AAV capsid protein; and (b) an AAV vector genome comprising a polynucleotide comprising a gene of interest. The AAV capsid protein can comprise a capsid protein selected from the group consisting of: AAV1; AAV2; AAV3; AAV4; AAV5; AAV6; AAV7; AAV8; AAV9; AAV10; AAV11; Rh10; Rh74; AAV-2i8; AAV-DJ; AAV-LK03; AAV-KP1; AAV-KP2; and AAV-KP3; and variants of any of these; and combinations of these. The patient treated by system 10 can have Type 2 diabetes. The gene of interest described herein can encode a glucoregulatory hormone (i.e., a hormone involved in the modulation of circulating blood glucose levels). The glucoregulatory hormone can comprise a hormone selected from the group consisting of: glucagon; GLP-1; oxyntomodulin; glicentin; glicentin-related polypeptide (GRPP); major proglucagon fragment; intervening peptide 1 (IP-1); intervening peptide 2 (IP-2); GLP-2; glucose-dependent insulinotropic peptide (GIP); peptide tyrosine (PYY); Cholecystokinin (CCK); somatostatin; oxyntomodulin; Ghrelin; amylin; glucagon; leptin; follistatin; insulin-like growth factor 1 (IGF1); vasoactive intestinal peptide (VIP); growth hormone 1 (GH1); peptides, variants and fusions of any of these; and combinations of these.

Referring now to FIG. 2, a flow chart of a method for depositing material at a deposit site of a patient is illustrated, consistent with the present inventive concepts. Method 100 of FIG. 2 includes numerous optional steps, and it shall be described in reference to the use of system 10 of FIG. 1 and otherwise herein. In some embodiments, method 100 is configured to treat one, two or more medical conditions of a patient, as described herein.

In Step 110, a patient is selected, such as is described herebelow.

In Step 120, an optional step of material processing is performed to produce material 60. For example, material processing can be performed by processing device 500 to create a transgenic virus and/or other tissue modifying material, material 60, that is applied to and/or within a deposit site.

In Step 130, an optional step of performing a pre-deposit procedure, Procedure B, can be performed, such as is described herebelow.

In Step 140, material 60 is deposited at one or more deposit sites, such as is described herebelow. Material 60 can comprise one or more materials, such as those that are described in reference to FIG. 1 and otherwise herein. In some embodiments, material 60 comprises at least a gene therapy material (e.g. a gene therapy vector and/or a gene editing vector). Alternatively or additionally, material 60 can comprise a treatment agent comprising an oncolytic virus, a cell therapy, antisense oligonucleotides, aptamers, small interfering RNAs, microRNAs, and/or messenger RNAs.

In Step 150, an optional step of performing a post-deposit procedure, Procedure C, can be performed, such as is described herebelow.

In some embodiments, Step 110, selects a patient (e.g. a mammalian patient) with an HbA1c level of at least 6.5%, at least 7.0%, at least 7.5%, or at least 8%. In some embodiments, in Step 110 of method 100, a patient is selected that is obese, has a body mass index (BMI) of at least 30, has Type 2 diabetes, and has a HbA1c level above 7.0. In some embodiments, the patient is selected to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas.

In some embodiments, a patient is selected that has Type 1 diabetes, such as a patient that has stage 1 of Type 1 diabetes, whereby stage 1 is defined as the presence of p-cell autoimmunity as evidenced by the presence of two or more islet autoantibodies with normoglycemia and is presymptomatic. In some embodiments, a patient is selected that has Type 1 diabetes, such as a patient that has stage 2 of Type 1 diabetes, whereby stage 2 is defined as the presence of β-cell autoimmunity with dysglycemia and is presymptomatic. In some embodiments, a patient is selected that has Type 1 diabetes, such as a patient that has stage 3 of Type 1 diabetes, whereby stage 3 is defined as onset of symptomatic disease.

In some embodiments a patient is selected that has: cystic fibrosis; non-cystic-fibrosis; pancreatic exocrine insufficiency; chronic hyperinsulinemia; chronic pancreatitis; a pancreatic cancer; pancreatic metastases; a partial pancreatectomy; and/or another disease of the pancreas.

In some embodiments, a patient is selected that has a BMI of at least 25, 30, 35, and/or 40.

In some embodiments, a patient is selected in Step 110 that has a pancreas with a minimum level of functionality, such as when the patient has a C-Peptide level of at least 0.2, 1.0, and/or 2.0 (nM or nmol/l) and/or a fasting insulin of at least 7 μU/mL, 9 μU/mL, or 12 μU/mL.

In some embodiments, a patient is selected in Step 110 that has a relatively non-cirrhotic liver, such as when the patient has: a Fib-4 level of no more than 4; a Fib-4 level of at least 1.3, 2.0, and/or 2.5 (e.g. when the patient has NAFLD and/or NASH); an ALT level of at least 30, 35, and/or 40; an AST level of at least 25, 30, and/or 35; and combinations of one, two, or more of these.

In some embodiments, a female patient is selected in Step 110 that has impaired ovarian function, such as a patient that has oligomenorrhea (e.g. menses with a cycle of at least 35 days) and/or amenorrhea (e.g. no menses for at least 6 months). In some embodiments, a male patient is selected in Step 110 that has impaired testosterone levels and/or impaired sexual function (such as impotence).

In some embodiments, a patient is selected in Step 110 that has insulin resistance, such as when the patient has: a triglyceride/HDL ratio of at least 1.65 and/or 2.75; a HOMA-IR level of at least 2.0, 2.5, and/or 3.0; a fasting insulin of at least 5 μU/mL, 7 μU/mL, and/or 10 μU/mL; and/or a fasting glucose of at least 100 mg/dL and/or 125 mg/dL.

In some embodiments, a patient is selected in Step 110 that has liver disease, such as fatty liver disease or other liver disease diagnosed and/or prognosed via magnetic resonance (MR) imaging and/or ultrasound imaging. For example, magnetic resonance imaging can be used to determine a proton densitometry fat fraction (PDFF), also referred to as magnetic resonance fat fraction, where the patient is selected for treatment if their intra-hepatic triglyceride (IHTG) is at least 5%. Ultrasound imaging can be used to determine a hepato-renal index of echo levels (HRI), wherein the patient is selected for treatment if the HRI difference is at least 4.0 dB and/or the HRI ratio is no more than 1.0. A fibroscan (transient elastography) can be used to assess a patient for treatment. For example, a patient can be selected for treatment if their vibration controlled transient elastography is determined to be at least 6 kPa, or at least 8 kPa (e.g. when measured at 50 Hz). Alternatively or additionally, a patient can be selected for treatment if their controlled attenuation parameter (CAP), also referred to as ultrasound attenuation rate, is at least 200 dB/m or at least 250 dB/m.

In some embodiments, a patient is selected in Step 110 that has a metabolic disease, such as a metabolic disease diagnosed and/or prognosed via metabolomics. For example, a patient can be selected for treatment if their level of 2-hydroxybutyrate is no more than 5 μg/mL.

In some embodiments, a patient is selected in Step 110 that has a hormonal defect, such as a patient with insufficient GLP-1 secretions (e.g. as determined by measuring circulating levels of these).

In some embodiments, optional Procedure B of Step 130 is performed prior to depositing of material 60. In some embodiments, optional Procedure B, comprises a mucosal tissue modification procedure (e.g. an ablation, denaturing and/or removal procedure). The mucosal tissue modification procedure can comprise a tissue modification of a full or partial circumferential portion of an axial segment of a GI lumen (e.g. a duodenal or other intestinal lumen), such as an ablation procedure of the post-ampulla duodenal mucosa of at least 4 cm where the most proximal segment of the ablation is at least 1 cm distal to the ampulla of Vater.

In some embodiments, Procedure B of Step 130 comprises a procedure performed using treatment device 700 described hereabove in reference to FIG. 1. In some embodiments, treatment device 700 performs a tissue modification procedure that removes and/or causes the necrosis of tissue. In these embodiments, treatment device 700 can use thermal ablation (e.g. heat and/or cryo-based ablation), energy-based ablation, chemical ablation, and/or mechanical extraction, to remove the tissue (e.g. mucosal tissue) proximate (e.g. at and/or near) the intended deposit site for material 60. In some embodiments, system 10 is configured to allow an operator to perform a tissue modification procedure in the small intestine (e.g. in the duodenum), such as to provide a therapeutic benefit to patients with Type 1 diabetes, Type 2 diabetes, and/or insulin resistance, and the depositing of material 60 (e.g. providing a gene therapy procedure as described herein) in a different location, such as a location proximate the pancreas, such as to treat beta-cell failure. In some embodiments, the tissue modification procedure performed in Step 130 is performed in the same clinical procedure (e.g. on the same day) as the depositing of material 60 performed in Step 140. Alternatively, the tissue modification procedure performed in Step 130 can be performed at least 1 day, at least 2 days, at least 3 days, at least 1 week, at least 2 weeks, at least 4 weeks, at least 6 weeks, and/or at least 8 weeks prior to the depositing of material 60 in Step 140. In some embodiments, the tissue modification procedure performed in Step 130 is performed at least 1 day, at least 1 week, at least 1 month, at least 3 months, and/or at least 6 months after the depositing of material 60 in Step 140.

In some embodiments, a first step of Procedure B includes delivery of energy and/or an agent to tissue (e.g. by a treatment device 700 to cause the tissue to necrose), and a second step includes removing the treated tissue (e.g. by the same or a different treatment device 700, in the same or a subsequent clinical procedure).

Procedure B of Step 130 can comprise a diet undertaken by the patient, such as a diet selected from the group consisting of: a high sugar diet; a low sugar diet; a high carbohydrate diet; a low carbohydrate diet; a high fiber diet; a low fiber diet; a fast carbohydrate diet; a slow carbohydrate diet; a liquid diet; and combinations of one, two, or more of these. In some embodiments, Procedure B comprises a diet configured to change the deposit site (e.g. to change the mucosal thickness and/or other tissue property at the intended deposit site).

Procedure B of Step 130 can comprise a pharmaceutical therapy undertaken by the patient, such as a pharmaceutical therapy that is undertaken for at least 2, 4, 6, and/or 8 weeks (e.g. to assess tolerability). In some embodiments, the patient undergoes a pharmaceutical therapy to assess tolerance to exogeneous GLP-1 prior to a delivery of material 60 intended to alter (e.g. permanently alter) the patient's pancreas (as described herein).

Procedure B of Step 130 can comprise an adjustment to an existing pharmaceutical therapy, such as an adjustment comprising eliminating or at least reducing an existing pharmaceutical therapy (e.g. a reduction in insulin, GLP-1, or similar pharmaceutical), such as a reduction initiated at least 1, 2, 4, 6, and/or 8 weeks prior to delivery of material 60 (e.g. a material 60 comprising a gene therapy, such as gene therapy delivered proximate the pancreas).

Procedure B of Step 130 can comprise a diagnostic procedure, such as an endoscopic or other visualization procedure that is used to assess one or more deposit sites of the patient as it relates to safety and/or efficacy of Step 140 and/or other steps of method 100.

Procedure B can be performed at a minimum time before the depositing of material performed in Step 140. Alternatively or additionally, Procedure B of Step 130 can be performed within a maximum time of the performance of Step 140. In some embodiments, Procedure B comprises a mucosal or other tissue modification procedure, and the depositing of material 60 performed in Step 140 is performed at least 1 day, or at least 2 days after Procedure B. Alternatively or additionally, Procedure B can comprise a mucosal or other tissue modification procedure that is performed no more than 7 days before the depositing of material 60 of Step 140.

In some embodiments, material 60 is deposited in Step 140 at one, two, or more deposit sites, such as by using depositing device 600 described hereabove in reference to FIG. 1 and otherwise herein. Material 60 can be deposited at the one, two, or more deposit sites to treat one or more medical conditions of the patient, as described herein. In some embodiments, material 60 comprises multiple different materials, such as at least a first material 60*a*, and a second material 60*b*, as described herein. In these embodiments, first material 60*a* can be deposited at a first deposit site, and second material 60*b* can be deposited at a second deposit site, also as described herein.

In some embodiments, material 60 includes a component configured to aid in the depositing of material 60 and/or to maintain material 60 at the deposit site, such as is described hereabove in reference to FIG. 1.

In some embodiments, Procedure C of Step 150 comprises a mucosal or other tissue modification procedure, such as performed with treatment device 700 described hereabove in reference to FIG. 1.

In some embodiments, Procedure C of Step 150 can comprise a diet undertaken by the patient, such as a diet selected from the group consisting of: a high sugar diet; a low sugar diet; a high carbohydrate diet; a low carbohydrate diet; a high fiber diet; a low fiber diet; a fast carbohydrate diet; a slow carbohydrate diet; a liquid diet; a soft-foot diet; and combinations of one, two, or more of these. In some embodiments, Procedure B of Step 130 can also comprise the patient undergoing a diet, and the diet of Procedure C can be a different diet than that of Procedure B.

In some embodiments, the elapsed time between Step 140 and Procedure C is at least a minimum duration of time (for example, at least one month, 3 months, 6 months, and/or 12 months). In some embodiments, the elapsed time between Step 140 and Procedure C is no more than a maximum duration of time (for example, no more than one month, 3 months, 6 months, and/or 12 months).

Procedure C of Step 150 can comprise delivery of one or more agents to the patient, such as agent 70 described hereabove in reference to FIG. 1.

In some embodiments, material 60 comprises coating 63*c* described hereabove in reference to FIG. 1. In these embodiments, Procedure C can include applying coating 63*c* at a deposit site, such as a coating applied to protect other components of material 60 (e.g. tissue 61), such as to prevent undesired migration of material 60. Procedure C can include applying coating 63*c* multiple times, such as in multiple steps 170 that are performed routinely over a duration of up to 1 week, up to 4 weeks, and/or up to 12 weeks (e.g. a procedure performed repeatedly every 1 through 14 days).

In some embodiments, Procedure C comprises a diagnostic procedure, such as an endoscopic or other visualization procedure.

In some embodiments, Procedure C comprises an "augmentation procedure" configured to increase or otherwise enhance the effects on the patient of the depositing of material 60 (and/or other effects caused by the previous steps of method 100). If a desired result is obtained after depositing of material 60 at the one or more deposit sites, but a greater magnitude or duration of the effect is also desired, additional material 60 (e.g. material 60 that had been stored) can be deposited (e.g. using depositing device 600) proximate the deposit site to cause the augmentation (e.g. after the deposit site tissue is removed or at least modified, such as via an ablation or other tissue modifying procedure performed using treatment device 700). The deposit performed in Procedure C can include depositing material over the entirety of the earlier deposit site, over a partial segment of the earlier deposit site, and/or over a different area than the earlier deposit site.

In some embodiments, system 10 and the methods of the present inventive concepts are configured to treat one, two or more medical conditions of a patient, such as Type 1 diabetes, Type 2 diabetes, and/or other medical condition, such as are described hereabove in reference to FIG. 1.

System 10 and the methods of the present inventive concepts can be configured to treat at least two medical conditions, such as Type 2 diabetes and NAFLD; Type 2 diabetes and hypertension; Type 2 diabetes and hypertriglyceridemia; Type 2 diabetes and iron overload; NALFD and iron overload; NASH and iron overload; or Type 2 diabetes and NASH.

In some embodiments, method 100 is performed to treat at least Type 1 diabetes, Type 2 diabetes and/or obesity, such as to treat both Type 2 diabetes and obesity. For example, in Step 110, a patient is selected, such as a patient with two, three, or more of the following characteristics: obesity; Type 2 diabetes; body mass index of at least 30; and/or an HbA1c of at least 7. In Step 130, a procedure is performed prior to depositing of material 60, Procedure B described herein, such as a mucosal tissue modification procedure (e.g. an ablation, denaturing and/or removal procedure). The mucosal tissue modification procedure can comprise a tissue modification of a full or partial circumferential portion of an axial segment of a GI lumen (e.g. a duodenal or other intestinal lumen), such as an ablation procedure of the post-ampulla duodenal mucosa of at least 4 cm where the most proximal segment of the ablation is at least 1 cm distal to the ampulla of Vater. In Step 140, material 60 is deposited in one or more deposit sites (e.g. deposit sites in the pancreas and/or pancreatic duct(s) of the patient) with device 600. The depositing can occur in the same clinical procedure in which Procedure B is performed, prior to the performance of Procedure B, and/or in a subsequent clinical procedure performed on a later day. In some embodiments, the depositing step and Procedure B are separated in time by at least two weeks, at least three months, and/or at least 6 months. Material 60 can be deposited in one or more locations in the pancreas, as described herein. Alternatively or additionally, material 60 can be deposited along the length of the pancreatic ducts and/or at the common pancreatic duct. Intraductal delivery can be performed to cause material 60 to travel in a retrograde direction through the ductal tree and/or otherwise travel to achieve paracellular delivery to reach pancreatic cells outside of the duct. Step 150 can be performed, comprising Procedure C. Procedure C can include one, two, or more of: restricted food intake for a minimum time period (e.g. an elemental diet for approximately 48 hours); a pureed diet for a minimum time period (e.g. at least 2 weeks); and/or intake of one or more NSAID or anti-inflammatory agent.

Step 140 can include, after a delivery of material 60 to the deposit site (e.g. one, two, or more deposit sites), the evacuation of at least a portion of the volume of material 60 that remains within the lumen of depositing element 650 from which material 60 is delivered. The evacuation can be performed by delivery of flushing material, such as flush 64 described herein, into the lumen of the associated depositing element 650. If multiple material 60 deliveries are made (e.g. to multiple deposit sites), this evacuation procedure can be performed after the delivery at the final deposit site. The flush 64 (e.g. a sterile, viscous, biocompatible fluid) can comprise one or more materials selected from the group consisting of: mineral oil; ethiodized oil; a contrast agent; phosphate buffered saline; lipiodol; a gas, such as CO2 or atmospheric air; and combinations of these. The volume of the flush 64 introduced into the lumen of the associated depositing element 650 can comprise at least 50% of the volume of the lumen of the depositing element 650, and/or no more than 100%, 90%, 80% and/or 75% of the volume of the lumen of the depositing element 650. The volume of flush 64 introduced into the lumen of the depositing element 650 can comprise a volume of no more than 250 μL. Flush 64 can be introduced into the lumen of the depositing element 650 in a manner configured to avoid mixing of the flush 64 with the material 60 already present in the lumen of the depositing element 650. In some embodiments, flush 64 can comprise a fluid with a density different than material 60, such as to prevent and/or at least limit mixing of the two. For example, flush 64 can comprise an oil, such as sterile mineral oil, or a gas, such as CO2 or atmospheric air. In some embodiments, flush 64 comprises a density between 0.75 g/cm$^3$ and 0.95 g/cm$^3$ such as between 0.8 g/cm$^3$ and 0.9 g/cm$^3$ or a density between 1.1 g/cm$^3$ and 4.5 g/cm$^3$.

Each component of system 10 that is advanced into the patient during the performance of method 100 can be removed at an appropriate time after its use.

Figure 3:
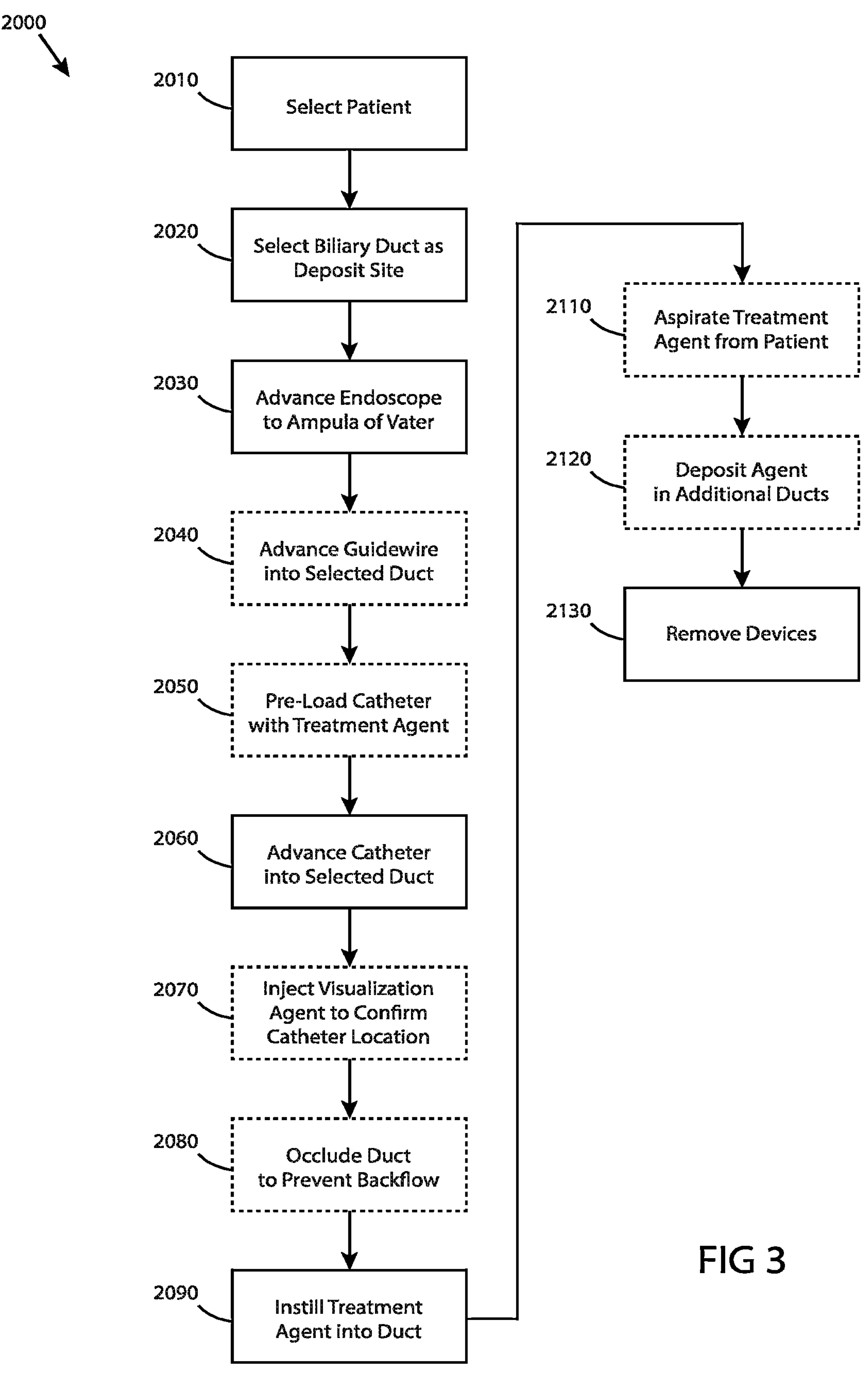
FIG. 3 illustrates a flow chart of another method for depositing material at a deposit site of a patient, consistent with the present inventive concepts.

Referring now to FIG. 3, a flow chart of another method for depositing material at a deposit site of a patient is illustrated, consistent with the present inventive concepts. Method 2000 of FIG. 3 includes numerous optional steps, and it is described in reference to the use of system 10 of FIG. 1 and otherwise herein. In some embodiments, method 2000 is configured to treat one, two or more medical conditions, such as are described herein.

In Step 2010, a patient is selected. In some embodiments, the patient is selected to receive gene therapy of the pancreas. In some embodiments, the patient is selected to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas.

In some embodiments, in Step 2010 a patient is selected (e.g. a mammalian patient) with an HbA1c level of at least 6.5%, at least 7.0%, at least 7.5%, or at least 8%. In some embodiments, in Step 2010, a patient is selected that is obese, has a body mass index (BMI) of at least 30, has Type 2 diabetes, and has a HbA1c level above 7.0.

In some embodiments, a patient is selected that has Type 1 diabetes, such as a patient that has stage 1 of Type 1 diabetes, whereby stage 1 is defined as the presence of D-cell autoimmunity as evidenced by the presence of two or more islet autoantibodies with normoglycemia and is presymptomatic. In some embodiments, a patient is selected that has Type 1 diabetes, such as a patient that has stage 2 of Type 1 diabetes, whereby stage 2 is defined as the presence of β-cell autoimmunity with dysglycemia and is presymptomatic. In some embodiments, a patient is selected that has Type 1 diabetes, such as a patient that has stage 3 of Type 1 diabetes, whereby stage 3 is defined as onset of symptomatic disease.

In some embodiments a patient is selected that has: cystic fibrosis; non-cystic-fibrosis; pancreatic exocrine insufficiency; chronic hyperinsulinemia; chronic pancreatitis; a pancreatic cancer; pancreatic metastases; a partial pancreatectomy; and/or another disease of the pancreas.

In some embodiments, a patient is selected in Step 2010 that has a BMI of at least 30, 35, and/or 40.

In some embodiments, a patient is selected in Step 2010 that has a pancreas with a minimum level of functionality, such as when the patient has a C-Peptide level of at least 0.2, 1.0, and/or 2.0 (nM or nmol/l) and/or a fasting insulin of at least 7 μU/mL, 9 μU/mL, or 12 μU/mL. Alternatively or additionally, a patient is selected in Step 2010 with a C-Peptide level of less than 0.6, 0.8, 1.0, and/or 2.0 (nM or nmol/l) and/or a fasting insulin of less than 12 μU/mL, 14 μU/mL, or 16 μU/mL.

In some embodiments, a patient is selected in Step 2010 that has a relatively non-cirrhotic liver, such as when the patient has: a Fib-4 level of no more than 4; a Fib-4 level of at least 1.3, 2.0, and/or 2.5 (e.g. when the patient has NAFLD and/or NASH); an ALT level of at least 30, 35, and/or 40; an AST level of at least 25, 30, and/or 35; a creatinine clearance rate of greater than at least 40 mL/min; a serum creatinine level of no more than 1.5 mg/dL; a urine volume of at least 500 mL/day; a urine sodium level of at least 10 mEq/L; absence of portal hypertension; absence of ascites; and combinations of one, two, or more of these.

In some embodiments, a female patient is selected in Step 2010 that has impaired ovarian function, such as a patient that has oligomenorrhea (e.g. menses with a cycle of at least 35 days) and/or amenorrhea (e.g. no menses for at least 6 months). In some embodiments, a male patient is selected in Step 2010 that has impaired testosterone levels and/or impaired sexual function (such as impotence).

In some embodiments, a patient is selected in Step 2010 that has insulin resistance, such as when the patient has: a triglyceride/HDL ratio of at least 1.65 and/or 2.75; a HOMA-IR level of at least 2.0, 2.5, and/or 3.0; a fasting insulin of at least 5 μU/mL, 7 μU/mL, and/or 10 μU/mL; and/or a fasting glucose of at least 100 mg/dL and/or 125 mg/dL.

In some embodiments, a patient is selected in Step 2010 that has liver disease, such as fatty liver disease or other liver disease diagnosed and/or prognosed via magnetic resonance (MR) imaging and/or ultrasound imaging. For example, magnetic resonance imaging can be used to determine a proton densitometry fat fraction (PDFF), also referred to as magnetic resonance fat fraction, where the patient is selected for treatment if their intra-hepatic triglyceride (IHTG) is at least 5%. Ultrasound imaging can be used to determine a hepato-renal index of echo levels (HRI), wherein the patient is selected for treatment if the HRI difference is at least 4.0 dB and/or the HRI ratio is no more than 1.0. A fibroscan (transient elastography) can be used to assess a patient for treatment. For example, a patient can be selected for treatment if their vibration controlled transient elastography is determined to be at least 6 kPa, or at least 8 kPa (e.g. when measured at 50 Hz). Alternatively or additionally, a patient can be selected for treatment if their controlled attenuation parameter (CAP), also referred to as ultrasound attenuation rate, is at least 200 dB/m or at least 250 dB/m.

In some embodiments, a patient is selected in Step 2010 that has a metabolic disease, such as a metabolic disease diagnosed and/or prognosed via metabolomics. For example, a patient can be selected for treatment if their level of 2-hydroxybutyrate is no more than 5 μg/mL.

In some embodiments, a patient is selected in Step 2010 that has post-bariatric hypoglycemia. For example, a post-bariatric surgery patient can be selected: if a post-prandial blood sugar level is determined by system 10 to be below 70 mg/dL, 60 mg/dL, and/or 50 mg/dL; if the patient has known hypoglycemia unawareness; and/or if the patient has documented history of severe hypoglycemia, such as one or more hypoglycemic events requiring third party assistance.

In some embodiments, a patient is selected in Step 2010 that has a hormonal defect, such as a patient with insufficient GLP-1 secretions (e.g. as determined by measuring circulating levels of these).

In Step 2020, a duct of the biliary tree is selected as a deposit site, such as when the deposit site comprises the pancreatic duct, cystic duct, common bile duct, right hepatic duct, left hepatic duct, and/or common hepatic duct.

In Step 2030, an endoscope, such as a duodenoscope, is advanced to ampulla of Vater.

In Step 2040, an optional step of advancing a guidewire through the endoscope into the selected duct using fluoroscopic guidance can be performed.

In Step 2050, an optional step is performed of pre-loading depositing device 600 (e.g. a catheter device) with the treatment agent, material 60. In some embodiments, the distal end of depositing device 600 is pre-loaded with material 60.

In Step 2060, depositing device 60 (e.g. a catheter with a lumen extending therethrough) is advanced through the endoscope into the selected duct. If a guidewire was placed in the duct in the previous step 2050, then device 600 can be advanced over the guidewire.

In Step 2070, an optional step can be performed of injecting a visualization agent into the duct to confirm proper depositing device 600 location. The visualization agent can comprise saline, fluoroscopic contrast, $CO_2$, and/or another agent visible via an imaging device, such as imaging device 90 described herein. If device 600 is not in the desired location, it can be re-positioned (e.g. and reconfirmed). If this confirmatory step is performed, a sub-step of aspirating the visualization agent can then optionally be performed prior to continuing.

In Step 2080, the selected duct can be occluded in a region proximal to the distal end of depositing device 600, while leaving the lumen of device 600 open, such as to prevent unwanted backflow around the outside of device 600. Optionally a visualizable occlusion element, as described herein, can be deployed and visualized by fluoroscopic imaging to ensure appropriate location and function.

In Step 2090, the treatment agent, material 60, (e.g. a gene therapy material, chemotherapy agent, saline, anti-pancreatitis agent, and/or other treatment agent as described in reference to FIG. 1 and otherwise herein) is instilled through the lumen of depositing device 600, under image guidance, and into the selected duct, such as while maintaining pressure within the tissue at or below a desired level, as described herebelow. In some embodiments, material 60 comprises a treatment agent comprising an oncolytic virus, a cell therapy, antisense oligonucleotides, aptamers, small interfering RNAs, microRNAs, and/or messenger RNAs. A volume of at least 2 mL, 5 mL, or 10 mL of material 60 can be instilled. Material 60 can be designed to be visualized by imaging device 90 (e.g. when material 60 is mixed with ultrasound contrast and/or fluoroscopic contrast materials). The instillation step can optionally include dwelling for some period of time without instilling additional material (e.g. a time period of at least 5, 10, 15, 20, and/or 30 min). In some embodiments, system can be configured to prevent each delivery of material 60 from exceeding a maximum volume of material 60 delivery, such as a maximum volume of no more than 2.5 mL, no more than 5.0 mL, and/or no more than 10.0 mL.

In some embodiments, of Step 2090, pressure within the tissue can be maintained at or below interstitial pressure (e.g. at or below 0, 3, 5, and/or 8 mmHg) such as by adding and/or withdrawing fluid through depositing device 600 (fluid such as material 60, a visualization agent, saline, and/or other diluent), or optionally by using a computer-controlled device (e.g. a pumping assembly of console 200) attached to the proximal end of device 600. In this configuration, the maximum pressure achieved can be maintained below interstitial pressure, or the pressure control can be pulsatile such that the average pressure remains below interstitial pressure. In some embodiments, system 10 is configured to maintain the pressure of delivery of material 60 to a level of no more than 25 mmHg.

In another embodiment of Step 2090, pressure within the tissue can be maintained above interstitial pressure (e.g. above 0, 3, 5, and/or 8 mmHg) and at or below capillary pressure (e.g. at or above 15, 20, and/or 25 mmHg), such as by adding and/or withdrawing fluid through depositing device 600 (fluid such as material 60, a visualization agent, saline, and/or other diluent), or optionally by using a computer-controlled device (e.g. a pumping assembly of console 200) attached to the proximal end of device 600. In this configuration, the maximum pressure can be maintained below capillary pressure, or pressure control can be pulsatile so that average pressure remains below capillary pressure. In some embodiments, system 10 is configured to maintain the pressure of the material 60 to a level of at least 3 mmHg.

In some embodiments of Step 2090, pressure can be increased by instilling material through device 600 until acinarization is visualized (e.g. as seen on fluoroscopy), then maintaining that same pressure within a tight range, such as within a pressure range of +/−3 mmHg or +/−5 mmHg.

In Step 2110, an optional step can be performed of aspirating a significant portion of material 60 from the patient (e.g. aspirating at least 30%, 50%, and/or 70% of the injected volume).

In Step 2120, an optional step of depositing one or more treatment agents (e.g. material 60) in additional ducts can be performed, for example as follows. Device 600 and guidewire (if present) can be withdrawn from the selected duct. A second duct can be identified, and device 600 can be repositioned into the second duct in the same way as was performed for the first duct. Additional treatment agent, material 60, is delivered, maintaining pressure in the same manner that was performed for the previous injection. Cumulative volume injected can be at least 5 mL or 10 mL or 20 mL or 40 mL. The total number of injections can be less than 5, 7, 10 or 12 injections. In some embodiments, the total number of injections is at least 2, 3, 4 or 5 injections. After delivery of material 60 to a deposit site, at least a portion of the material 60 that remains within the lumen of the depositing element 650 can be evacuated from the lumen (e.g. into the patient at the deposit site), such as via introduction of a flushing material into the lumen (e.g. as described hereinabove in reference to FIG. 2). This optional evacuation step can be performed after the final delivery of material (e.g. after the injection at the last deposit site).

In Step 2130, depositing device 600 and guidewire (if present) are withdrawn into the endoscope and the procedure is completed as per a standard interventional endoscopic procedure. Appropriate devices are then removed from the patient.

Figure 4:
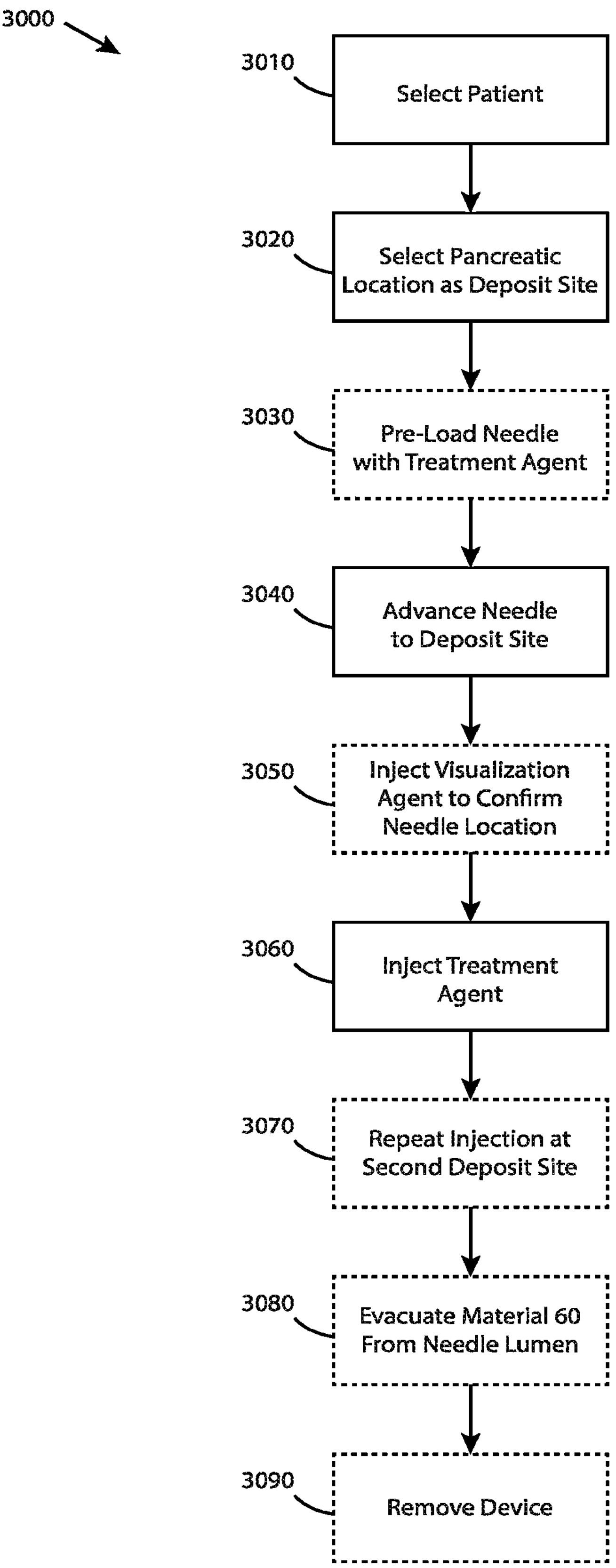
FIG. 4 illustrates a flow chart of another method for depositing material at a deposit site of a patient, consistent with the present inventive concepts.

Referring now to FIG. 4, a flow chart of another method for depositing material at a deposit site of a patient is illustrated, consistent with the present inventive concepts. Method 3000 of FIG. 4 includes numerous optional steps, and it is described in reference to the use of system 10 of FIG. 1 and otherwise herein. In some embodiments, method 3000 is configured to treat one, two or more medical conditions of a patient as described herein.

In Step 3010, a patient is selected. In some embodiments, the patient is selected to receive gene therapy of the pancreas. In some embodiments, the patient is selected to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas.

In some embodiments, in Step 3010 a patient is selected (e.g. a mammalian patient) with an HbA1c level of at least 6.5%, at least 7.0%, at least 7.5%, or at least 8%. In some embodiments, in Step 3010, a patient is selected that is obese, has a body mass index (BMI) of at least 30, has Type 2 diabetes, and has a HbA1c level above 7.0.

In some embodiments, a patient is selected that has Type 1 diabetes, such as a patient that has stage 1 of Type 1 diabetes, whereby stage 1 is defined as the presence of P-cell autoimmunity as evidenced by the presence of two or more islet autoantibodies with normoglycemia and is presymptomatic. In some embodiments, a patient is selected that has Type 1 diabetes, such as a patient that has stage 2 of Type 1 diabetes, whereby stage 2 is defined as the presence of β-cell autoimmunity with dysglycemia and is presymptomatic. In some embodiments, a patient is selected that has Type 1 diabetes, such as a patient that has stage 3 of Type 1 diabetes, whereby stage 3 is defined as onset of symptomatic disease.

In some embodiments a patient is selected that has: cystic fibrosis; non-cystic-fibrosis; pancreatic exocrine insufficiency; chronic hyperinsulinemia; chronic pancreatitis; a pancreatic cancer; pancreatic metastases; a partial pancreatectomy; and/or another disease of the pancreas.

In some embodiments, a patient is selected in Step 3010 that has a BMI of at least 30, 35, and/or 40.

In some embodiments, a patient is selected in Step 3010 that has a pancreas with a minimum level of functionality, such as when the patient has a C-Peptide level of at least 0.2, 1.0, and/or 2.0 (nM or nmol/l) and/or a fasting insulin of at least 7 μU/mL, 9 μU/mL, or 12 μU/mL. Alternatively or additionally, a patient is selected in Step 3010 with a C-Peptide level of less than 0.6, 0.8, 1.0, and/or 2.0 (nM or nmol/l) and/or a fasting insulin of less than 12 μU/mL, 14 μU/mL, or 16 μU/mL.

In some embodiments, a patient is selected in Step 3010 that has a relatively non-cirrhotic liver, such as when the patient has: a Fib-4 level of no more than 4; a Fib-4 level of at least 1.3, 2.0, and/or 2.5 (e.g. when the patient has NAFLD and/or NASH); an ALT level of at least 30, 35, and/or 40; an AST level of at least 25, 30, and/or 35; and combinations of one, two, or more of these.

In some embodiments, a female patient is selected in Step 3010 that has impaired ovarian function, such as a patient that has oligomenorrhea (e.g. menses with a cycle of at least 35 days) and/or amenorrhea (e.g. no menses for at least 6 months). In some embodiments, a male patient is selected in Step 3010 that has impaired testosterone levels and/or impaired sexual function (such as impotence).

In some embodiments, a patient is selected in Step 3010 that has insulin resistance, such as when the patient has: a triglyceride/HDL ratio of at least 1.65 and/or 2.75; a HOMA-IR level of at least 2.0, 2.5, and/or 3.0; a fasting insulin of at least 5 μU/mL, 7 μU/mL, and/or 10 μU/mL; and/or a fasting glucose of at least 100 mg/dL and/or 125 mg/dL.

In some embodiments, a patient is selected in Step 3010 that has liver disease, such as fatty liver disease or other liver disease diagnosed and/or prognosed via magnetic resonance (MR) imaging and/or ultrasound imaging. For example, magnetic resonance imaging can be used to determine a proton densitometry fat fraction (PDFF), also referred to as magnetic resonance fat fraction, where the patient is selected for treatment if their intra-hepatic triglyceride (IHTG) is at least 5%. Ultrasound imaging can be used to determine a hepato-renal index of echo levels (HRI), wherein the patient is selected for treatment if the HRI difference is at least 4.0 dB and/or the HRI ratio is no more than 1.0. A fibroscan (transient elastography) can be used to assess a patient for treatment. For example, a patient can be selected for treatment if their vibration controlled transient elastography is determined to be at least 6 kPa, or at least 8 kPa (e.g. when measured at 50 Hz). Alternatively or additionally, a patient can be selected for treatment if their controlled attenuation parameter (CAP), also referred to as ultrasound attenuation rate, is at least 200 dB/m or at least 250 dB/m.

In some embodiments, a patient is selected in Step 3010 that has a metabolic disease, such as a metabolic disease diagnosed and/or prognosed via metabolomics. For example, a patient can be selected for treatment if their level of 2-hydroxybutyrate is no more than 5 μg/mL.

In some embodiments, a patient is selected in Step 3010 that has post-bariatric hypoglycemia. For example, a post-bariatric surgery patient can be selected: if a post-prandial blood sugar level is determined by system 10 to be below 70 mg/dL, 60 mg/dL, and/or 50 mg/dL; if the patient has known hypoglycemia unawareness; and/or if the patient has documented history of severe hypoglycemia, such as one or more hypoglycemic events requiring third party assistance.

In some embodiments, a patient is selected in Step 3010 that has a hormonal defect, such as a patient with insufficient GLP-1 secretions (e.g. as determined by measuring circulating levels of these).

In Step 3020, one, two, or more locations within the pancreas is selected as a deposit site, such as one, two, or more locations within the head, body, tail, and/or uncinate process of the pancreas, and that location can be visualized by imaging such as endoscopic ultrasound (EUS), ultrasound, MRI, fluoroscopy, and/or computed tomography. Alternatively or additionally, a deposit site can be selected from the group consisting of: anterior, posterior, superior, and/or inferior pancreaticoduodenal arteries; inferior pancreatic artery; dorsal pancreatic artery; the great pancreatic artery; caudal pancreatic artery; common hepatic artery; splenic artery; other arteries feeding the pancreas; and combinations of these. The deposit site can be selected by visualizing the pancreas (e.g. with an EUS-based imaging device 90 and/or other imaging device of system 10), and selecting a deposit site that avoids ducts, arteries, and/or veins (e.g. avoids all of these). In some embodiments, an imaging device 90 is configured to perform doppler ultrasound imaging, such as doppler imaging that is used to identify locations of arteries and/or veins.

In Step 3030, an optional step is performed of pre-loading depositing element 650 of depositing device 600 with material 60. In some embodiments, the distal end of depositing element 650 is pre-loaded with material 60. In some embodiments, the dead space (e.g. internal volume) within depositing element 650 is sufficiently small such that pre-loading of depositing element 650 with material 60 is not performed prior to placing depositing element 650 in the pancreas.

In Step 3040, depositing element 650 is advanced into the selected pancreatic location under image guidance, without crossing a duct, artery or vein. This image-guided depositing device 650 placement can comprise one or more of: EUS-guided needle placement, CT-guided needle placement, and the like. If an EUS-guided placement is performed, the endoscope is first placed in the proper position in the stomach or duodenum, and depositing element 650 is advanced through the endoscope, through the wall of the stomach or duodenum, and into the pancreas to the desired treatment location.

In Step 3050, an optional step can be performed of injecting a visualization agent into the pancreas to confirm proper depositing device 600 location. The visualization agent can comprise saline, fluoroscopic contrast, $CO_2$, and/or another agent visible via an imaging device. such as imaging device 90 described herein. If depositing element 650 is not in the desired location, it can be re-positioned. If this confirmatory step is performed, a sub-step of aspirating the visualization agent can then optionally be performed prior to continuing.

In Step 3060, material 60 (e.g. a gene therapy material such as a gene therapy vector and/or a gene editing vector, chemotherapy agent, saline, anti-pancreatitis agent, and/or other treatment agent) is injected via depositing element 650 into the pancreas, under image guidance, while maintaining pressure at or below a desired level, as described herebelow. In some embodiments, material 60 comprises a treatment agent comprising an oncolytic virus, a cell therapy, antisense oligonucleotides, aptamers, small interfering RNAs, microRNAs, and/or messenger RNAs. The injected volume in this location can be at least 0.5 mL, 1 mL, or 2 mL. In some embodiments, the injected volume is sufficiently large such that some of material 60 escapes from the pancreas into the anterior pararenal space. In some embodiments, system 10 can be configured to prevent each delivery of material 60 from exceeding a maximum volume of material 60 delivery, such as a maximum volume of no more than 2.5 mL, no more than 5.0 mL, and/or no more than 10.0 mL. Material 60 can comprise a liquid, powder, and/or a biodegradable polymer designed to elute a treatment agent (e.g. a pharmaceutical) over a time period, such as at least 1 hour, 2 hours, 3 hours, 1 week, 2 weeks, 4 weeks, and/or 8 weeks. Material 60 can be configured to be visualized by imaging device 90 (e.g. mixed with ultrasound contrast and/or fluoroscopic contrast agent). In some embodiments, a tissue-disseminating agent, such as hyaluronidase collagenase, or the like, is injected (e.g. via depositing device 600) prior to and/or simultaneously with material 60. Alternatively or additionally, material 60 can be co-formulated with a tissue-disseminating and/or a dissociating agent such as hyaluronidase, collagenase, or the like, to improve the distribution of material 60 to the pancreas.

In some embodiments of Step 3060, pressure within the tissue can be maintained at or below interstitial pressure (e.g. at or below 0, 3, 5, and/or 8 mmHg), such as by adding and/or withdrawing fluid through the depositing device 600 (fluid such as material 60, a visualization agent, saline, and/or other diluent), or optionally by using a computer-controlled device (e.g. a pumping assembly of console 200) attached to the proximal end of device 600. In this configuration, the maximum pressure can be maintained below interstitial pressure, or the pressure control can be pulsatile so that the average pressure remains below interstitial pressure.

In some embodiments of Step 3060, pressure within the tissue can be maintained above interstitial pressure (e.g. above 0, 3, 5, and/or 8 mmHg) and at or below capillary pressure (e.g. at or below 15, 20, or 25 mmHg), such as by adding and/or withdrawing fluid through depositing device 600 (fluid such as material 60, visualization agent, saline, and/or other diluent), or optionally by using a computer-controlled device (e.g. a pumping assembly of console 200) attached to the proximal end of device 600. In this configuration, the maximum pressure can be maintained below capillary pressure, or pressure control can be pulsatile so that average pressure remains below capillary pressure. In some embodiments, Step 3060 can include controlling the flow rate of delivery, such as to control the flow rate to a rate of at least 0.1 mL/min, such as at least 0.3 mL/min, 0.5 mL/min, or 1 mL/min; and/or a flow rate of no more than 5 mL/min, such as no more than 2.5 mL/min or 1 mL/min.

In Step 3070, an optional step of withdrawing depositing element 650 from the pancreas, identifying a second pancreatic location for injection, and repeating the injection steps can be performed. The second pancreatic deposit site can be selected based on the avoidance of certain body locations and/or structures, such as to avoid ducts, arteries, and/or veins (e.g. as described hereabove in reference to the selection of the first deposit site in Step 3020). In some embodiments, multiple injections in additional locations can be performed in the same or a different manner. In some embodiments, a first injection is performed, after which depositing element 650 is partially withdrawn, then re-oriented, and then advanced to a second location in which a second injection is performed. The selected locations can be within the same portion of the pancreas (i.e. the head, body, tail, and/or uncinate process), or the locations can cover two or more portions of the pancreas. Spacing between deposit site locations for injection can be at least 0.5 cm, 1 cm, and/or 2 cm. Cumulative volume injected across all injections can be at least 5 mL, 10 mL, 20 mL, and/or 40 mL. The total number of injections can be at least 2, 5, 10, or 20 injections. In some embodiments, the total number of injections is at least 2, 3, 4 or 5 injections. In some embodiments, no more than 7 injections are performed, such as no more than 5, 3, and/or 1 injection are performed in the delivery of material 60 (e.g. to the pancreas or other tissue of the patient). In some embodiments, advancement of one or more depositing elements 650 (e.g. one or more needles) is along a trajectory to the target site, that avoids one or more anatomical locations of the patient, such as avoidance targets selected from the group consisting of: an artery; a vein; a chamber; a nerve; a duct; and combinations of these.

In some embodiments, optional Step 3080 is performed in which at least a portion of material 60 present within the lumen of the depositing element 650 after performance of Step 3060 is evacuated from the lumen (e.g. into the patient at a deposit site) via introduction of a flushing material into the lumen, such as is described hereinabove in reference to FIG. 2. Optional Step 3080 can be performed after the final delivery of material 60 (e.g. after the injection at the last deposit site).

After all material 60 deliveries are performed, appropriate devices are removed from the patient in Step 3090.

Figure 5:
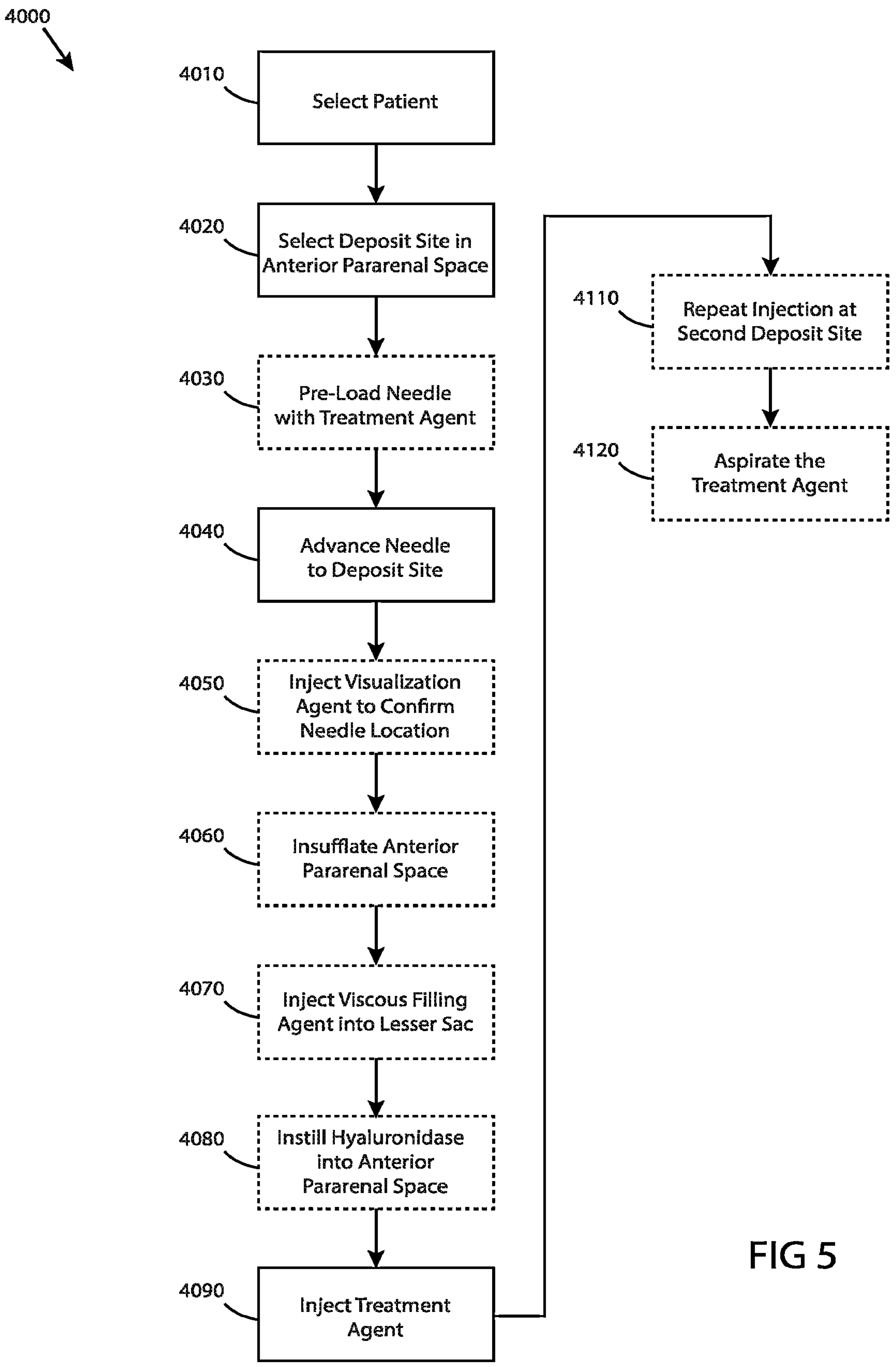
FIG. 5 illustrates a flow chart of another method for depositing material at a deposit site of a patient, consistent with the present inventive concepts.

Referring now to FIG. 5, a flow chart of another method for depositing material at a deposit site of a patient is illustrated, consistent with the present inventive concepts. Method 4000 of FIG. 5 includes numerous optional steps, and it is described in reference to the use of system 10 of FIG. 1 and otherwise herein. In some embodiments, method 4000 is configured to treat one, two or more medical conditions of a patient as described herein.

In Step 4010, a patient is selected. In some embodiments, the patient is selected to receive gene therapy of the pancreas. In some embodiments, the patient is selected to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas.

In some embodiments, in Step 4010 a patient is selected (e.g. a mammalian patient) with an HbA1c level of at least 6.5%, at least 7.0%, at least 7.5%, or at least 8%. In some embodiments, in Step 4010, a patient is selected that is obese, has a body mass index (BMI) of at least 30, has Type 2 diabetes, and has a HbA1c level above 7.0.

In some embodiments, a patient is selected that has Type 1 diabetes, such as a patient that has stage 1 of Type 1 diabetes, whereby stage 1 is defined as the presence of D-cell autoimmunity as evidenced by the presence of two or more islet autoantibodies with normoglycemia and is presymptomatic. In some embodiments, a patient is selected that has Type 1 diabetes, such as a patient that has stage 2 of Type 1 diabetes, whereby stage 2 is defined as the presence of β-cell autoimmunity with dysglycemia and is presymptomatic. In some embodiments, a patient is selected that has Type 1 diabetes, such as a patient that has stage 3 of Type 1 diabetes, whereby stage 3 is defined as onset of symptomatic disease.

In some embodiments a patient is selected that has: cystic fibrosis; non-cystic-fibrosis; pancreatic exocrine insufficiency; chronic hyperinsulinemia; chronic pancreatitis; a pancreatic cancer; pancreatic metastases; a partial pancreatectomy; and/or another disease of the pancreas.

In some embodiments, a patient is selected in Step 4010 that has a BMI of at least 30, 35, and/or 40.

In some embodiments, a patient is selected in Step 4010 that has a pancreas with a minimum level of functionality, such as when the patient has a C-Peptide level of at least 0.2, 1.0, and/or 2.0 (nM or nmol/l) and/or a fasting insulin of at least 7 μU/mL, 9 μU/mL, or 12 μU/mL. Alternatively or additionally, a patient is selected in Step 4010 with a C-Peptide level of less than 0.6, 0.8, 1.0, and/or 2.0 (nM or nmol/l) and/or a fasting insulin of less than 12 μU/mL, 14 μU/mL, or 16 μU/mL.

In some embodiments, a patient is selected in Step 4010 that has a relatively non-cirrhotic liver, such as when the patient has: a Fib-4 level of no more than 4; a Fib-4 level of at least 1.3, 2.0, and/or 2.5 (e.g. when the patient has NAFLD and/or NASH); an ALT level of at least 30, 35, and/or 40; an AST level of at least 25, 30, and/or 35; and combinations of one, two, or more of these.

In some embodiments, a female patient is selected in Step 4010 that has impaired ovarian function, such as a patient that has oligomenorrhea (e.g. menses with a cycle of at least 35 days) and/or amenorrhea (e.g. no menses for at least 6 months). In some embodiments, a male patient is selected in Step 4010 that has impaired testosterone levels and/or impaired sexual function (such as impotence).

In some embodiments, a patient is selected in Step 4010 that has insulin resistance, such as when the patient has: a triglyceride/HDL ratio of at least 1.65 and/or 2.75; a HOMA-IR level of at least 2.0, 2.5, and/or 3.0; a fasting insulin of at least 5 μU/mL, 7 μU/mL, and/or 10 μU/mL; and/or a fasting glucose of at least 100 mg/dL and/or 125 mg/dL.

In some embodiments, a patient is selected in Step 4010 that has liver disease, such as fatty liver disease or other liver disease diagnosed and/or prognosed via magnetic resonance (MR) imaging and/or ultrasound imaging. For example, magnetic resonance imaging can be used to determine a proton densitometry fat fraction (PDFF), also referred to as magnetic resonance fat fraction, where the patient is selected for treatment if their intra-hepatic triglyceride (IHTG) is at least 5%. Ultrasound imaging can be used to determine a hepato-renal index of echo levels (HRI), wherein the patient is selected for treatment if the HRI difference is at least 4.0 dB and/or the HRI ratio is no more than 1.0. A fibroscan (transient elastography) can be used to assess a patient for treatment. For example, a patient can be selected for treatment if their vibration controlled transient elastography is determined to be at least 6 kPa, or at least 8 kPa (e.g. when measured at 50 Hz). Alternatively or additionally, a patient can be selected for treatment if their controlled attenuation parameter (CAP), also referred to as ultrasound attenuation rate, is at least 200 dB/m or at least 250 dB/m.

In some embodiments, a patient is selected in Step 4010 that has a metabolic disease, such as a metabolic disease diagnosed and/or prognosed via metabolomics. For example, a patient can be selected for treatment if their level of 2-hydroxybutyrate is no more than 5 μg/mL.

In some embodiments, a patient is selected in Step 4010 that has post-bariatric hypoglycemia. For example, a post-bariatric surgery patient can be selected: if a post-prandial blood sugar level is determined by system 10 to be below 70 mg/dL, 60 mg/dL, and/or 50 mg/dL; if the patient has known hypoglycemia unawareness; and/or if the patient has documented history of severe hypoglycemia, such as one or more hypoglycemic events requiring third party assistance.

In some embodiments, a patient is selected in Step 4010 that has a hormonal defect, such as a patient with insufficient GLP-1 secretions (e.g. as determined by measuring circulating levels of these).

In Step 4020, a location in the anterior pararenal space (e.g. adjacent to the head, body, tail, and/or uncinate process of the pancreas) is selected as a deposit site, and that location is visualized by imaging such as endoscopic ultrasound (EUS), ultrasound, MRI, fluoroscopy, and/or computed tomography.

In Step 4030, an optional step is performed of pre-loading depositing element 650 of depositing device 600 with material 60. In some embodiments, the distal end of depositing element 650 is pre-loaded with material 60.

In Step 4040, depositing element 650 is advanced into the selected location in the anterior pararenal space under image guidance, such as to avoid injuring the pancreas. Such image-guided needle placement can comprise one or more of: ultrasound-guided needle placement (e.g. EUS-guided needle placement), CT-guided needle placement, and the like. If an EUS-guided placement is performed, the endoscope is first placed in the proper position in the stomach or duodenum, and depositing element 650 is advanced through the endoscope, through the wall of the stomach or duodenum, and into the anterior pararenal space to the desired treatment location.

In Step 4050, an optional step can be performed of injecting a visualization agent into the anterior pararenal space to confirm proper depositing device 600 location. The visualization agent can comprise saline, fluoroscopic contrast, $CO_2$, and/or another agent visible via an imaging device, such as imaging device 90 described herein. If depositing element 650 is not in the desired location, it can be re-positioned. If this confirmatory step is performed, a sub-step of aspirating the visualization agent can then optionally be performed prior to continuing.

In Step 4060, an optional step can be performed of insufflating the anterior pararenal space, such as with $CO_2$ or saline, to improve access to the exterior of the pancreas.

In Step 4070, an optional step can be performed of injecting a viscous filling agent into the lesser sac, such as to prevent a subsequent injection of material 60 from migrating into the lesser sac. In some embodiments, the viscous filling agent can comprise a visualizable agent (e.g. fluoroscopic contrast agent), or it can comprise a submucosal lifting agent, such as a lifting agent which biodegrades (e.g. Eleview, Orise, or other similar agent).

In Step 4080, an optional step can be performed of instilling a tissue-disseminating and/or a dissociating agent (e.g. hyaluronidase, collagenase, or the like) into the anterior pararenal space, such to improve the permeability of the pancreas prior to the subsequent delivery of material 60.

In Step 4090, material 60 (e.g. a gene therapy, chemotherapy agent, saline, anti-pancreatitis agent, and/or other treatment agent) is injected via depositing element 650 into the anterior pararenal space, under image guidance, such as while maintaining pressure at or below a desired level, as described herebelow. In some embodiments, material 60 comprises a treatment agent comprising an oncolytic virus, a cell therapy, antisense oligonucleotides, aptamers, small interfering RNAs, microRNAs, and/or messenger RNAs. The injected volume in this location can be at least 0.5 mL, 1 mL, and/or 2 mL. In some embodiments, system 10 can be configured to prevent each delivery of material 60 from exceeding a maximum volume of material 60 delivery, such as a maximum volume of no more than 2.5 mL, no more than 5.0 mL, and/or no more than 10.0 mL. Material 60 can include a liquid, powder, and/or a biodegradable polymer designed to elute a treatment agent (e.g. a pharmaceutical) over a time period, such as a time period of at least 1 hour, 2 hours, 3 hours, 1 week, 2 weeks, 4 weeks, and/or 8 weeks. Material 60 can optionally be configured to be visualized by imaging device 90 (e.g. mixed with ultrasound contrast and/or fluoroscopic contrast agent). Material 60 can optionally be co-formulated with hyaluronidase to improve the distribution of material 60 to the pancreas, or hyaluronidase can be injected at the same time as material 60. In some embodiments, a tissue-disseminating agent, such as hyaluronidase collagenase, or the like, is injected prior to and/or simultaneously with material 60. Alternatively or additionally, material 60 can be co-formulated with a tissue-disseminating and/or a dissociating agent such as hyaluronidase, collagenase, or the like.

In some embodiments of Step 4090, pressure within the tissue can be maintained at or below interstitial pressure (e.g. at or below 0, 3, 5, and/or 8 mmHg) such as by adding and/or withdrawing fluid through depositing device 600 (fluid such as material 60, visualization agent, saline, and/or other diluent), or optionally by using a computer-controlled device (e.g. a pumping assembly of console 200) attached to the proximal end of device 600. In this configuration, the maximum pressure can be maintained below interstitial pressure, or the pressure control can be pulsatile, and the average pressure can be maintained to remain below interstitial pressure. The pressure can be maintained in this manner for at least 1 minute, or at least 5, 10, 20 or 30 minutes.

In some embodiments of Step 4090, pressure within the tissue can be maintained above interstitial pressure (e.g. above 0, 3, 5, or 8 mmHg) and at or below capillary pressure (e.g. at or below 15, 20, or 25 mmHg), such as by adding and/or withdrawing fluid through depositing device 600 (fluid such as material 60, visualization agent, saline, and/or other diluent), or optionally by using a computer-controlled device (e.g. a pumping assembly of console 200) attached to the proximal end of device 600. In this configuration, the maximum pressure can be maintained below capillary pressure, or pressure control can be pulsatile so that average pressure remains below capillary pressure. The pressure can be maintained in this manner for at least 1 minute, or at least 5, 10, 20 or 30 minutes.

In Step 4110, an optional step of withdrawing depositing element 650 from the first location in the anterior pararenal space, identifying a second location in the anterior pararenal space for another injection, and repeating the injection steps can be performed. In some embodiments, multiple injections in additional locations can be performed in the same manner. The selected locations can be adjacent to the same portion of the pancreas (e.g. adjacent to the head, body, tail, and/or uncinate process of the pancreas), or the location(s) can be adjacent to two or more portions of the pancreas. Spacing between deposit site locations for injection can be at least 0.5 cm, 1 cm, and/or 2 cm. Cumulative volume injected across all injections can be at least 5 mL, 10 mL, 20 mL, and/or 40 mL. The total number of injections can be less than 5, 7, 10 or 12 injections. In some embodiments, the total number of injections is at least 2, 3, 4 or 5 injections.

In Step 4120, an optional step of aspirating material 60 (e.g. aspirating at least 30%, 50%, and/or 70% of injected volume of material 60) is performed, such as to remove excess fluid. Aspiration can be performed from multiple locations (e.g. deposit locations and/or locations proximate deposit locations), as fluid may have spread from the site of the injection.

In Step 4120, if the lesser sac was filled in a previous step, an optional step can be performed of aspirating some or all of the filling agent from the lesser sac.

After delivery of material 60 to a deposit site, at least a portion of the material 60 that remains within the lumen of the depositing element 650 can be evacuated from the lumen (e.g. into the patient at the deposit site), such as via introduction of a flushing material into the lumen (e.g. as described hereinabove in reference to FIG. 2). This optional evacuation step can be performed after the final delivery of material 60 (e.g. after the injection at the last deposit site).

Each component of system 10 that is advanced into the patient during the performance of method 4000 can be removed at an appropriate time after its use.

Figure 6:
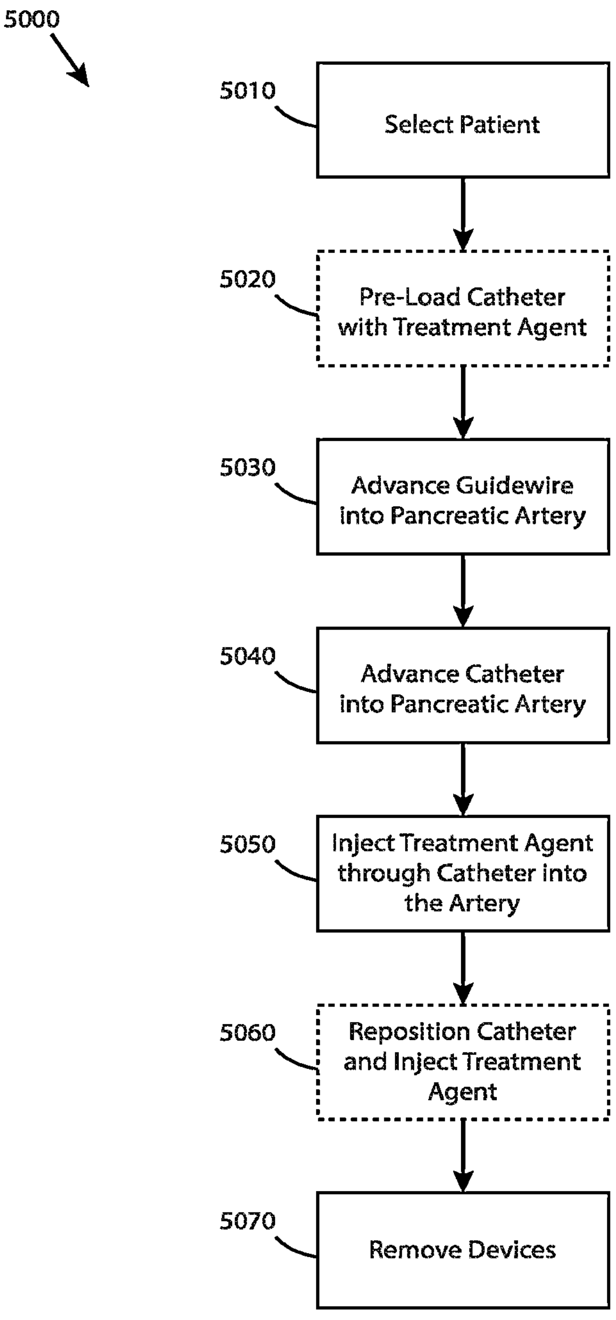
FIG. 6 illustrates a flow chart of another method for depositing material at a deposit site of a patient, consistent with the present inventive concepts.

Referring now to FIG. 6, a flow chart of another method for depositing material at a deposit site of a patient is illustrated, consistent with the present inventive concepts. Method 5000 of FIG. 6 includes numerous optional steps, and it shall be described in reference to the use of system 10 of FIG. 1 and otherwise herein. In some embodiments, method 5000 is configured to treat one, two or more medical conditions of a patient as described herein.

In Step 5010, a patient is selected. In some embodiments, the patient is selected to receive gene therapy of the pancreas. In some embodiments, the patient is selected to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas.

In some embodiments, in Step 5010 a patient is selected (e.g. a mammalian patient) with an HbA1c level of at least 6.5%, at least 7.0%, at least 7.5%, or at least 8%. In some embodiments, in Step 5010, a patient is selected that is obese, has a body mass index (BMI) of at least 30, has Type 2 diabetes, and has a HbA1c level above 7.0.

In some embodiments, a patient is selected that has Type 1 diabetes, such as a patient that has stage 1 of Type 1 diabetes, whereby stage 1 is defined as the presence of P-cell autoimmunity as evidenced by the presence of two or more islet autoantibodies with normoglycemia and is presymptomatic. In some embodiments, a patient is selected that has Type 1 diabetes, such as a patient that has stage 2 of Type 1 diabetes, whereby stage 2 is defined as the presence of β-cell autoimmunity with dysglycemia and is presymptomatic. In some embodiments, a patient is selected that has Type 1 diabetes, such as a patient that has stage 3 of Type 1 diabetes, whereby stage 3 is defined as onset of symptomatic disease.

In some embodiments a patient is selected that has: cystic fibrosis; non-cystic-fibrosis; pancreatic exocrine insufficiency; chronic hyperinsulinemia; chronic pancreatitis; a pancreatic cancer; pancreatic metastases; a partial pancreatectomy; and/or another disease of the pancreas.

In some embodiments, a patient is selected in Step 5010 that has a BMI of at least 30, 35, and/or 40.

In some embodiments, a patient is selected in Step 5010 that has a pancreas with a minimum level of functionality, such as when the patient has a C-Peptide level of at least 0.2, 1.0, and/or 2.0 (nM or nmol/l) and/or a fasting insulin of at least 7 μU/mL, 9 μU/mL, or 12 μU/mL. Alternatively or additionally, a patient is selected in Step 5010 with a C-Peptide level of less than 0.6, 0.8, 1.0, and/or 2.0 (nM or nmol/l) and/or a fasting insulin of less than 12 μU/mL, 14 μU/mL, or 16 μU/mL.

In some embodiments, a patient is selected in Step 5010 that has a relatively non-cirrhotic liver, such as when the patient has: a Fib-4 level of no more than 4; a Fib-4 level of at least 1.3, 2.0, and/or 2.5 (e.g. when the patient has NAFLD and/or NASH); an ALT level of at least 30, 35, and/or 40; an AST level of at least 25, 30, and/or 35; and combinations of one, two, or more of these.

In some embodiments, a female patient is selected in Step 5010 that has impaired ovarian function, such as a patient that has oligomenorrhea (e.g. menses with a cycle of at least 35 days) and/or amenorrhea (e.g. no menses for at least 6 months). In some embodiments, a male patient is selected in Step 5010 that has impaired testosterone levels and/or impaired sexual function (such as impotence).

In some embodiments, a patient is selected in Step 5010 that has insulin resistance, such as when the patient has: a triglyceride/HDL ratio of at least 1.65 and/or 2.75; a HOMA-IR level of at least 2.0, 2.5, and/or 3.0; a fasting insulin of at least 5 μU/mL, 7 μU/mL, and/or 10 μU/mL; and/or a fasting glucose of at least 100 mg/dL and/or 125 mg/dL.

In some embodiments, a patient is selected in Step 5010 that has liver disease, such as fatty liver disease or other liver disease diagnosed and/or prognosed via magnetic resonance (MR) imaging and/or ultrasound imaging. For example, magnetic resonance imaging can be used to determine a proton densitometry fat fraction (PDFF), also referred to as magnetic resonance fat fraction, where the patient is selected for treatment if their intra-hepatic triglyceride (IHTG) is at least 5%. Ultrasound imaging can be used to determine a hepato-renal index of echo levels (HRI), wherein the patient is selected for treatment if the HRI difference is at least 4.0 dB and/or the HRI ratio is no more than 1.0. A fibroscan (transient elastography) can be used to assess a patient for treatment. For example, a patient can be selected for treatment if their vibration controlled transient elastography is determined to be at least 6 kPa, or at least 8 kPa (e.g. when measured at 50 Hz). Alternatively or additionally, a patient can be selected for treatment if their controlled attenuation parameter (CAP), also referred to as ultrasound attenuation rate, is at least 200 dB/m or at least 250 dB/m.

In some embodiments, a patient is selected in Step 5010 that has a metabolic disease, such as a metabolic disease diagnosed and/or prognosed via metabolomics. For example, a patient can be selected for treatment if their level of 2-hydroxybutyrate is no more than 5 μg/mL.

In some embodiments, a patient is selected in Step 5010 that has post-bariatric hypoglycemia. For example, a post-bariatric surgery patient can be selected: if a post-prandial blood sugar level is determined by system 10 to be below 70 mg/dL, 60 mg/dL, and/or 50 mg/dL; if the patient has known hypoglycemia unawareness; and/or if the patient has documented history of severe hypoglycemia, such as one or more hypoglycemic events requiring third party assistance.

In some embodiments, a patient is selected in Step 5010 that has a hormonal defect, such as a patient with insufficient GLP-1 secretions (e.g. as determined by measuring circulating levels of these).

In Step 5020, an optional step is performed of pre-loading depositing device 600 with the treatment agent, material 60. In some embodiments, the distal end of device 600 is pre-loaded with material 60.

In Step 5030, a guidewire, such as a steerable guidewire, is advanced via an arterial puncture site (e.g. a femoral artery puncture site) into one of the arteries feeding the pancreas, such as the superior pancreaticoduodenal artery, inferior pancreaticoduodenal artery, gastroduodenal artery, superior mesenteric artery, celiac artery, hepatic artery, splenic artery, common hepatic artery, and/or gastroduodenal artery (GDA).

In Step 5040, depositing device 600 is delivered over the guidewire into the artery.

In Step 5050, material 60 is injected through depositing device 600 into the artery. The agent can be injected slowly, such as a delivery over a time period of at least 30 seconds, 1 minute, 2 minutes, and/or 5 minutes. Material 60 can comprise one or more materials, such as those that are described in reference to FIG. 1 and otherwise herein. In some embodiments, material 60 comprises at least a gene therapy material (e.g. a gene therapy vector and/or a gene editing vector). Alternatively or additionally, material 60 can comprise a treatment agent comprising an oncolytic virus, a cell therapy, antisense oligonucleotides, aptamers, small interfering RNAs, microRNAs, and/or messenger RNAs.

In Step 5060, an optional step is performed where depositing device 600 and guidewire (if present) are withdrawn into the aorta, and the guidewire is then advanced into a second artery feeding a different portion of the pancreas. Device 600 is then re-delivered over the guidewire, and additional material 60 is injected through device 600, in the same manner as the first injection.

After delivery of material 60 to a deposit site, at least a portion of the material 60 that remains within the lumen of the depositing element 650 can be evacuated from the lumen (e.g. into the patient at the deposit site), such as via introduction of a flushing material into the lumen (e.g. as described hereinabove in reference to FIG. 2). This optional evacuation step can be performed after the final delivery of material 60 (e.g. after the injection at the last deposit site).

In Step 5070, depositing device 600 and guidewire (if present), and other associated system 10 devices, are withdrawn from the body and the puncture site is closed in the usual manner.

Figure 7:
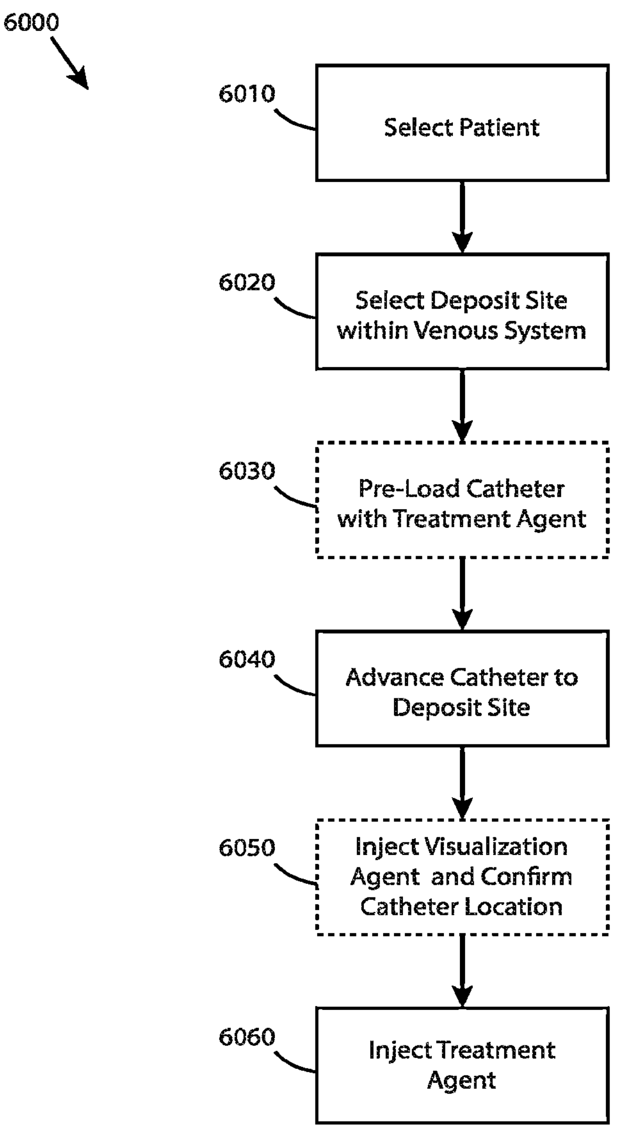
FIG. 7 illustrates a flow chart of another method for depositing material at a deposit site of a patient, consistent with the present inventive concepts.

Referring now to FIG. 7, a flow chart of another method for depositing material at a deposit site of a patient is illustrated, consistent with the present inventive concepts. Method 6000 of FIG. 7 includes numerous optional steps, and it is described in reference to the use of system 10 of FIG. 1 and otherwise herein. In some embodiments, method 6000 is configured to treat one, two or more medical conditions of a patient, such as Type 1 diabetes, Type 2 diabetes, and/or another medical condition of the patient, such as is described herein.

In Step 6010, a patient is selected. In some embodiments, the patient is selected to receive gene therapy of the liver. In some embodiments, the patient is selected to receive cell therapy, such as the instillation of pancreatic islets. In some embodiments, the pancreatic islets have been genetically transduced prior to instillation to improve secretory function. In some embodiments, the patient is selected to receive an intravenous infusion agent for the treatment of a liver condition, such as when the patient is selected to receive one or more anti-cancer agents, such as an immunotherapeutic agent or chemotherapeutic agent. In some embodiments, the patient is selected to receive an agent to treat acute pancreatitis, such as an anti-cytokine agent, an anti-inflammatory agent, or other agents.

In some embodiments, in Step 6010 a patient is selected (e.g. a mammalian patient) with an HbA1c level of at least 6.5%, at least 7.0%, at least 7.5%, or at least 8%. In some embodiments, in Step 6010, a patient is selected that is obese, has a body mass index (BMI) of at least 30, has Type 2 diabetes, and has a HbA1c level above 7.0. In some embodiments, a patient is selected who has had a pancreatectomy for chronic pancreatitis. In some embodiments a patient is selected who has hepatocellular carcinoma. In some embodiments, the patient is selected to treat: Type 1 or Type 2 diabetes, other forms of diabetes; NAFLD/NASH; obesity; Alzheimer's disease; acute or chronic pancreatitis; pancreatic cancer; pancreatic metastases; cystic fibrosis; exocrine pancreatic insufficiency; partial pancreatectomy; hyperinsulinemia; hyperglucagonemia; and/or another disease or disorder of the pancreas.

In some embodiments, a patient is selected that has Type 1 diabetes, such as a patient that has stage 1 of Type 1 diabetes, whereby stage 1 is defined as the presence of P-cell autoimmunity as evidenced by the presence of two or more islet autoantibodies with normoglycemia and is presymptomatic. In some embodiments, a patient is selected that has Type 1 diabetes, such as a patient that has stage 2 of Type 1 diabetes, whereby stage 2 is defined as the presence of β-cell autoimmunity with dysglycemia and is presymptomatic. In some embodiments, a patient is selected that has Type 1 diabetes, such as a patient that has stage 3 of Type 1 diabetes, whereby stage 3 is defined as onset of symptomatic disease.

In some embodiments a patient is selected that has: cystic fibrosis; non-cystic-fibrosis; pancreatic exocrine insufficiency; chronic hyperinsulinemia; chronic pancreatitis; a pancreatic cancer; pancreatic metastases; a partial pancreatectomy; and/or another disease of the pancreas.

In some embodiments, a patient is selected in Step 6010 that has a BMI of at least 30, 35, and/or 40 Kg/m 2.

In some embodiments, a patient is selected in Step 6010 that has a pancreas with a minimum level of functionality, such as when the patient has a C-Peptide level of at least 0.2, 1.0, and/or 2.0 (nM or nmol/l) and/or a fasting insulin of at least 7 μU/mL, 9 μU/mL, or 12 μU/mL. Alternatively or additionally, a patient is selected in Step 6010 with a C-Peptide level of less than 0.6, 0.8, 1.0, and/or 2.0 (nM or nmol/l) and/or a fasting insulin of less than 12 μU/mL, 14 μU/mL, or 16 μU/mL.

In some embodiments, a patient is selected in Step 6010 that has a relatively non-cirrhotic liver, such as when the patient has: a Fib-4 level of no more than 4; a Fib-4 level of at least 1.3, 2.0, and/or 2.5 (e.g. when the patient has NAFLD and/or NASH); an ALT level of at least 30, 35, and/or 40; an AST level of at least 25, 30, and/or 35; a creatinine clearance rate of greater than at least 40 mL/min; a serum creatinine level of no more than 1.5 mg/dL; a urine volume of at least 500 mL/day; a urine sodium level of at least 10 mEq/L; absence of portal hypertension; absence of ascites; and combinations of one, two, or more of these.

In some embodiments, a female patient is selected in Step 6010 that has impaired ovarian function, such as a patient that has oligomenorrhea (e.g. menses with a cycle of at least 35 days) and/or amenorrhea (e.g. no menses for at least 6 months). In some embodiments, a male patient is selected in Step 6010 that has impaired testosterone levels and/or impaired sexual function (such as impotence).

In some embodiments, a patient is selected in Step 6010 that has insulin resistance, such as when the patient has: a triglyceride/HDL ratio of at least 1.65 and/or 2.75; a HOMA-IR level of at least 2.0, 2.5, and/or 3.0; a fasting insulin of at least 5 μU/mL, 7 μU/mL, and/or 10 μU/mL; and/or a fasting glucose of at least 100 mg/dL and/or 125 mg/dL.

In some embodiments, a patient is selected in Step 6010 that has liver disease, such as fatty liver disease or other liver disease diagnosed and/or prognosed via magnetic resonance (MR) imaging and/or ultrasound imaging. For example, magnetic resonance imaging can be used to determine a proton densitometry fat fraction (PDFF), also referred to as magnetic resonance fat fraction, where the patient is selected for treatment if their intra-hepatic triglyceride (IHTG) is at least 5%. Ultrasound imaging can be used to determine a hepato-renal index of echo levels (HRI), wherein the patient is selected for treatment if the HRI difference is at least 4.0 dB and/or the HRI ratio is no more than 1.0. A fibroscan (transient elastography) can be used to assess a patient for treatment. For example, a patient can be selected for treatment if their vibration controlled transient elastography is determined to be at least 6 kPa, or at least 8 kPa (e.g. when measured at 50 Hz). Alternatively or additionally, a patient can be selected for treatment if their controlled attenuation parameter (CAP), also referred to as ultrasound attenuation rate, is at least 200 dB/m or at least 250 dB/m.

In some embodiments, a patient is selected in Step 6010 that has a metabolic disease, such as a metabolic disease diagnosed and/or prognosed via metabolomics. For example, a patient can be selected for treatment if their level of 2-hydroxybutyrate is no more than 5 μg/mL.

In some embodiments, a patient is selected in Step 6010 that has post-bariatric hypoglycemia. For example, a post-bariatric surgery patient can be selected: if a post-prandial blood sugar level is determined by system 10 to be below 70 mg/dL, 60 mg/dL, and/or 50 mg/dL; if the patient has known hypoglycemia unawareness; and/or if the patient has documented history of severe hypoglycemia, such as one or more hypoglycemic events requiring third party assistance.

In some embodiments, a patient is selected in Step 6010 that has a hormonal defect, such as a patient with insufficient GLP-1, PPY, oxyntomodulin, glucagon, or insulin secretions (e.g. as determined by measuring circulating levels of these).

In Step 6020, one, two, or more locations within the hepatic portal venous system is selected as a deposit site, such as one, two, or more locations within the hepatic portal vein, splenic vein, superior mesenteric vein, inferior mesenteric vein, or the tributaries that lead to any of these veins (gastrocolic trunk, first jejuna vein, left gastric vein, posterior superior pancreatic-duodenal vein, left gastro-epiploic vein, the short gastric vein, and the posterior pancreatic veins), and that location can be visualized by imaging such as endoscopic ultrasound (EUS), ultrasound, MRI, fluoroscopy, and/or computed tomography.

In Step 6030, an optional step is performed of pre-loading a depositing element 650 of depositing device 600 with material 60. In some embodiments, depositing element 650 is pre-loaded from its distal end (e.g. when material 60 is drawn into depositing element 650 from its distal end).

In Step 6040, depositing element 650 is advanced into the selected venous system location under image guidance. This image-guided depositing element 650 placement can comprise one or more of: ultrasound-guided needle placement (e.g. EUS-guided needle placement), CT-guided needle placement, and the like. If an EUS-guided placement is performed, the endoscope is first placed in the proper position in the stomach or duodenum, and depositing element 650 is advanced through the endoscope, through the wall of the stomach or duodenum, and into the desired treatment location.

In Step 6050, an optional step can be performed of injecting a visualization agent through depositing element 650 to confirm proper depositing device 600 location. The visualization agent can comprise saline, ultrasonic contrast, fluoroscopic contrast, $CO_2$, and/or another agent visible via an imaging device, such as imaging device 90 described herein. If depositing element 650 is not in the desired location, it can be re-positioned.

In Step 6060, material 60 (e.g. a gene therapy material such as a gene therapy vector and/or a gene editing vector, chemotherapy agent, immunotherapy agent, saline, anti-pancreatitis agent, and/or other treatment agent) is injected via depositing element 650 into the selected location in the portal venous system, under image guidance, while maintaining pressure at or below a desired level, as described herebelow. In some embodiments, material 60 comprises a treatment agent comprising an oncolytic virus, a cell therapy, antisense oligonucleotides, aptamers, small interfering RNAs, microRNAs, and/or messenger RNAs. The injected volume in this location can be at least 10 mL, 15 mL, or 50 mL. In some embodiments, system 10 can be configured to prevent each delivery of material 60 from exceeding a maximum volume of material 60 delivery, such as a maximum volume of no more than 2.5 mL, no more than 5.0 mL, and/or no more than 10.0 mL. Material 60 can comprise a liquid, powder, and/or a biodegradable polymer designed to elute a treatment agent (e.g. a pharmaceutical) over a time period, such as at least 1 hour, 2 hours, 3 hours, 1 week, 2 weeks, 4 weeks, and/or 8 weeks. Material 60 can be configured to be visualized by imaging device 90 (e.g. mixed with ultrasound contrast and/or fluoroscopic contrast agent).

In some embodiments of Step 6060, pressure can be maintained at or below hepatic arterial pressure (e.g. at or below 60, 80, and/or 100 mmHg), such as by adding and/or withdrawing fluid through depositing device 600 (fluid such as material 60, a visualization agent, saline, and/or other diluent), or optionally by using a computer-controlled device (e.g. a pumping assembly of console 200) attached to the proximal end of device 600. In this configuration, the maximum pressure can be maintained below interstitial pressure, or the pressure control can be pulsatile so that the average pressure remains below hepatic arterial pressure.

In some embodiments of Step 6060, pressure can be maintained above minimal venous pressure (e.g. above 5, 7 or 9 mmHg) and/or at or below a maximum portal venous pressure (e.g. at or below 10, 12 or 14 mmHg), such as by controlling the rate of fluid flow through depositing device 600 (fluid such as material 60, visualization agent, saline, and/or other diluent), or optionally by using a computer-controlled device (e.g. a pumping assembly of console 200) attached to the proximal end of device 600. In this configuration, the maximum pressure can be maintained below maximum portal venous pressure, or pressure control can be pulsatile so that average pressure remains below maximum portal venous pressure.

After delivery of material 60 to a deposit site, at least a portion of the material 60 that remains within the lumen of the depositing element 650 can be evacuated from the lumen (e.g. into the patient at the deposit site), such as via introduction of a flushing material into the lumen (e.g. as described hereinabove in reference to FIG. 2). This optional evacuation step can be performed after the final delivery of material 60 (e.g. after the injection at the last deposit site).

Each component of system 10 that is advanced into the patient during the performance of method 6000 can be removed at an appropriate time after its use.

Figure 8:
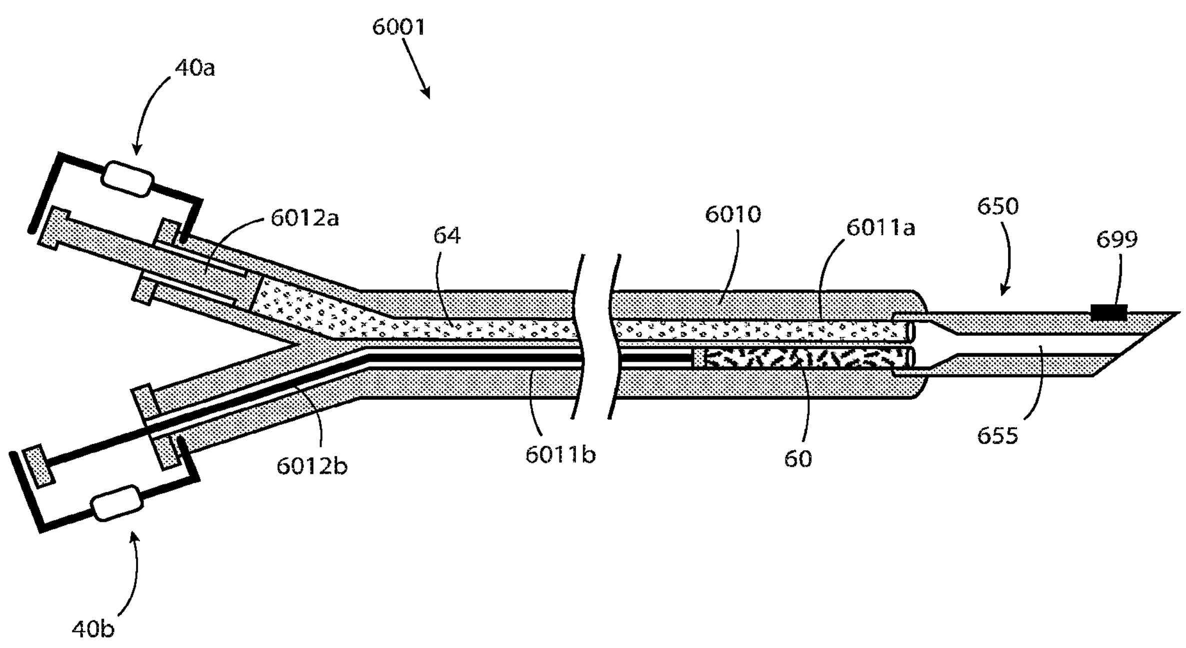
FIG. 8 illustrates a side sectional view of a depositing device, consistent with the present inventive concepts.

Referring now to FIG. 8, a side sectional view of a depositing device is illustrated, consistent with the present inventive concepts. Depositing device 6001 of FIG. 8 can be of similar construction and arrangement to depositing device 600 described in reference to FIG. 1 and otherwise herein. In some embodiments, depositing device 6001 is constructed and arranged to deliver one or more materials (e.g. material 60 and/or flush 64) into the pancreas and/or other body location of a patient. Depositing device 6001 comprises a multi-lumen elongate shaft, shaft 6010, comprising lumens 6011*a* and 6011*b*, shown. In some embodiments, shaft 6010 comprises more than two lumens, such as three, four, or more lumens, such as two or more individual lumens each intended to deposit a unique agent or material Into the patient. Device 6001 can comprise a first fluid drive mechanism, plunger 6012*a*, that is slidingly received by the proximal end of lumen 6011*a* and is configured to drive (e.g. push) material (e.g. flush 64) through lumen 6011*a*. Device 6001 can further comprise a second fluid drive mechanism, plunger 6012*b*, that is slidingly received within lumen 6011*b* and is configured to drive material (e.g. material 60) through lumen 6011*b*. In some embodiments, plunger 6012*b* comprises an elongate structure that extends to a distal portion of lumen 6011*b*, as shown. Alternatively, the proximal ends of lumens 6011*a* and 6011*b* can operably attach to one or more syringes (e.g. syringes 610, not shown).

Depositing device 6001 can include depositing element 650, comprising a single lumen needle including lumen 655 that is operably attached (e.g. at least fluidly attached) to the distal ends of both lumens 6011*a* and 6011*b*. Depositing element 650 can comprise a needle with a gauge of as large as 19G, and/or as small as 25G. Depositing element 650 can comprise the same outer diameter as shaft 6010, or it can comprise a different (e.g. smaller) outer diameter than shaft 6010. Depositing element 650 and at least a distal portion of shaft 6010 can comprise an outer diameter of no greater than 2.2 mm, 2.8 mm, and/or 3.8 mm, such that at least the distal portion of depositing device 6001 can be slidingly received within a working channel of an access device 50 described herein (e.g. an endoscope). In some embodiments, depositing element 650 is fixedly attached to shaft 6010 of device 6001 (e.g. fixedly attached during a manufacturing process of device 6001). Alternatively, depositing element 650 can be removably attached and/or removably attachable ("removably attached" or "removably attachable" herein) to shaft 6010 (e.g. when depositing element 650 is attached to shaft 6010 by the operator prior to insertion into a patient). In some embodiments, depositing element 650 comprises a sealed distal end with one or more openings to lumen 655 along its length (e.g. as described in reference to FIG. 10).

In some embodiments, the proximal portion of shaft 6010 is bifurcated into a Y-shape, with the proximal portions of lumens 6011*a* and 6011*b* each extending through a unique portion of the bifurcation, as shown.

In some embodiments, depositing device 6001 includes one or more functional elements, functional element 699 shown. Functional element 699 can be positioned on a distal portion of device 6001, such as when positioned on depositing element 650. Functional element 699 can comprise a sensor configured to detect when depositing element 650 is in contact with tissue, such as an impedance and/or a pressure sensor. In some embodiments, a functional element 699 comprising a sensor is positioned proximal to the distal tip of depositing element 650, such as between 2 mm and 10 mm from the distal tip. Functional element 699 can transmit signals to console 200 (not shown but described herein) indicating when depositing element has been inserted into a deposit site (e.g. inserted an appropriate distance into the pancreas, such as 2 mm to 10 mm into the pancreas). In some embodiments, functional element 699 comprises a sensor configured to measure the electrical properties of the tissue surrounding depositing element 650, such as the conductivity and/or the resistivity of the tissue. Functional element 699 can comprise a sensor selected from the group consisting of: a pH sensor; physiologic sensor; blood glucose sensor; blood gas sensor; blood sensor; respiration sensor; EKG sensor; EEG sensor; neuronal activity sensor; blood pressure sensor; flow sensor, such as a flow rate sensor; volume sensor; pressure sensor; force sensor; sound sensor, such as an ultrasound sensor; electromagnetic sensor, such as an electromagnetic field sensor or an electrode; gas bubble detector, such as an ultrasonic gas bubble detector; strain gauge; magnetic sensor; ultrasonic sensor; optical sensor, such as a light sensor; chemical sensor; visual sensor, such as a camera; temperature sensor, such as a thermocouple, thermistor, resistance temperature detector, or optical temperature sensor; impedance sensor, such as a tissue impedance sensor; and combinations of two or more of these. In some embodiments, functional element is configured to detect a pH, such as to identify tissue based on pH data. For example, a particular deposit site can be identified based on pH within a range indicative of that deposit site, such as a pH between 7.5 and 8 that is indicative of the fluids present within the pancreas. In some embodiments, functional element 699 is configured to detect a temperature indicative of a particular deposit site, and/or to detect a change in temperature indicative of leaving one location and entering a deposit site, for example a change in temperature indicative of leaving interstitial space and/or a first organ, and entering a second organ (e.g. the pancreas). In some embodiments, a positive signal from functional element 699 (e.g. a signal indicating depositing element 650 is properly inserted into a deposit site, such as pancreatic tissue) could be required by system 10 to allow the initiation of a depositing procedure (e.g. a "go/no go" signal required to be "go" to perform an injection). In some embodiments, functional element 699 comprises a flexible circuit board wrapped at least partially circumferentially around depositing element 650. In some embodiments, depositing element 650 comprises a recess, such as a laser etched recess within which at least a portion of functional element 699 is positioned. In some embodiments, functional element 699 comprises a pressure sensor configured to record pressure information of a fluid pathway in which material 60 passes through and/or from which material 60 is delivered. (e.g. a fluid pathway of depositing element 650).

System 10 can include one or more syringe drivers 40, such as drivers 40*a* and 40*b* shown. Drivers 40*a,b* can operably attach to device 6001, such as to actuate plungers 6012*a* and 6012*b*, respectively. In some embodiments, drivers 40*a,b* comprise computer-controlled (e.g. via console 200) motorized drivers that are configured to actuate plungers 6012*a,b*.

Figure 9:
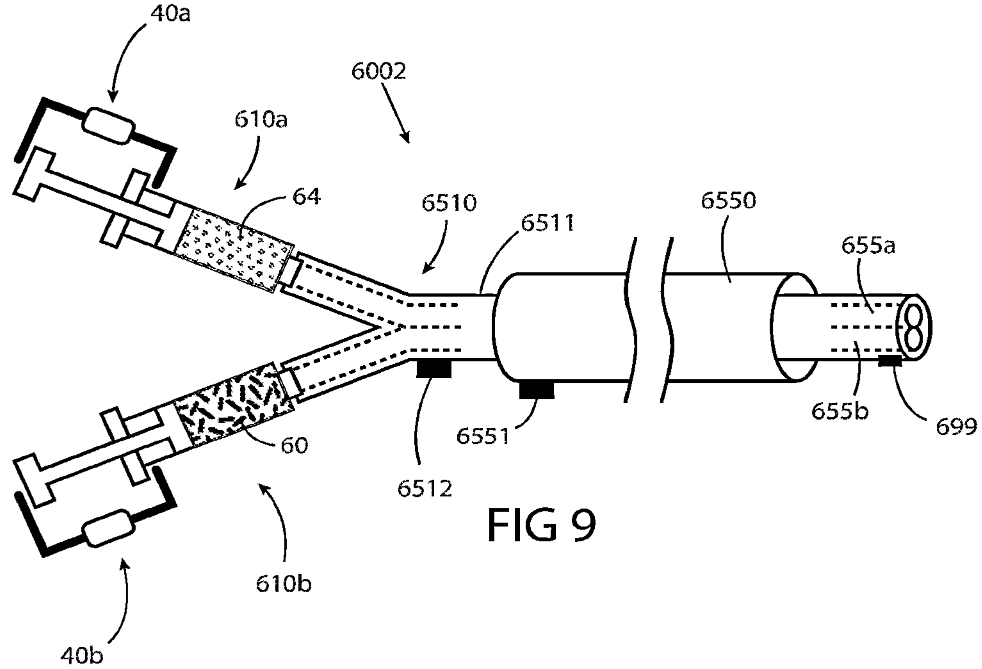
FIG. 9 illustrates a side sectional view of a depositing device, consistent with the present inventive concepts.

Referring now to FIG. 9, a side sectional view of a depositing device is illustrated, consistent with the present inventive concepts. Depositing device 6002 of FIG. 9 can be of similar construction and arrangement to depositing device 600 described in reference to FIG. 1 and otherwise herein. In some embodiments, depositing device 6002 is constructed and arranged to deliver one or more materials (e.g. material 60 and/or flush 64) into the intra-retroperitoneal space of a patient. Depositing device 6002 includes catheter 6510, comprising a multi-lumen elongate depositing element. Device 6002 includes an elongate shaft, shaft 6511 shown, which can comprise one or more lumens, such as lumens 655*a* and 655*b* shown. Shaft 6511 can comprise an atraumatic distal end. In some embodiments, at least one lumen of catheter 6510 can be configured to be filled with material (e.g. material such as when filled from the distal end of catheter 6510 (e.g. when the material is drawn in via suction from the distal end). Lumens 655*a,b* can be similar or dissimilar, for example comprising varying shapes and/or varying cross-sectional areas.

Device 6002 can include a flexible conduit, trocar 6550 shown, that slidingly receives catheter 6501. Trocar 6550 can be configured to be slidingly received within a working channel of an access device (e.g. access device 50, not shown), such as when received by a working channel that is less than 4.2 mm in diameter, such as less than 3.8 mm in diameter. Trocar 6550 can comprise a handle, handle 6551 shown. In some embodiments, catheter 6510 comprises a handle, handle 6512, also shown. Trocar 6550 and/or catheter 6510 can be manually advanced and/or retracted (e.g. via handles 6551 and/or 6512, respectively) relative to each other and/or relative to an access device 50 (not shown), such as an endoscope. Alternatively or additionally, system 10 can comprise one or more actuators, such as one or more actuators configured to operably attach to handle 6551, handle 6512, and or the handle of an endoscope to advance and/or retract catheter 6510, trocar 6550, and/or an access device 50.

In some embodiments, the proximal portion of catheter 6510 is bifurcated into a Y-shape, with the proximal portions of lumens 655*a* and 655*b* each extending through a unique portion of the bifurcation, as shown.

System 10 can include one or more syringes 610, such as syringes 610*a* and 610*b* shown. Syringes 610*a* and 610*b* can each operably attach to the proximal ends of lumens 655*a* and 655*b*, respectively. System 10 can include one or more syringe drivers 40, such as drivers 40*a* and 40*b* shown. Drivers 40*a,b* can operably attach to syringes 610*a* and 610*b*, respectively. In some embodiments, drivers 40*a,b* comprise computer-controlled (e.g. via console 200) motorized drivers configured to actuate plungers of syringes 610*a,b*. Syringe 610*a* can be configured to inject a first material (e.g. flush 64 shown) through a first lumen of catheter 6510 (e.g. lumen 655*a* shown). Syringe 610*b* can be configured to inject a second material (e.g. material 60 shown) through a second lumen of catheter 6510 (e.g. lumen 655*b* shown). Alternatively, catheter 6510 can comprise a single lumen catheter, and one or more syringes can be configured to attach (e.g. one at a time) to the proximal end of the lumen (e.g. to inject one or more material through the lumen into the patient). In some embodiments, device 6002 comprises an elongate plunger, such as a plunger configured to be positioned within a lumen of catheter 6510, which can be similar to plunger 6012*b* described herein in reference to FIG. 8.

In some embodiments, depositing device 6002 includes one or more functional elements, functional element 699 shown. Functional element 699 can be positioned on a distal portion of device 6001, such as on a distal portion of trocar 6550 or catheter 6510 (as shown). Functional element 699 can comprise a sensor configured to detect when a portion of device 6002 is in contact with tissue, such as an impedance and/or a pressure sensor. In some embodiments, functional element 699 comprises a marker positioned on depositing element 650, such as a radiopaque or other marker configured to indicate a distance from the distal end of depositing element 650 and/or a distance from the most proximal opening along the length of depositing element 650 (e.g. openings 6503 described immediately herebelow). A functional element 699 comprising a marker can be positioned less than 1.5 cm, 1.0 cm, and/or 0.5 cm from the distal end and/or most proximal opening of depositing element 650. The marker can comprise a high-density material (e.g. higher density than depositing element 650), a radiopaque material, and/or a surface modification to depositing element 650, such as a surface comprising micro-dimples, micro-ridges, and/or other surface contours, or a surface modification created used bead blasting and/or sand blasting. Material such as gold or platinum can be sputtered onto depositing element 650 to form the marker.

Figure 10:
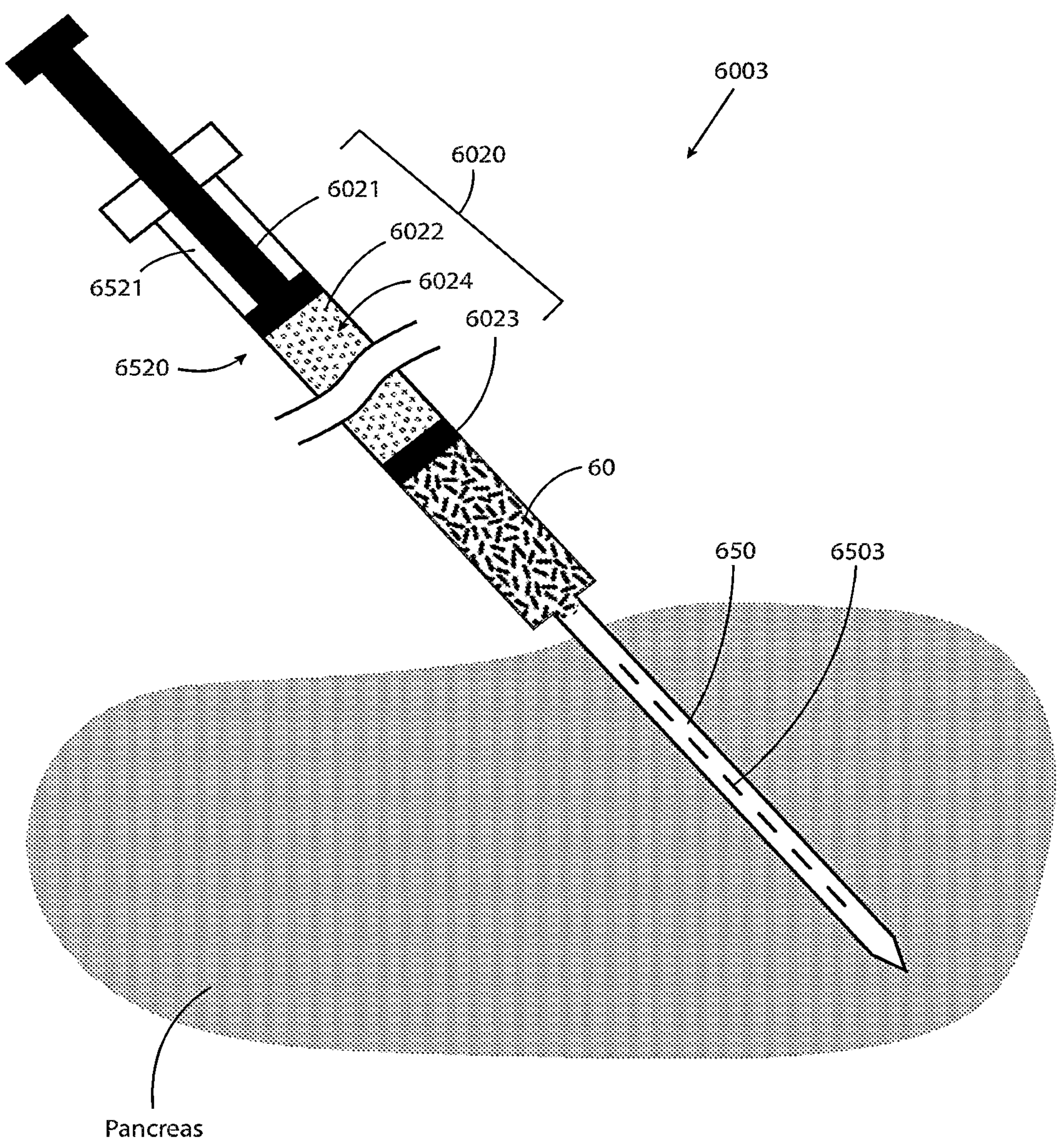
FIG. 10 illustrates a side sectional view of a depositing device, consistent with the present inventive concepts.

Referring now to FIG. 10, a side sectional view of a depositing device is illustrated, consistent with the present inventive concepts. Depositing device 6003 of FIG. 10 can be of similar construction and arrangement to depositing device 600 described in reference to FIG. 1 and otherwise herein. Device 6003 can be constructed and arranged to deliver one or more materials (e.g. material 60) into the pancreas or other body location of a patient. Depositing device 6003 can comprise an elongate body, syringe 6520, with lumen 6251 extending therethrough. Syringe 6520 is shown operably attached to a depositing element 650 comprising a needle. Depositing element 650 can comprise a fenestrated needle that includes one or more openings along its length, openings 6503 shown. In some embodiments openings 6503 comprise laser-etched openings. Alternatively or additionally, openings 6503 can comprise drilled (e.g. laser drilled) and/or punched openings. Openings 6503 can be positioned within 3 cm, within 2 cm, and/or within 1.5 cm of the distal end of depositing element 650. In some embodiments, openings 6503 are spaced at least 1 mm apart, such as at least 5 mm, or at least 1 cm. In some embodiments, openings 6503 comprise an array of micro-holes, comprising at least 100 micro-holes, such as at least 1000 or 5000 micro-holes. Openings 6503 (e.g. comprising an array of micro-holes) can be symmetrically spaced around depositing element 650, and/or asymmetrically spaced, such as asymmetrically in a helical pattern. In some embodiments, depositing element 650 comprises a closed distal end with side openings 6503.

Device 6003 can comprise drive assembly 6020, which can include plunger 6021, pneumatic fluid 6022, and a translating element, plug 6023, each as shown. Plug 6023 and plunger 6021 can be slidingly received within a lumen, lumen 6521 shown, of syringe 6520, creating a sealed chamber therebetween, chamber 6024. The chamber 6024 is filled with pneumatic fluid 6022, operably joining plunger 6021 to plug 6023. When plunger 6021 is advanced and/or retracted within syringe 6520, plug 6023 advances and/or retracts in unison due to the pneumatic force imparted via pneumatic fluid 6022. Plug 6023 can be advanced and/or retracted (e.g. via plunger 6021) to push material 60 from syringe 6520 and/or draw material 60 into syringe 6520, respectively. In some embodiments, device 6003 comprises a second syringe, not shown, but operably attached (e.g. at least fluidly attached) via a removable umbilical to chamber 6024 (e.g. when chamber 6024 comprises the sealed proximal portion of syringe 6520). The second syringe can be filled with pneumatic fluid 6022 and it can be configured to pneumatically advance and/or retract plug 6023 similar to plunger 6021 shown. In some embodiments, plunger 6021 and/or the second syringe are driven by a syringe driver, such as a syringe driver as described herein.

Figures 11A, 11B:
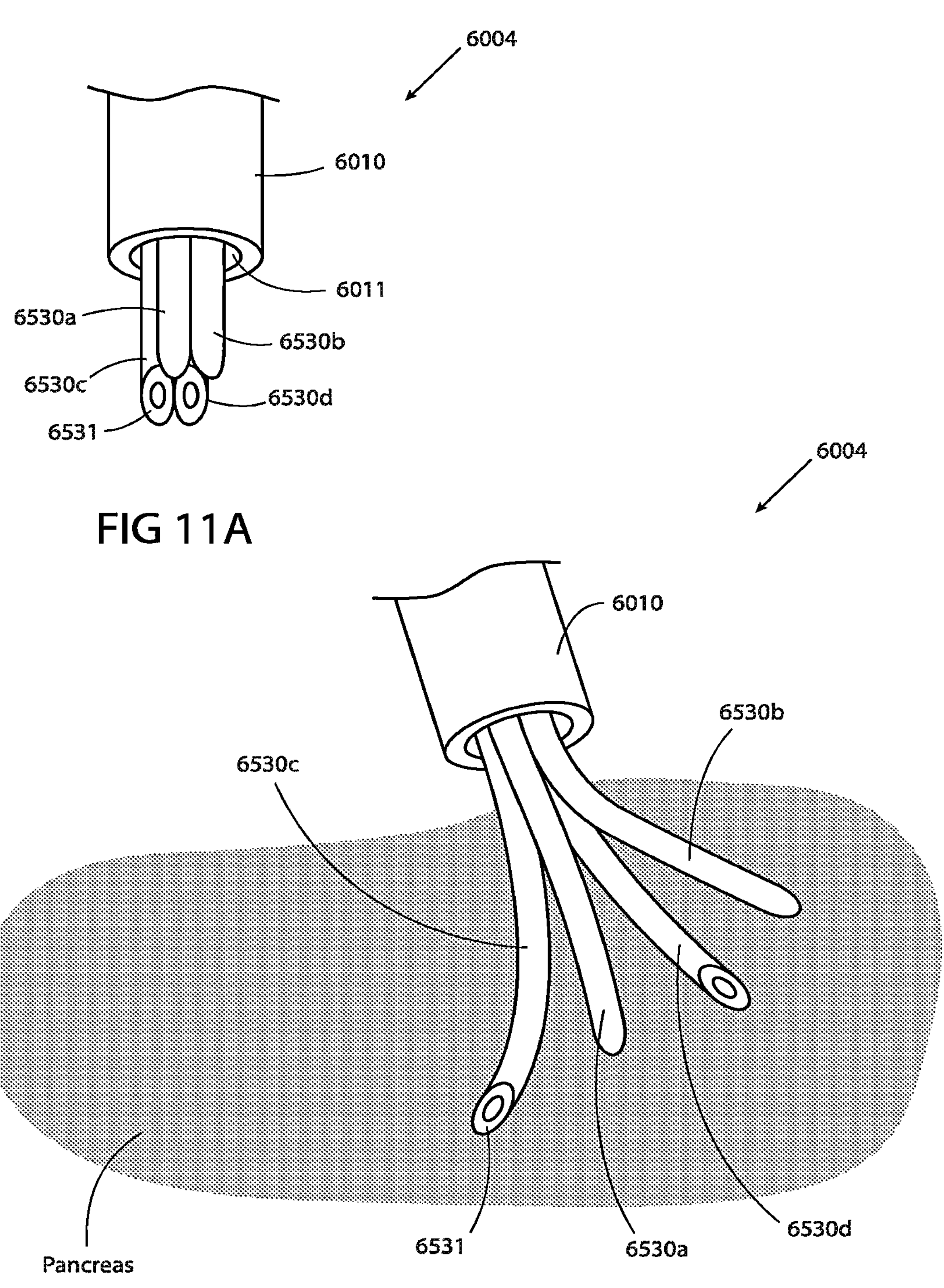
FIGS. 11A and 11B illustrate side views of the distal portion of a depositing device, consistent with the present inventive concepts.

Referring now to FIGS. 11A and 11B, side views of the distal portion of a depositing device are illustrated, consistent with the present inventive concepts. Depositing device 6004 of FIGS. 11A and 11B can be of similar construction and arrangement to depositing device 600 described in reference to FIG. 1 and otherwise herein. Depositing device 6004 comprises a shaft, shaft 6010, comprising at least one lumen, lumen 6011 shown. Device 6004 comprises multiple depositing elements 650, each comprising a needle, needles 6530*a-d* shown (singly or collectively needles 6530 herein). Each needle 6530*a-d* comprises a beveled face, bevels 6531, as shown. Needles 6530*a-d* are slidingly received within lumen 6011 of shaft 6010. In a retracted position (e.g. the partially retracted position shown in FIG. 11A), the bevels 6531 of needles 6530*a-d* face inward, as shown. Needles 6530 can comprise four needles, such as needles 6530*a-d* shown. Alternatively, needles 6530 can comprise, 2, 3, or more needles.

Needles 6530 can be advanced and/or retracted relative to shaft 6010. For example, needles 6530 can be advanced from shaft 6010 and inserted into patient tissue, for example into pancreatic tissue as shown in FIG. 11B. In some embodiments, needles 6530 are sufficiently thin and flexible such that force imparted on the beveled edges of the needles 6530 by the tissue into which the needles 6530 are being advanced causes the needles 6530 to deflect as they travel through the tissue. For example, as shown in FIG. 11B, when the bevels of needles 6530 are inward facing, needles 6530 can deflect outwards (opposite the beveled face) away from the central axis of device 6004, as shown. This deflection can be configured such that material 60 is delivered collectively from the multiple needles 6530 to a large volume of tissue than would be achieved without the deflection. In some embodiments, shaft 6010 can comprise a sharp distal end (e.g. similar to a trocar), such that shaft 6010 can puncture tissue, such as the wall of the stomach. For example, shaft 6010 can puncture the stomach wall such that the distal end of shaft 6010 is positioned proximate the pancreas (e.g. extending through the stomach wall to the pancreas), and needles 6530 can be advanced directly into the pancreas from shaft 6010.

Figures 12A, 12B, 12C:
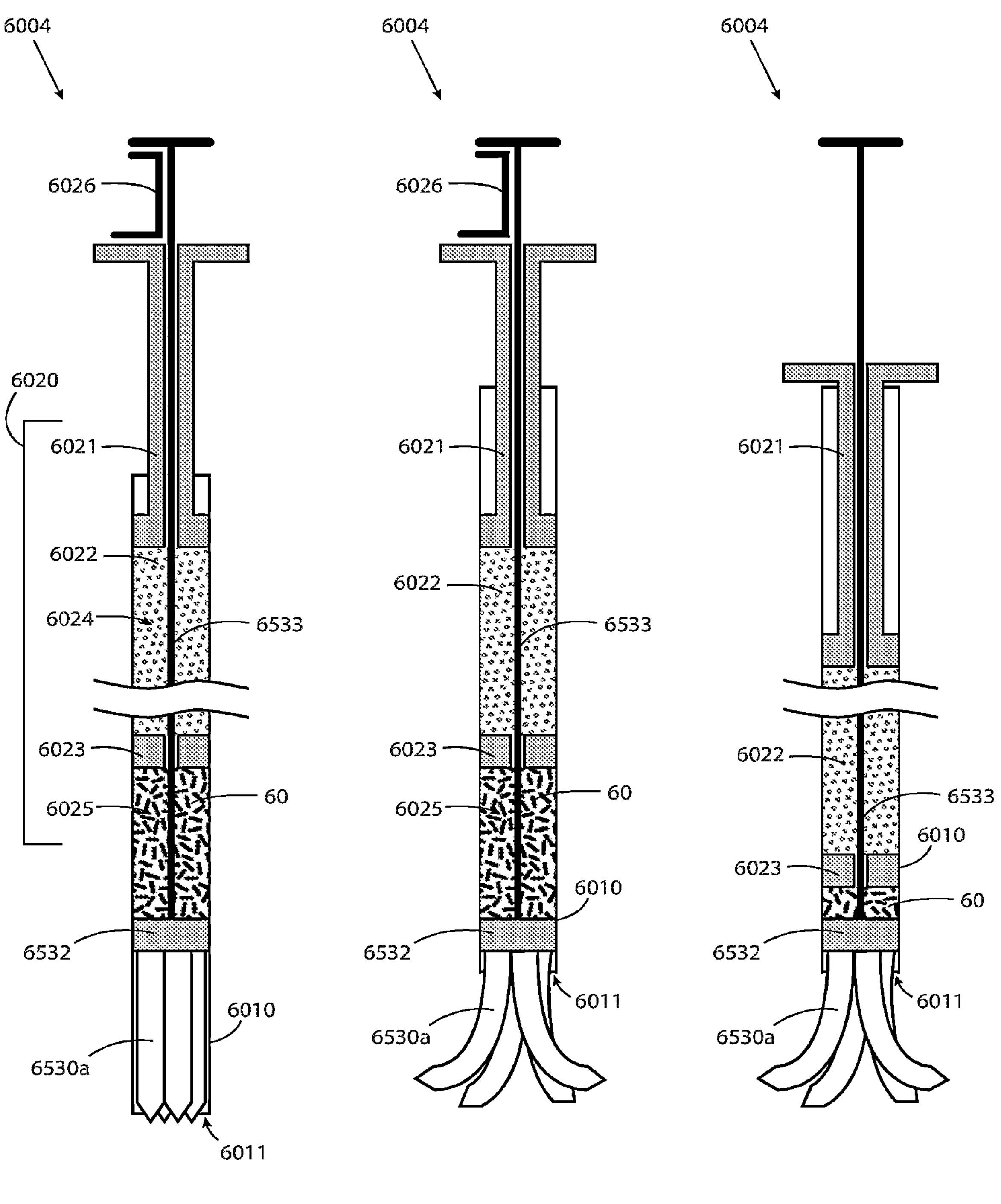
FIGS. 12A-12C illustrate side sectional views of a depositing device, consistent with the present inventive concepts.

Referring additionally to FIGS. 12A-12C, side sectional views of a depositing device are illustrated, consistent with the present inventive concepts. Depositing device 6004 of FIGS. 12A-C includes multiple depositing elements, such as the four needles shown, needles 6350*a-d*. In some embodiments, device 6004 comprises two, three, five, or more needles. In FIG. 12A, needles 6530*a-d* are shown retracted inside lumen 6011 of shaft 6010. Needles 6530*a-d* are attached to a translatable hub, hub 6532 shown, that is slidingly received within lumen 6011 of shaft 6010. Needles 6530*a-d* translate with hub 6532, such that when hub 6532 is advanced through lumen 6011, needles 6530*a-d* advance (e.g. from the distal end of lumen 6011). Device 6004 can include an actuator, control rod 6533, that is attached to hub 6532 and extends proximally from the proximal end of lumen 6011. Control rod 6533 can allow an operator of system 10 to manipulate the position of hub 6532 within lumen 6011 (e.g. to advance and/or retract hub 6532 and needles 6530*a-d*). In some embodiments, console 200 is configured to control the position of control rod 6533. Each of needles 6530 can comprise a lumen that extends through hub 6532, such that material (e.g. material 60) can pass through hub 6532 into needles 6530 and into the patient.

Device 6004 can comprise drive assembly 6020, which can be similar to drive assembly 6020 described in reference to FIG. 10 herein. Drive assembly 6020 comprises plunger 6021, pneumatic fluid 6022, and a translating element, plug 6023. Plug 6023 and plunger 6021 can be slidingly received within lumen 6011 of shaft 6010, creating a first chamber, chamber 6024, between plunger 6012 and plug 6023, and a second chamber, chamber 6025, between 6023 and hub 6532 (each as shown). Chamber 6024 is filled with pneumatic fluid 6022, operably joining plunger 6021 to plug 6023. When plunger 6021 is advanced and/or retracted within lumen 6011, plug 6023 advances and/or retracts in unison due to the pneumatic force imparted via pneumatic fluid 6022. In some embodiments, control rod 6533 extends through a lumen of plug 6023, for example plug 6023 can slidingly seal around control rod 6533, such that the chamber 6024 and the chamber 6025 remain fluidly isolated while plug 6023 translates within lumen 6011 relative to control rod 6533. In some embodiments, chamber 6025 is pre-filled (e.g. filled before a clinical procedure) with material 60 to be injected into the patient. Alternatively of additionally, material 60 is drawn into chamber 6025 by retracting plunger 6021 relative to hub 6532, increasing the volume of chamber 6025.

As shown in FIG. 12B, plunger 6021 and control rod 6533 can be advanced in unison, such that needles 6530 are advanced (e.g. in unison) from the distal end of shaft 6010. Needles 6530 can deflect from the central axis of device 6004 as they are advanced into tissue, as described herein. This deflection can be configured such that material 60 is delivered collectively from the multiple needles 6530 to a large volume of tissue than would be achieved without the deflection. When plunger 6021 and control rod 6533 are advanced in unison, the volume of chamber 6025 remains constant, such that material 60 remains with chamber 6025. In some embodiments, device 6004 includes a connecting element, clip 6026, that fixes the position of control rod 6533 relative to plunger 6021.

As shown in FIG. 12C, to inject material 60 via needles 6530, plunger 6021 can be advanced into lumen 6011, while the position of hub 6532 and control rod 6533 are held in position relative to lumen 6011, which causes plug 6023 to advance towards hub 6532, driving material 60 to exit from the distal end of needles 6530 (e.g. and into tissue of the patient).

Figure 13:
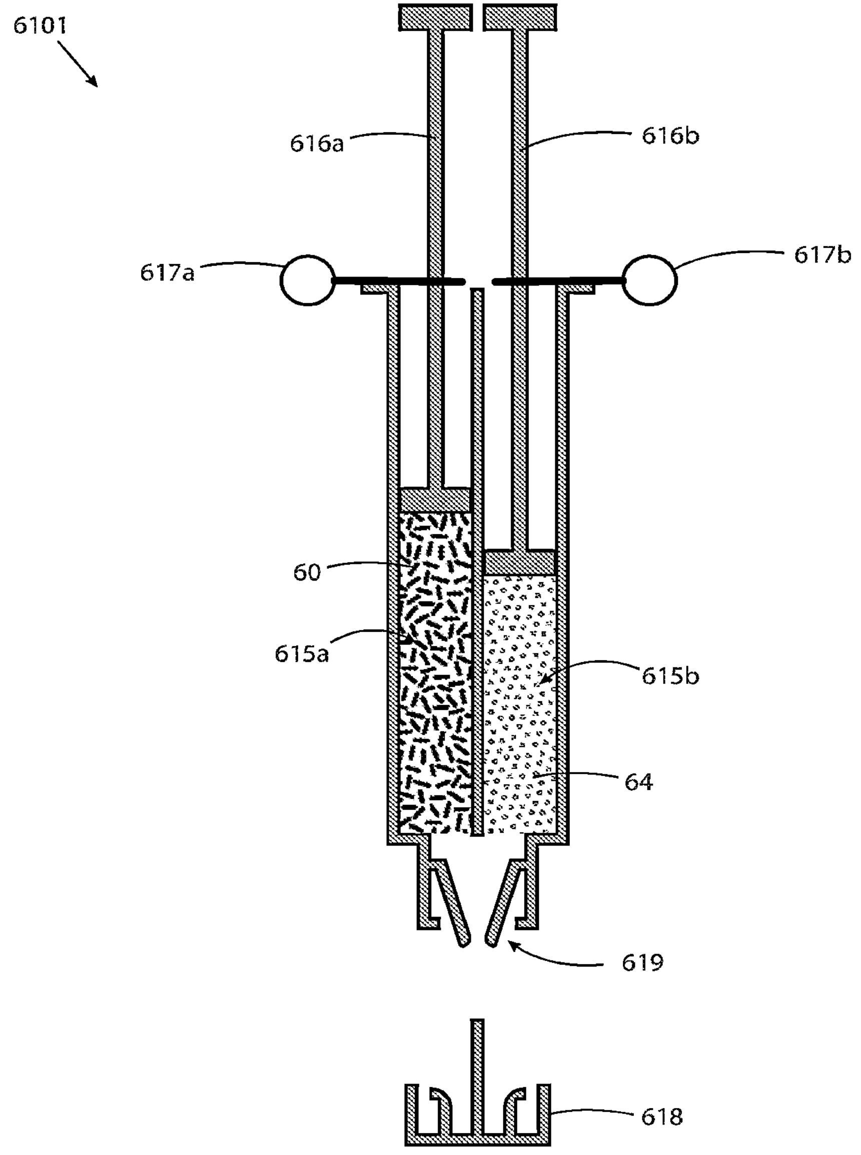
FIG. 13 illustrates a side sectional view of a syringe, consistent with the present inventive concepts.

Referring now to FIG. 13, a side sectional view of a syringe is illustrated, consistent with the present inventive concepts. Syringe 6101 of FIG. 13 can be of similar construction and arrangement to syringe 610 described in reference to FIG. 1 and otherwise herein. Syringe 6101 can comprise a multi-chamber syringe, chambers 615*a* and 615*b* shown. In some embodiments, syringe 6101 comprises three or more chambers, for example when system 10 is constructed and arranged to inject three or more materials into the patient. Chamber 615*a* can be filled (e.g. pre-filled in a manufacturing process) with material 60. Chamber 615*b* can be filled (e.g. pre-filled in a manufacturing process) with flush 64 (e.g. saline). In some embodiments, syringe 6101 operably attaches to a depositing device 600 and/or a depositing element 650 (both not shown). In some embodiments, the volume of chamber 615*b* (e.g. the volume of flush 64 held by syringe 6101), is greater than the volume of the one or more lumens or other device cavities through which material 60 travels between syringe 6101 and depositing element 650 (e.g. the "dead space"). For example, the volume of chamber 615*b* can be at least 0.5 mL, such as at least 1 mL or 2 mL.

Syringe 6101 can comprise multiple plungers, such as plungers 616*a* and 616*b* shown, that are each slidingly received within a chamber, chambers 615*a* and 615*b* respectively. In some embodiments, plungers 616*a* and 616*b* are uniquely marked (e.g. labeled) to indicate to the operator which chamber holds material 60 and which chamber holds flush 64, for example, the plungers could be different colors that indicate to the operator the contents of the chambers. During a clinical procedure, material 60 can be injected first (e.g. via depression of plunger 616*a*), followed by injection of flush 64 (e.g. via depression of plunger 616*b*). Flush 64 can force material 60 from the dead space of depositing device 600, limiting the volume of material 60 that is not fully injected into the patient. For example, syringe 6101 can be configured to inject at least 90% of material 60 into the patient by displacing material 60 from the dead space via injection of flush 64. Alternatively or additionally, flush 64 can be used to prime (e.g. fill dead space of) depositing device 600 prior to injection of material 60.

In some embodiments syringe 6101 includes one or more locking mechanism, pins 617*a,b* shown, that prevent the depression of plungers 616*a* and 616*b*, respectively. Pins 617*a,b* can be disengaged (e.g. removed) to allow plungers 616*a,b*, respectively, to be depressed. In some embodiments, pins 617*a,b* can interact with each other and/or with plungers 616*a* and/or 616*b*, such that the pins can only be disengaged in a predetermined order, for example such that pin 617*b* cannot be removed unless plunger 616*a* has been at least partially depressed. In some embodiments, syringe 6101 includes a sealing element, cap 618 shown. Cap 618 can be constructed and arranged to seal both of chambers 615*a,b*, preventing mixing of material 60 and flush 64 while cap 618 is in place. In some embodiments, syringe 6101 operably attaches to a syringe driver (not shown, but such as is described herein) that is configured to drive each plunger 616*a,b* independently.

In some embodiments, syringe 6101 includes a single output pathway, tip 619, which can be configured to attach to depositing device 600. Each chamber 615*a,b* can be operably attached (e.g. at least fluidly attached) to tip 619 (when cap 618 is removed, as shown). Alternatively, syringe 6101 can comprise multiple tips 619, such as a tip 619*a* that is operably attached (e.g. at least fluidly attached) to chamber 615*a*, and a tip 619*b* that is operably attached (e.g. at least fluidly attached) to chamber 615*b*. In these embodiments, syringe 6101 can be configured to operably attached (e.g. at least fluidly attach) to a depositing device 600 comprising multiple syringe inputs, such as multiple syringe inputs that merge via a Y-shaped manifold into a single lumen.

Figure 14A:
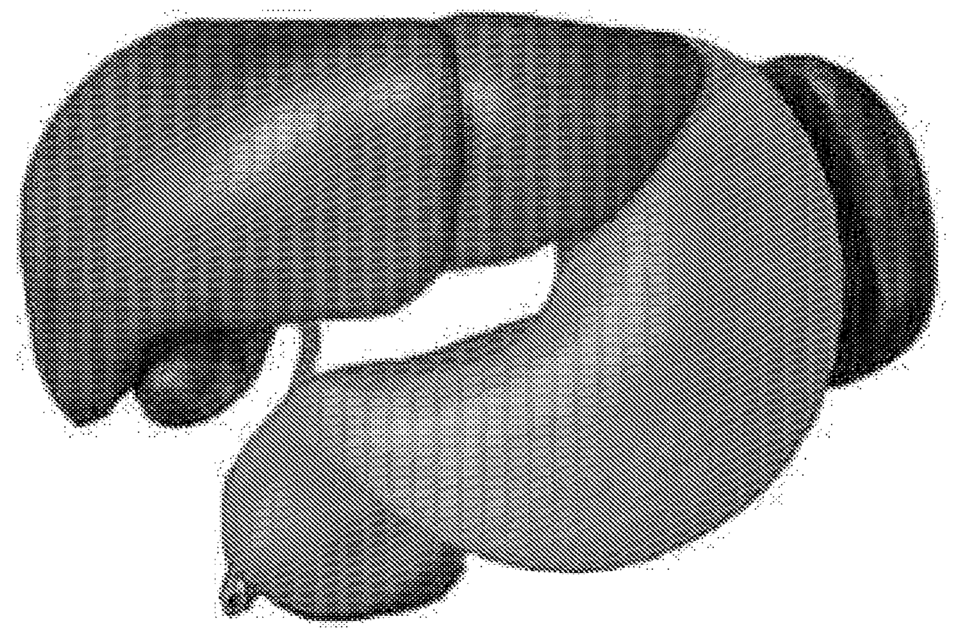
FIGS. 14A and 14B illustrate anatomical views of internal organs in various orientations, consistent with the present inventive concepts.
Figure 14B:
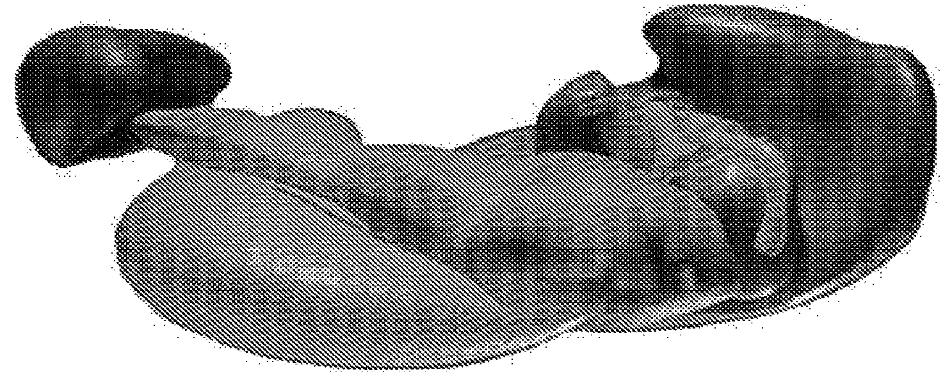

Referring now to FIGS. 14A and 14B, anatomical views of internal organs of a patient, in various orientations, are illustrated. FIG. 14A shows a model of a patient's internal organs, including the pancreas and the stomach, with the patient positioned in a standing position. FIG. 14B shows a model of the same internal organs of the patient, including the pancreas and the stomach, with the patient in a prone position. Various methods of treating a patient in the orientations shown are described in reference to FIG. 1 herein.

Referring now to FIGS. 15A-15C, side sectional views of the distal portion of a depositing device are illustrated, consistent with the present inventive concepts. Depositing device 6005 of FIGS. 15A-15C can be of similar construction and arrangement to depositing device 600 described in reference to FIG. 1 and otherwise herein. Depositing device 6005 comprises a shaft, shaft 6010, comprising at least one lumen, lumen 6011 shown. Device 6005 slidingly receives depositing element 650 through lumen 6011. Lumen 6011 can bifurcate to exit either or both of the distal end of device 6005 as well as the side of device 6005 proximate the distal end, such that depositing element 650 can be advanced to exit the side and/or the distal end of device 6005. In some embodiments, the exit path for depositing element 650 is controlled (e.g. selected) by the operator of system 10, such as via a steering cable, not shown, but configured to allow the operator to select between deflecting the distal portion of depositing element 650 towards the side exit of lumen 6011, versus allowing depositing element to exit the distal end of device 6005.

In some embodiments, lumen 6011 can comprise one or more inward protrusions, stops 6013*a,b* shown, that prevent depositing element 650 from advancing beyond a set distance from device 6005, this advancement limit representing the maximum depositing element 650 penetration depth, depth D1 shown. For example, stops 6013*a,b* can interfere with a projection (e.g. a radial projection), lip 6502, extending from depositing element 650. Stops 6013*a,b*, can be positioned at the distal ends of lumen 6011, and lip 6502 can be positioned approximately a distance D1 (e.g. less the thickness of stops 6013*a,b* and/or lip 6502) from the distal end of depositing element 650. In some embodiments, distance D1, comprises a distance of no more than 3 cm, such as no more than 2 cm, 1 cm, or 0.5 cm. In some embodiments, distance D1 is selected to allow a maximum penetration depth beyond the stomach wall (e.g. when depositing element 650 is positioned through the stomach wall into the anterior pararenal space).

Referring now to FIGS. 16A-16D, side sectional and perspective views of a depositing device are illustrated, consistent with the present inventive concepts. Depositing device 6006 of FIG. 16A can be of similar construction and arrangement to depositing device 600 described in reference to FIG. 1 and otherwise herein. Depositing device 6006 can comprise positioning assembly 6050 shown, an assembly that can be constructed and arranged to position depositing element 650 relative to shaft 6010 of device 6006, and also to control the amount of advancement of element 650 relative to shaft 6010. Assembly 6050 comprises a hollow, elongate core, hub 6051 shown, that slidingly receives a first positioner, cap 6052, and a second positioner, cap 6053. Cap 6052 can be slidingly positioned on the top portion of hub 6051 (as shown), and it can slidingly receive depositing element 650 (e.g. element 650 comprising an elongate needle including a threaded proximal hub). Depositing element 650 operably engages cap 6052, for example via a threaded engagement, such that depositing element 650 moves relative to hub 6051 in unison with cap 6052.

Assembly 6050 can include a ring, stopper 6054, which can be slidingly received on the top portion of hub 6051, and stopper 6054 can be adjustable, such as to adjust the distal-most allowable position of cap 6052 (and as such depositing element 650) relative to hub 6051. Stopper 6054 can be temporarily affixed to hub 6051, such as via a fixation element, set screw 6055 shown. In some embodiments, assembly 6050 is constructed and arranged such that cap 6052 is prevented from unintentionally moving proximally (e.g. after distal advancement) along hub 6051. Assembly 6050 can include a motion resisting element, lock 6057. In some embodiments, lock 6057 comprises a set of magnets (shown) positioned on the distal end of cap 6052 and stopper 6054, such that when cap 6052 is fully advanced (distally advanced), the magnets of lock 6057 prevent cap 6052 from retracting proximally without sufficient force being applied (e.g. by the operator) to retract cap 6052 (e.g. to overcome the magnetic force). Alternatively or additionally, lock 6057 can comprise a thumb screw configured to lock cap 6052 in an advanced position. In other embodiments, lock 6052 can comprise a ratcheting mechanism, where the ratcheting mechanism can be configured to allow advancement of cap 6057, but to prevent retraction without releasing the ratchet mechanism. In some embodiments, lock 6052 comprises a spring-loaded locking mechanism, such as a locking mechanism that prevents (or at least limits) motion of cap 6052 relative to hub 6051 in either and/or both directions unless the locking mechanism is actively released (e.g. an operator overcomes the spring force to temporarily release the lock). In some embodiments, lock 6052 provides sufficient locking force to maintain the position of cap 6052 when 6050 is held in an upside-down position.

Cap 6053 can be slidingly positioned on the bottom portion of hub 6051 (as shown), and it can slidingly receive shaft 6010, which is attached to the distal end of hub 6051. The proximal end of access device 50 (e.g. an endoscope) can operably engage cap 6053, for example via a threaded engagement, such that shaft 6010 moves relative to access device 50 (e.g. within a working channel of an endoscope) as cap 6053 moves relative to hub 6051. Cap 6053 can be temporarily affixed to hub 6051, such as via a fixation element, set screw 6056 shown.

Figures 16A, 16B, 16C, 16D:
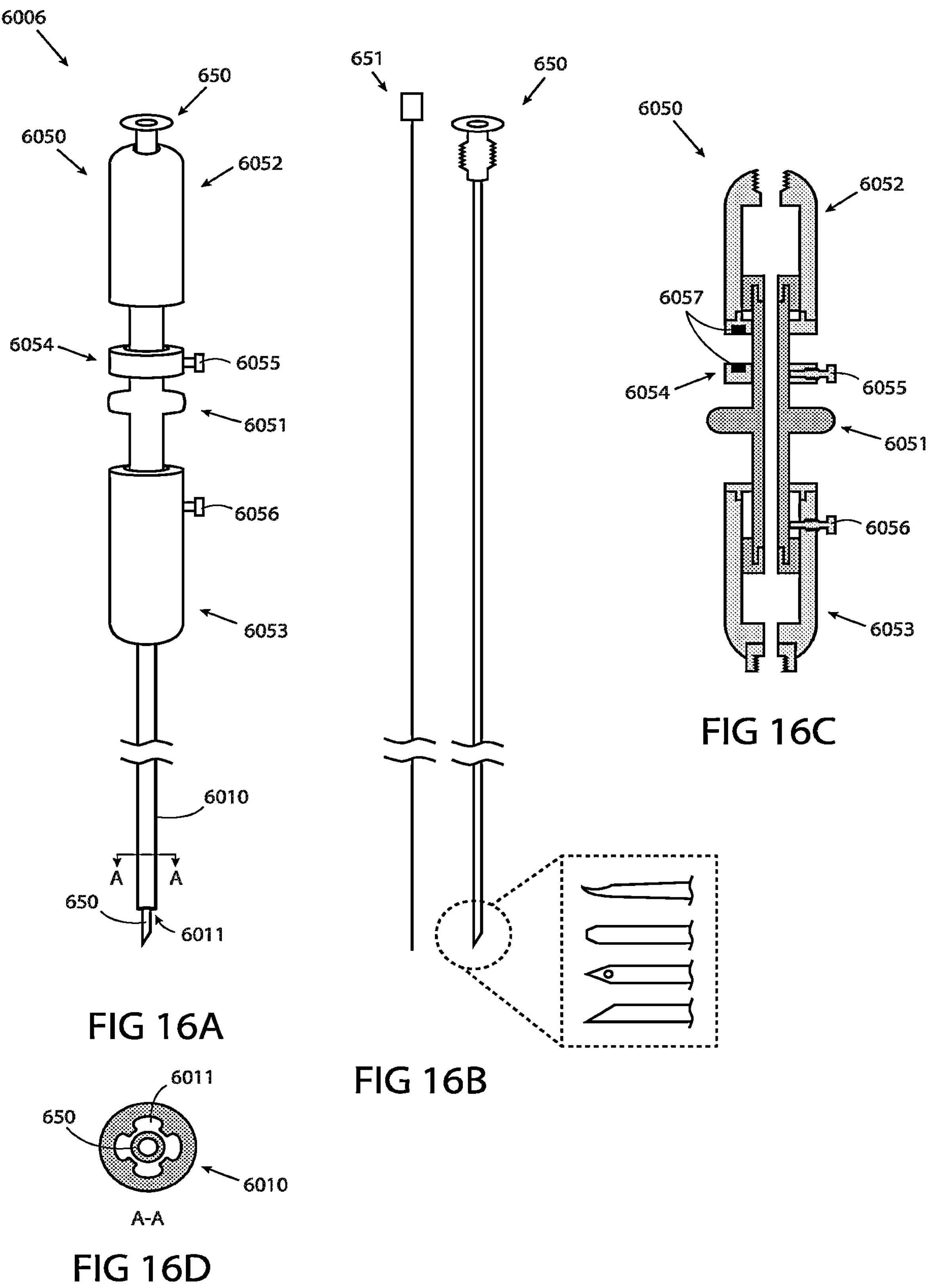
FIGS. 16A-16D illustrate sectional and perspective views of a depositing device, consistent with the present inventive concepts.

Referring specifically to FIG. 16B, the magnified portion shows various embodiments of the tip of depositing element 650.

In some embodiments, depositing device 6006 includes stylet 651 shown, which can be slidingly received within depositing element 650, for example prior to insertion of depositing element 650 into tissue. After insertion into tissue, stylet 651 can be removed to allow a material (e.g. material 60) to be injected into the patient via depositing element 650. Stylet 651 can prevent or at least limit undesired material (e.g. tissue) from entering the lumen of depositing element 650, such as while element 650 is advanced through the patient (e.g. through patient tissue). Alternatively or additionally, depositing element 650 can be primed (e.g. filled with material, such as flush 64) prior to insertion of depositing element 650 into the patient. Flush 64 can be maintained within the lumen of element 650 during insertion, preventing or at least limiting undesired material from entering the lumen of depositing element 650. In some embodiments, depositing element 650 comprises a superelastic and/or a shape memory material such as a nickel-titanium alloy or a cobalt-chromium alloy.

Referring specifically to FIG. 16D, a sectional view along section A-A of FIG. 16A is illustrated. The profile of lumen 6011 of shaft 6010 can comprise multiple inward projections along the length of the shaft 6010, as shown. These projections can be configured to center depositing element 650 within lumen 6011, such as while minimizing friction between the two by minimizing the contacting surface area between depositing element 650 and shaft 6010.

Figure 17A:
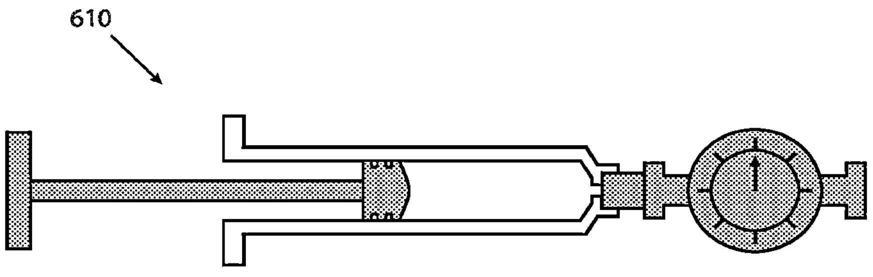
FIG. 17A illustrates a side sectional view of a syringe, consistent with the present inventive concepts.

Referring now to FIG. 17A, a side sectional view of a syringe is illustrated, consistent with the present inventive concepts. Syringe 610 of FIG. 17A can be of similar construction and arrangement to syringe 610 described in reference to FIG. 1 and otherwise herein. In some embodiments, syringe 610 includes a pressure gauge, such that the operator can monitor the pressure within the syringe. Alternatively, syringe 610 can comprise a pressure regulator configured to limit the maximum pressure syringe 610 can deliver. Monitoring and/or limiting of pressure can limit the pressure in which material 60 and/or another material is delivered into the patient.

Figure 17B:
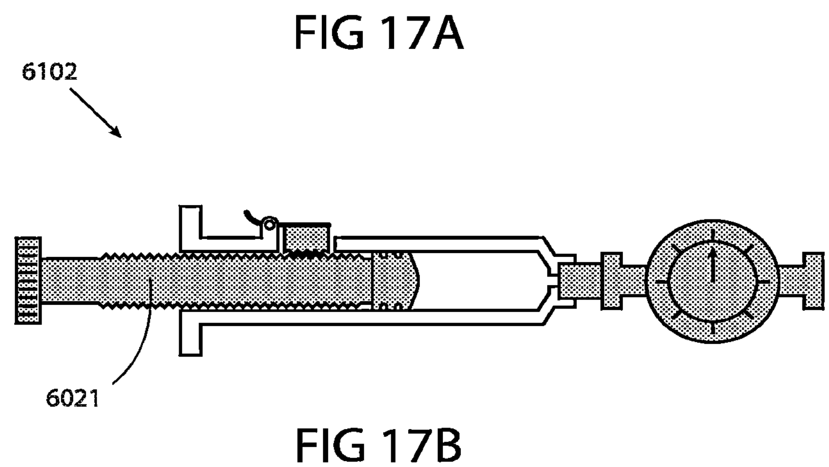
FIG. 17B illustrates a side sectional view of a syringe including a threaded plunger, consistent with the present inventive concepts.

Referring now to FIG. 17B, a side sectional view of a syringe including a threaded plunger is illustrated, consistent with the present inventive concepts. Syringe 6102 of FIG. 17B can be of similar construction and arrangement to syringe 610 described in reference to FIG. 1 and otherwise herein. Syringe 6102 can include plunger 6021. Plunger 6021 can comprise a threaded plunger that mates with threads of syringe 6102, such that plunger 6021 can be advanced and/or retracted into and/or out of syringe 6102 by rotation of plunger 6021. In some embodiments, syringe 6102 includes a quick release assembly, as shown, which can be configured to disengage plunger 6021 from the threads to allow plunger 6021 to be quickly advanced and/or retracted from syringe 6102.

Figure 17C:
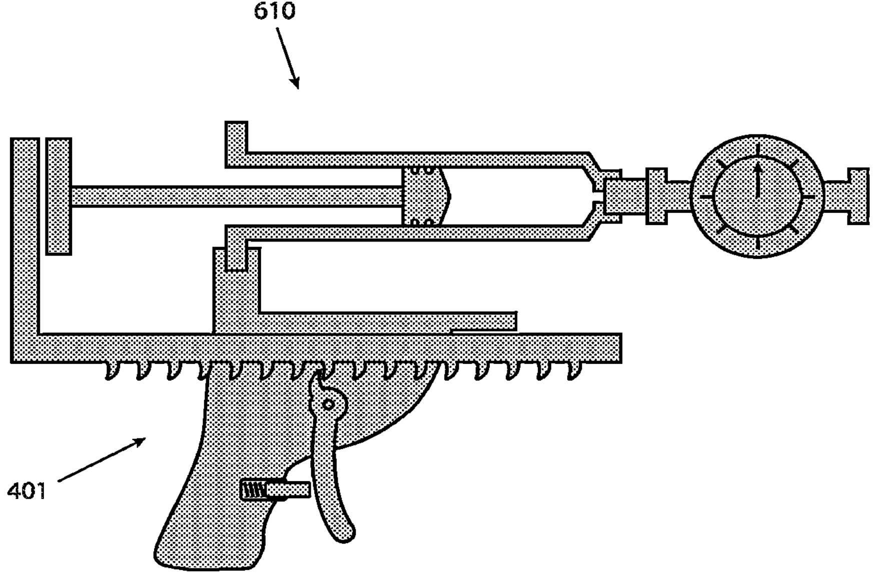
FIG. 17C illustrates a side sectional view of a syringe and a ratcheting syringe drive, consistent with the present inventive concepts.

Referring now to FIG. 17C, a side sectional view of a syringe and a ratcheting syringe drive is illustrated, consistent with the present inventive concepts. Syringe 610 and syringe drive 401 of FIG. 17C can be of similar construction and arrangement to syringe 610 and syringe drive 40, respectively, described in reference to FIG. 1 and otherwise herein. Syringe drive 401 can comprise a ratcheting syringe drive, as shown.

Figure 17D:
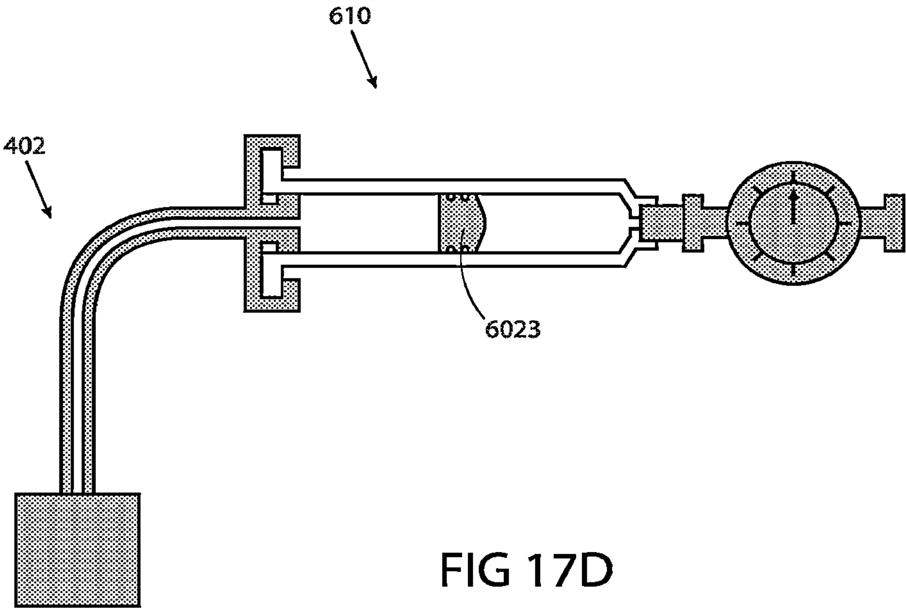
FIG. 17D illustrates a side sectional view of a syringe and a pressurized syringe drive, consistent with the present inventive concepts.

Referring now to FIG. 17D, a side sectional view of a syringe and a pressurized syringe drive is illustrated, consistent with the present inventive concepts. Syringe 610 and syringe drive 402 of FIG. 17D can be of similar construction and arrangement to syringe 610 and syringe drive 40, respectively, described in reference to FIG. 1 and otherwise herein. Syringe drive 402 can comprise a pressure source, which can be configured to operably attach to syringe 610 to provide a pressurized fluid (e.g. gas) to drive plug 6023 through syringe 610, as shown.

Figure 17E:
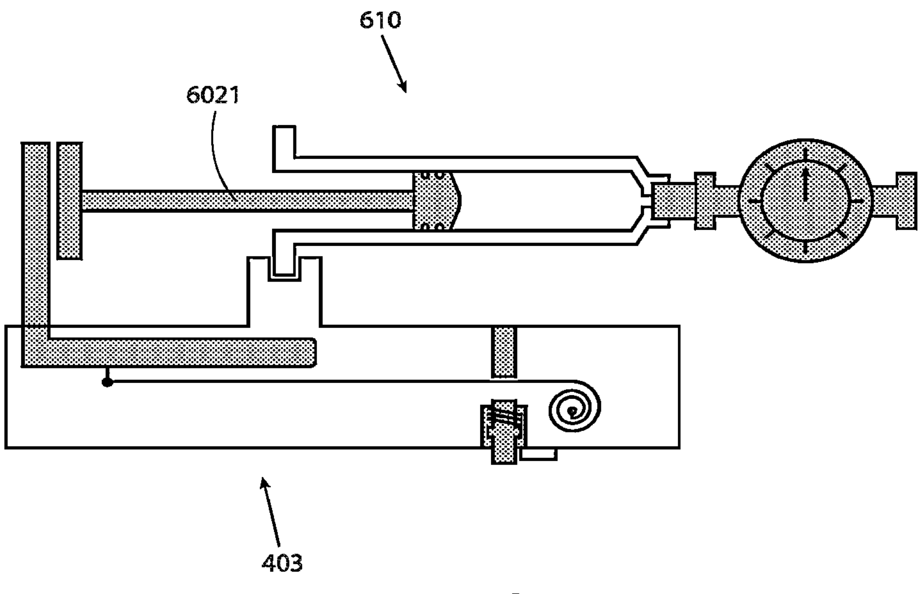
FIG. 17E illustrates a side sectional view of a syringe and a syringe drive comprising a spring, consistent with the present inventive concepts.

Referring now to FIG. 17E, a side sectional view of a syringe and a syringe drive comprising a spring is illustrated, consistent with the present inventive concepts. Syringe 610 and syringe drive 403 of FIG. 17E can be of similar construction and arrangement to syringe 610 and syringe drive 40, respectively, described in reference to FIG. 1 and otherwise herein. Syringe drive 403 can comprise a spring (e.g. a constant force spring) configured to apply a force to plunger 6021 to drive plunger 6021 into syringe 610, as shown.

Figure 18:
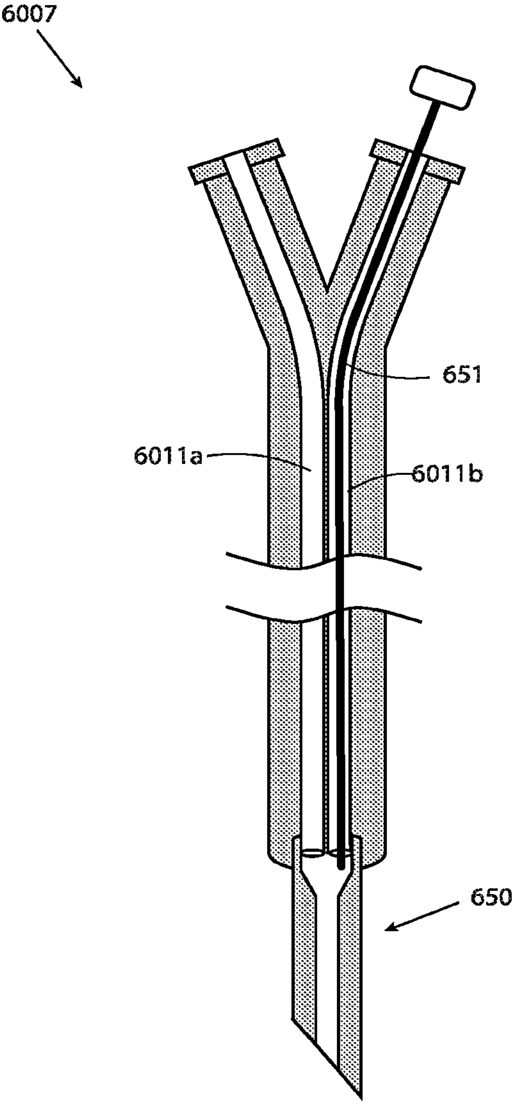
FIG. 18 illustrates a side sectional view of a portion of a dual lumen depositing device, consistent with the present inventive concepts.

Referring now to FIG. 18, a side sectional view of a portion of a dual lumen depositing device is illustrated, consistent with the present inventive concepts. Depositing device 6007 of FIG. 18 can be of similar construction and arrangement to depositing device 600 described in reference to FIG. 1 and otherwise herein. Depositing device 6007 can comprise shaft 6010 including a first lumen 6011*a* and a second lumen 6011*b*. Lumens 6011*a,b* can each be operably attached (e.g. at least fluidly attached) to depositing element 650 as shown. Depositing device 6007 can include stylet 651, that can be inserted into a lumen of device 6007 (e.g. lumen 6011*b* as shown). Stylet 651 can provide support (e.g. to increase trackability and/or to prevent kinking) to depositing device 6007.

In some embodiments, prior to insertion into a patient, lumen 6011*a* is filled with a material (e.g. flush 64) and lumen 6011*b* slidingly receives stylet 651. After insertion, to prevent or at least limit undesired material (e.g. tissue) from being drawn into depositing element 650, additional material (e.g. flush 64 or material 60) can be injected into lumen 6011*a* while stylet 651 is retracted from lumen 6011*b* (e.g. to relieve any vacuum pressure created during the removal of stylet 651). In some embodiments, the vacuum created by the removal of stylet 651 can be used advantageously, for example by drawing a priming material (e.g. flush 64) in a proximal direction into lumen 6011*b*, while material 60 is injected into lumen 6011*a*. In these embodiments, the volume of priming material injected into the patient prior to material 60 can be minimized. In some embodiments, stylet 651 includes a distal portion configured to seal with the inner walls of lumen 6011*a* to increase the vacuum pressure created when stylet 651 is retracted.

Figures 19, 19A, 19B, 19C, 19D, 19E:
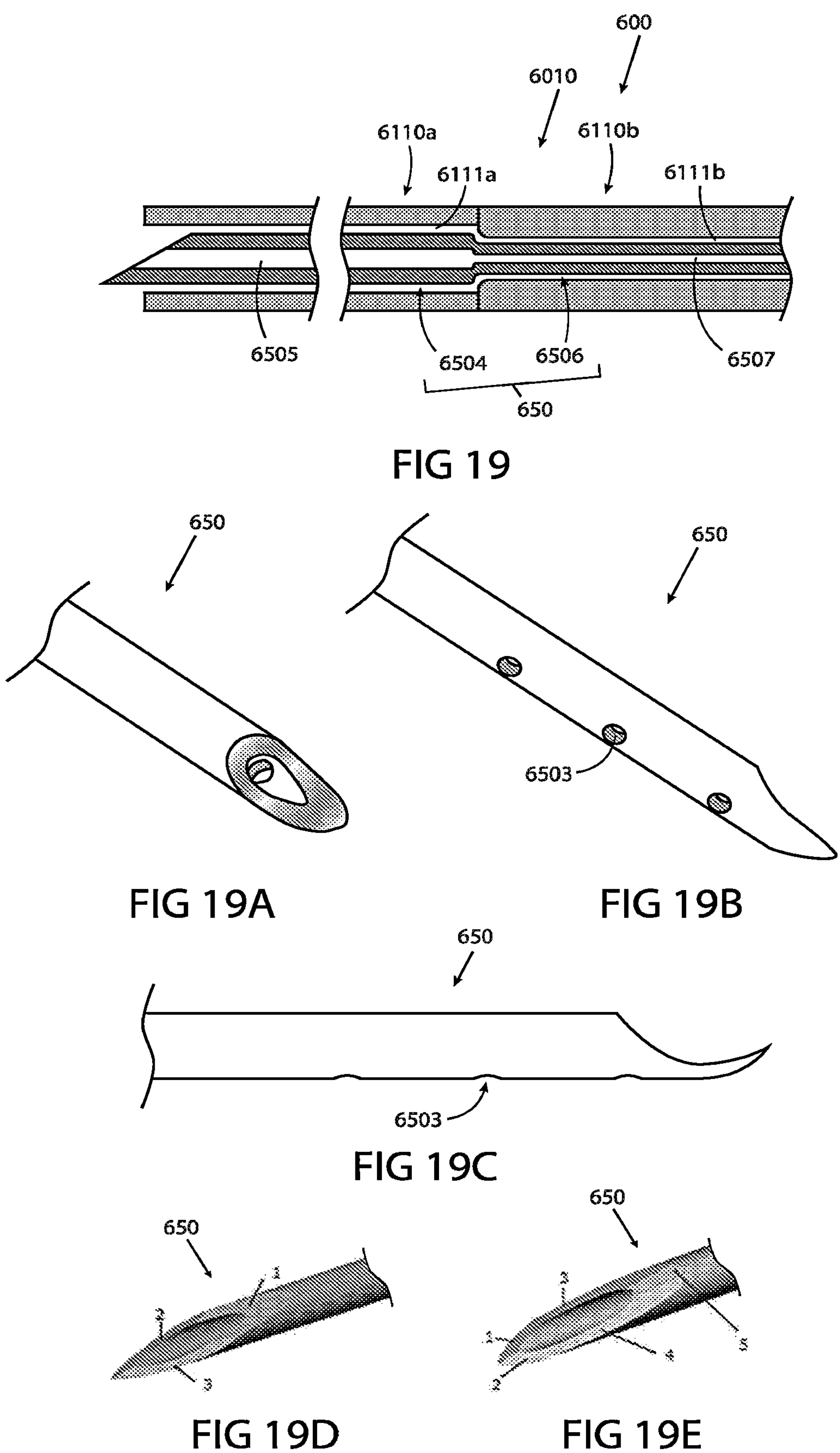
FIG. 19 illustrates a side sectional view of the distal portion of a depositing device, consistent with the present inventive concepts.
FIGS. 19A-19C illustrate two perspective views and a side view of the distal portion of a depositing element, respectively, consistent with the present inventive concepts.
FIGS. 19D-19E illustrate two perspective views of the distal portion of a depositing element, consistent with the present inventive concepts.

Referring now to FIG. 19, a side sectional view of the distal portion of a depositing device is illustrated, consistent with the present inventive concepts. Depositing device 600 of FIG. 19 can be of similar construction and arrangement to depositing device 600 described in reference to FIG. 1 and otherwise herein. In some embodiments, depositing device 600 is constructed and arranged to deliver one or more materials (e.g. material 60 and/or flush 64) into the pancreas or other body location of a patient. Depositing device 600 comprises shaft 6010 comprising a two-part construction including distal portion 6110*a* and proximal portion 6110*b*, as shown. Distal portion 6110*a* comprises first lumen 6111*a* comprising a first diameter, and proximal portion 6110*b* comprises a second lumen 6111*b* comprising a second diameter (e.g. larger or otherwise different than the first diameter as shown). In some embodiments, shaft 6010 comprises a unitary construction with a variable diameter lumen therethrough. Alternatively, shaft 6010 can comprise a multipart construction, where distal portion 6110*a* and proximal portion 6110*b* are joined to form a single shaft, such as via a butt weld or other adhesive bonding technique (e.g. with glue).

Depositing device 600 can comprise depositing element 650. Depositing element 650 can comprise a multi-part construction, such as a two-part construction comprising a distal portion, tip 6504, and a proximal portion, shaft 6506. Shaft 6506 can comprise lumen 6507 therethrough. Tip 6504 can comprise lumen 6505 therethrough. In some embodiments, shaft 6506 comprises a silica needle shaft, such as a shaft configured as a fused silica capillary tube. In some embodiments, shaft 6506 comprises fused silica lined with PEEK tubing. Silica tubing can comprise a smooth surface (e.g. smoother than a standard stainless steel needle), to which material 60 is less likely to stick, and which would provide less fluid resistance than other materials, such as stainless steel or other metal materials. In some embodiments, tip 6504 comprises a stainless steel needle fixedly attached to the distal end of shaft 6506. In some embodiments, depositing element 650 comprises an adapter (not shown) configured to attach tip 6504 to shaft 6506.

Referring additionally to FIGS. 19A-19C, two perspective views and a side view of the distal portion of a depositing element are illustrated, respectively, consistent with the present inventive concepts. In some embodiments, the distal portion of depositing element 650 comprises tip 6504 described hereabove. Depositing element 650 can comprise an anti-coring distal end, as shown. Additionally or alternatively, depositing element 650 can comprise a fenestrated needle comprising one or more openings, such as three openings 6503 shown, positioned through the wall of the distal portion of depositing element 650. Openings 6503 can comprise one, two, three or more elongate openings that are oriented along the axis of tip 6504 and/or orthogonal to the axis of tip 6504. In some embodiments, depositing element 650 comprises a closed distal end (not shown), for example such that all material deposited through depositing element 650 is delivered via openings 6503. In some embodiments, the distal most opening 6503 is positioned within 2 mm of the distal end of depositing element 650, such as within 1 mm, or within 0.5 mm. In some embodiments, openings are spaced at least 0.5 mm apart, such as at least 1 mm apart. In some embodiments, the proximal most opening 6503 is positioned within 2 cm of the distal end of depositing element 650, such as within 1.5 cm, within 1 cm, or within 0.75 cm.

Referring additionally to FIGS. 19D-E, two perspective views of the distal portion of a depositing element are illustrated, consistent with the present inventive concepts. In some embodiments, the distal portion of depositing element 650 comprises tip 6504 described hereabove. In some embodiments, depositing element 650 comprises a multi-bevel tip, such as a three-bevel tip as shown in FIG. 19D, and/or a five-bevel tip as shown in FIG. 19E. In some embodiments, depositing element 650 comprises an offset bevel.

Figure 20A:
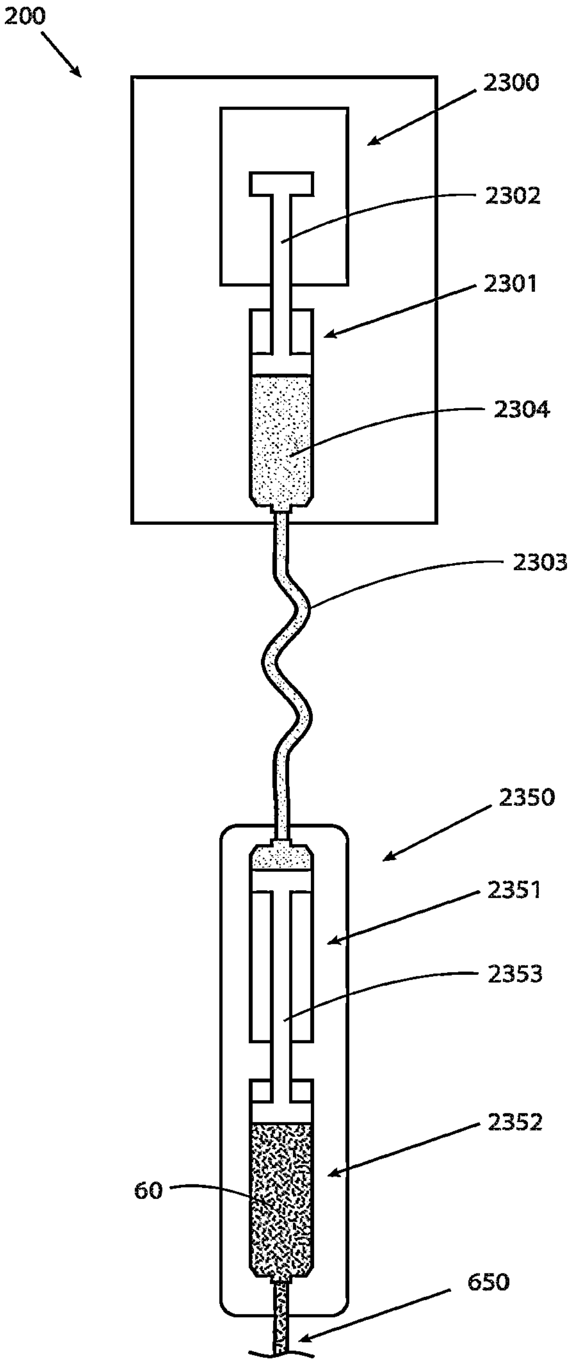
FIGS. 20A and 20B illustrate schematic views of two syringe drive assemblies, consistent with the present inventive concepts.
Figure 20B:
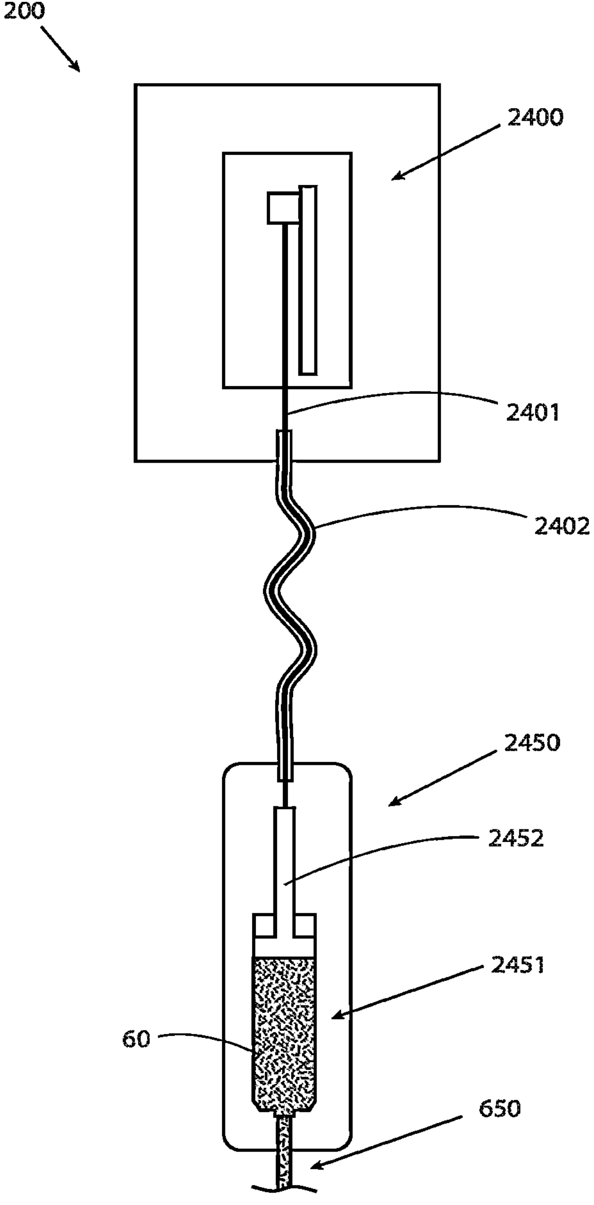

Referring now to FIGS. 20A and 20B, schematic views of two syringe drive assemblies are illustrated, consistent with the present inventive concepts. FIG. 20A shows a hydraulic syringe drive configured to transfer linear motion between console 200 and a syringe adapter using hydraulics. FIG. 20 B shows a linkage syringe drive configured to transfer linear motion between console 200 and a syringe adapter using a push rod.

FIG. 20A shows console 200 including a first syringe drive assembly, drive 2300, including a first syringe 2301 and first plunger 2302, each as shown. Drive assembly 2300 is configured to translate first plunger 2302 into and/or out of first syringe 2301. Drive 2300 is operably attached (e.g. at least fluidly attached) to a mechanism configured to translate the applied force to a syringe, syringe adapter 2350 shown. Drive 2300 is operably attached (e.g. at least fluidly attached) to syringe adapter 2350 via a tube, tube 2303. In some embodiments, tube 2303 comprises a non-compliant, flexible material, such as fused silica. In some embodiments, drive assembly 2300 comprises a stepper motor.

Syringe adapter 2350 can include a second syringe 2351 and a third syringe 2352, which can be positioned "back-to-back" with each other as shown. A second plunger, plunger 2353 can be positioned between syringes 2351 and 2352 as shown. In some embodiments, second plunger 2353 comprises two separate elongate members that are mechanically fixed to each other (e.g. via a clip), where the fixation allows both delivery of material 60 from third syringe 2352 as well as filling of third syringe 2352. In some embodiments, the two separate elongate members are not mechanically fixed to each other, such that only delivery of material 60 from third syringe 2352 can be performed (e.g. push only). Drive 2300 can comprise hydraulic fluid 2304, positioned within a closed hydraulic system between syringe 2301, tube 2303, and syringe 2351. Plunger 2353 can be configured to actuate within syringe 2351 as fluid 2304 is manipulated within the hydraulic system by plunger 2302 (e.g. as plunger 2302 drives fluid 2304 through tube 2303 into syringe 2351, plunger 2353 is driven through syringe 2351, into syringe 2352). As plunger 2353 is driven into and/or retracted from syringe 2352, material 60 can be delivered from and/or drawn into syringe 2352, respectively (e.g. via depositing element 650 operably attached (e.g. at least fluidly attached) to syringe 2352). In some embodiments, syringes 2301, 2351, and 2352 can comprise different size syringes (e.g. different diameter syringes), such as to provide a hydraulic advantage.

FIG. 20B shows console 200 including a linear drive assembly, drive 2400, which can be configured to advance and/or retract an elongate filament, linkage 2401 shown. Linkage 2401 extends through a flexible conduit, conduit 2402 shown, that extends between console 200 and a mechanism configured to translate force applied to linkage 2401 to a syringe, syringe adapter 2450 shown. Conduit 2402 can comprise a length sufficient to position drive 2400 a desired distance from syringe adapter 2450, such as when conduit 2402 comprises a length of at least 10 cm. Syringe adapter 2450 can include syringe 2451, and plunger 2452, each as shown. Conduit 2402 can be fixedly attached to the proximal portion of syringe adapter 2450 relative to syringe 2451, and linkage 2401 can be fixedly attached to plunger 2452, such that as linkage 2401 is advanced from and/or retracted into conduit 2402, plunger 2452 is advanced and/or retracted from syringe 2451. As plunger 2452 is advanced and/or retracted from syringe 2451, material 60 can be delivered from and/or drawn into syringe 2451, respectively (e.g. via depositing element 650 that is at least fluidly attached to syringe 2451). In some embodiments, drive 2400 comprises one or more guide elements, not shown, which can be configured to maintain linkage 2401 in a linear arrangement when extended proximally from conduit 2402. In some embodiments, conduit 2402 comprises a low-friction flexible tube. Alternatively or additionally, conduit 2402 can comprise a telescoping proximal and/or distal portion configured to prevent or at least limit buckling of linkage 2401. In some embodiments, linkage 2401 comprises a superelastic material, such as a nickel titanium alloy.

In some embodiments, syringe drive 2300 and/or linear drive 2400 can comprise a load cell, and the load cell can be configured to monitor the pressure being applied to the syringe containing material 60 (syringes 2352 or 2451, respectively), such as to measure, monitor, control, and/or limit the pressure in which material 60 is delivered to a deposit site.

Figure 21:
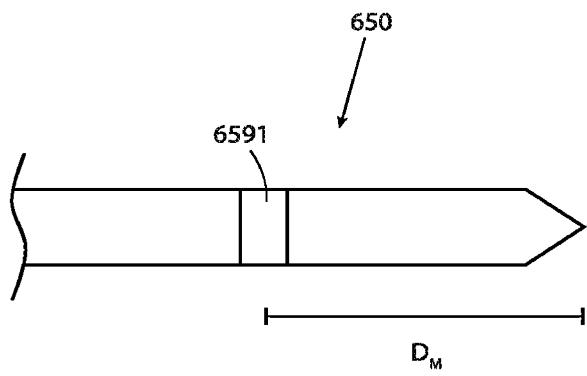
FIGS. 21 and 21A illustrate side views of the distal end of two depositing elements, consistent with the present inventive concepts.

Referring now to FIG. 21, a side view of the distal end of a depositing element is illustrated, consistent with the present inventive concepts. Depositing element 650 can be similar to depositing element 650 described herein. Depositing element 650 can comprise one or more visualizable elements, marker 6591 shown. Marker 6591 can be positioned a distance $D_M$ from the distal end of depositing element 650. Marker 6591 can comprise a visualizable marker, such as a marker that can be visualized by an imaging device of system 10, such as imaging device 90 described herein. For example, marker 6591 can be configured to be visualized via an ultrasound imaging device and/or an X-ray based imaging device, such as to be visualized under fluoroscopy. In some embodiments, marker 6591 comprises a radiopaque marker. In some embodiments, marker 6591 comprises a hyperechogenic material configured to imaged brightly under ultrasonic imaging. Alternatively, marker 6591 can comprise a hypoechogenic material configured to image darkly (e.g. provide little or no ultrasonic reflection) under ultrasonic imaging. In some embodiments, marker 6591 comprises an elongate hollow shaft positioned between a proximal portion of depositing element 650 and the distal tip of depositing element 650. For example, marker 6591 can comprise a plastic segment positioned between two non-plastic segments of depositing element 650 (e.g. two non-plastic segments comprising a stainless steel or silica proximal segment and a stainless-steel needle distal tip segment). In some embodiments, marker 6591 comprises a double walled elongate hollow shaft, where the space between the walls comprises a vacuum (e.g. a thermos-like construction) or the spaces comprises another image-enhancing or otherwise imaging-affecting material (e.g. a material other than air).

Figure 21A:
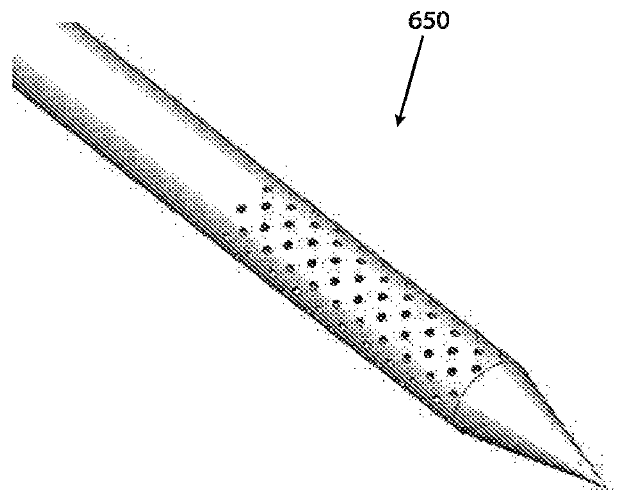

Referring additionally to FIG. 21A, a side view of the distal end of another depositing element is illustrated, consistent with the present inventive concepts. Depositing element 650 can be similar to depositing element 650 described in reference to FIG. 1 and otherwise herein. Depositing element 650 can comprise a mesh-like tip (as shown), such as a construction comprising a plurality of holes (e.g. laser drilled holes) forming a mesh opening that extends from a lumen of depositing element 650. In some embodiments, depositing element 650 comprises a closed distal end, as shown. The mesh-like tip shown can be configured to enhance echogenicity and/or to improve delivery of material 60 or another material to tissue, such as to cause the delivered material to be delivered to a larger volume of tissue than would result with the material exiting a single (e.g. distal) opening of depositing element 650.

Figure 22:
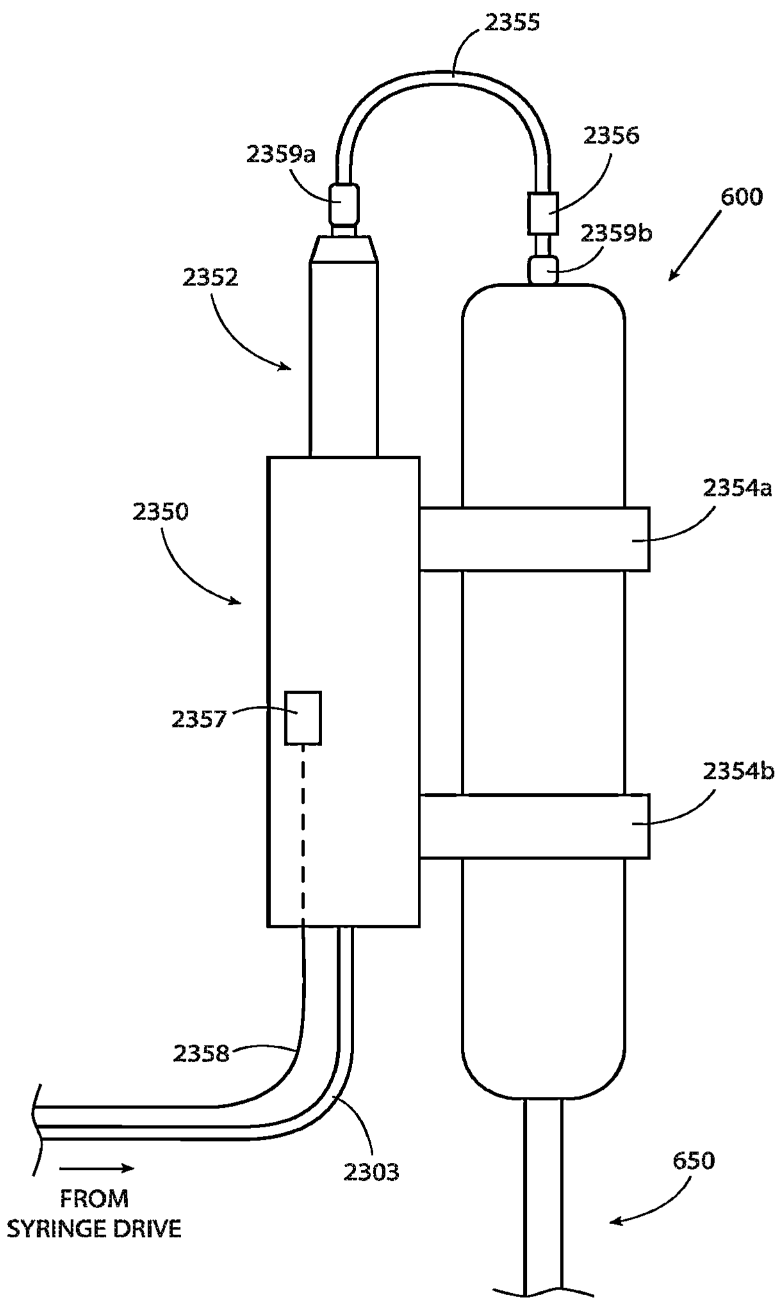
FIG. 22 illustrates a side view of a syringe adaptor attached to a depositing device, consistent with the present inventive concepts.

Referring now to FIG. 22 a side view of a syringe adaptor attached to a depositing device is illustrated, consistent with the present inventive concepts. As described herein, system 10 can comprise a syringe drive, which can be similar to one or more of drives 40, 2300, and/or 2400 described herein, and can fluidly attach to a syringe adapter, such as syringe adaptor 2350 shown in FIG. 22. Syringe adaptor 2350 of FIG. 22 can be of similar construction and arrangement as syringe adaptor 2350 described in reference to FIG. 20A herein. Syringe adaptor 2350 can comprise a tube 2303 that is operably attached (e.g. at least fluidly attached) to the syringe drive (e.g. syringe drive 2300 described in reference to FIG. 21A herein). Syringe adapter 2350 can comprise one or more attachment mechanisms, clips 2354*a,b* shown, that removably attach adapter 2350 to a depositing device, depositing device 600 shown. In some embodiments, clips 2354*a,b* comprise snap fitting configured to "snap" (e.g. a snap providing audible and/or tactile feedback of a secure connection) onto depositing device 600. Alternatively or additionally, syringe adaptor 2350 and depositing element 600 can each comprise projections (e.g. mushroom shaped projections) and/or mating keyhole slots, such as when the slots slidingly and lockingly engage the projections. In some embodiments, syringe adaptor 2350 and depositing device 600 each comprise mating magnetic materials (e.g. mating magnets or a magnet and a magnetic material) configured to removable attach syringe adapter 2350 to depositing device 600 using magnetic forces.

Depositing device 600 can be operably attached (e.g. at least fluidly attached) to depositing element 650, such as is described herein. In some embodiments, syringe adapter 2350 is removably attached to depositing device 600 such that the distal end of syringe 2352 is positioned upward (relative to the page), opposite the distal end of depositing device 600. Syringe adaptor 2350 can comprise a fluid connector, tube 2355 shown, that fluidly connects syringe 2352 to depositing element 650 (e.g. via depositing device 600). Tube 2355 can be configured to redirect flow (e.g. approximately 180°) from syringe 2352 into depositing device 600. In some embodiments, tube 2355 comprises a length of no more than 10 cm, such as no more than 8 cm. In some embodiments, tube 2355 includes a fluid control element, valve 2356 shown. Valve 2356 can allow the operator to control (e.g. prevent or allow) the flow of fluid (e.g. material 60) into depositing element 650. Valve 2356 can be used to prevent or at least limit leakage or other egress ("leakage" or "egress" herein) of fluid from depositing element 650 (e.g. after depositing element 650 is primed as described herein), and/or to prevent accidental injection of material 60 via depositing element 650 into the patient. In some embodiments, tube 2355 includes one or more connectors, two connectors 2359*a,b* shown, that operably attach to syringe 2352 and depositing device 600 (connectors 2359*a* and 2359*b*, respectively). In some embodiments, one or more of connectors 2359 comprise self-sealing connectors (e.g. connectors that comprise one or more valves and/or sealing elements) that prevent or at least limit flow through the connector when a mating connector is not attached (e.g. a self-sealing luer type connector that is sealed while a mating luer connector, such as that on the end of a syringe, is not connected), such as to prevent material 60 from undesirably exiting device 600.

In some embodiments, syringe adaptor 2350 comprises one or more operator controls, switch 2357 shown. Switch 2357 can be operably (e.g. electrically) connected to a syringe drive of console 200 (not shown but described herein) via a conduit including one or more wires, wire 2358 shown. Switch 2357 can be configured to allow the operator to start and/or stop injection via depositing element 650 by starting and/or stopping the operation of the syringe drive (e.g. via a control signal and/or by supplying and/or interrupting power to the drive). In some embodiments, a syringe drive of console 200 comprises an electromagnetic drive mechanism (e.g. a mechanism including a solenoid) configured to drive and/or retract a plunger into a syringe. Switch 2357 can be operably connected to activate the electromagnetic drive mechanism. Alternatively or additionally, switch 2357 can provide a signal to a controller (e.g. processing unit 210 not shown but described herein), such that the controller can activate the electromagnetic drive mechanism in response to the signal from switch 2357.

Figure 23:
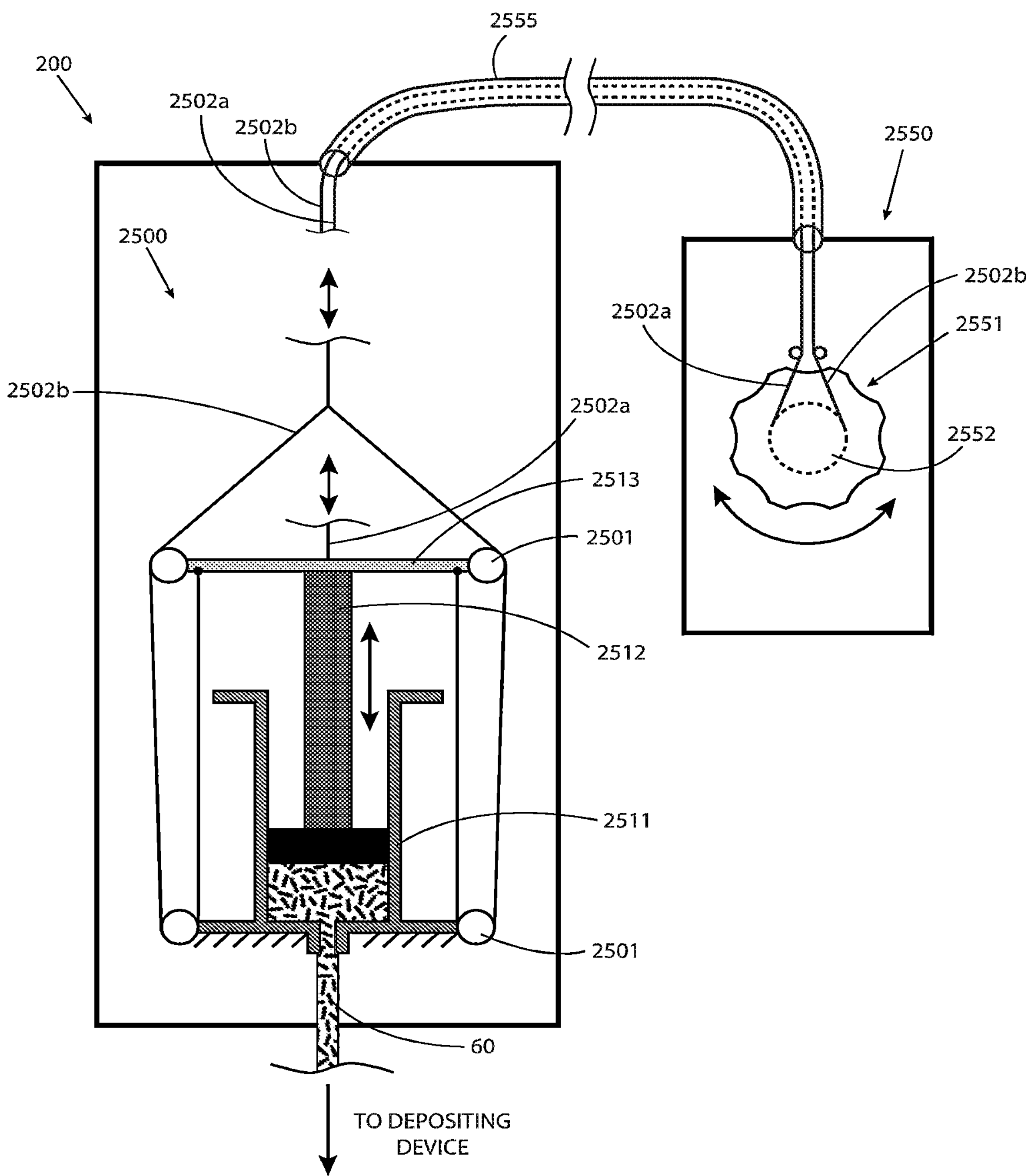
FIG. 23 illustrates a schematic view of a syringe drive assembly, consistent with the present inventive concepts.

Referring now to FIG. 23, a schematic view of a syringe drive assembly is illustrated, consistent with the present inventive concepts. Console 200 can include an assembly for driving a syringe plunger, syringe drive assembly 2500 shown. Console 200 can be similar to console 200 described in reference to FIG. 1 and otherwise herein. Syringe drive assembly 2500 can comprise syringe 2511 that can be fixedly attached (e.g. removably attached via one or more clips or other retention mechanisms) to console 200. Syringe drive assembly 2500 can include plunger 2512, which can be slidingly received within syringe 2511, such that plunger 2512 is advanced and/or retracted within syringe 2511, such that fluid (e.g. material 60 shown) is delivered from and/or drawn into syringe 2511. Syringe 2511 can be operably attached (e.g. at least fluidly attached) to a depositing element (e.g. depositing element 650 described herein), such that material 60 can be delivered to a patient via the depositing element by advancing plunger 2512 into syringe 2511.

Syringe drive assembly 2500 can comprise a set of components configured to enable an operator of system 10 to remotely (e.g. via one or more mechanical linkages, as shown, and/or via electromechanical signals and devices) advance and/or retract plunger 2512. For example, as shown, syringe drive assembly 2500 can comprise a system of linkages and pulleys configured to advance and/or retract plunger 2512 as the operator actuates a control knob attached to the linkages (as described herebelow). Alternatively or additionally, a syringe drive assembly can comprise one or more electromechanical drive mechanisms configured to advance and/or retract plunger 2512 in response to a control signal received from the operator (e.g. received from console based on actions performed by the operator).

Syringe drive assembly 2500 can include a control assembly, control assembly 2550 shown, that can include one or more user actuatable devices, control knob 2551 shown. Control knob 2551 can rotate about a central hub, hub 2552 shown. Syringe drive assembly 2500 can include one or more linkages, cable 2502 shown. Cable 2502 can loop about hub 2552, and extend through a channel, conduit 2555, such as a flexible, fixed length conduit configured to maintain tension in cable 2502 between control assembly 2550 and console 200. In some embodiments, conduit 2555 is a portion of an umbilical assembly of system 10, such as a bundle of two or more conduits, wires, fluid tubes, and/or other elongate components that operably attach (e.g. fluidly, electrically, pneumatically, hydraulically, optically, and/or acoustically attach) console 200 to depositing device 600. In some embodiments, conduit 2555 comprises a multi-lumen extrusion (e.g. including a lumen for each cable portion 2502*a,b*). In some embodiments, handle 601 (not shown) of depositing device 600 comprises at least a portion of control assembly 2550 (e.g. handle 601 comprises one or more switches, levers, knobs, and/or other operator controls of control assembly 2550). Cable 2502 can be attached to hub 2552, such that as knob 2551 is rotated in a first direction, a first portion of cable 2502, cable portion 2502*a*, is pulled and a second portion of cable 2502, cable portion 2502*b*, is released. When knob 2551 is rotated in an opposite, second direction, cable portion 2502*b* is pulled, and cable portion 2502*a* is released. In some embodiments, cable portions 2502*a,b* comprise separate cables.

Plunger 2512 can comprise an attachment portion, control bar 2513, that attaches to the ends of cable portions 2502*a,b*. For example, as shown, cable portion 2502*a* can attach to the top (as shown on the page) of control bar 2513, such when cable portion 2502*a* is retracted (e.g. into conduit 2555), plunger 2512 is retraced from syringe 2511. In some embodiments, cable portion 2502*b* is split into multiple segments, two shown, engages a system of one or more pulleys, pulleys 2501, and attaches to the bottom of control bar 2513. In this configuration, when cable portion 2502*b* is retracted (e.g. into conduit 2555), plunger 2512 is pulled into syringe 2511. In some embodiments, as shown, cable portion 2502*b* attaches to opposite sides of control bar 2513 to prevent or at least limit twisting forces that may be applied to plunger 2512 if unbalanced forces were applied to advance plunger 2512 (e.g. if cable portion 2502*b* did not split and attached to one side of control bar 2513. In some embodiments, syringe 2511 comprises a standard syringe, for example a standard, commercially available syringe that can be adapted for use with system 10, where console 200 is configured to attach to syringe 2511 and control bar 2513 is configured to fixedly attach to syringe 2511. Alternatively or additionally, syringe 2511, plunger 2512, and control bar 2513 can comprise components integral to and/or specifically designed for use with syringe drive assembly 2500. In some embodiments, syringe drive assembly 2500 and/or control assembly 2550 each comprise one or more housings, covers, and/or other protective elements configured to prevent an operator from being injured during the operation of syringe drive assembly 2500 (e.g. by protecting and/or eliminating any "pinch points"). In some embodiments, syringe drive assembly can comprise a lid (e.g. a portion of a housing comprising a lit) that is removably attachable and/or held in place with twistable tabs. In the embodiments, the lid can be removed and/or opened such that the mechanisms of syringe drive assembly 2500 can be accessible to the operator.

Figure 23A:
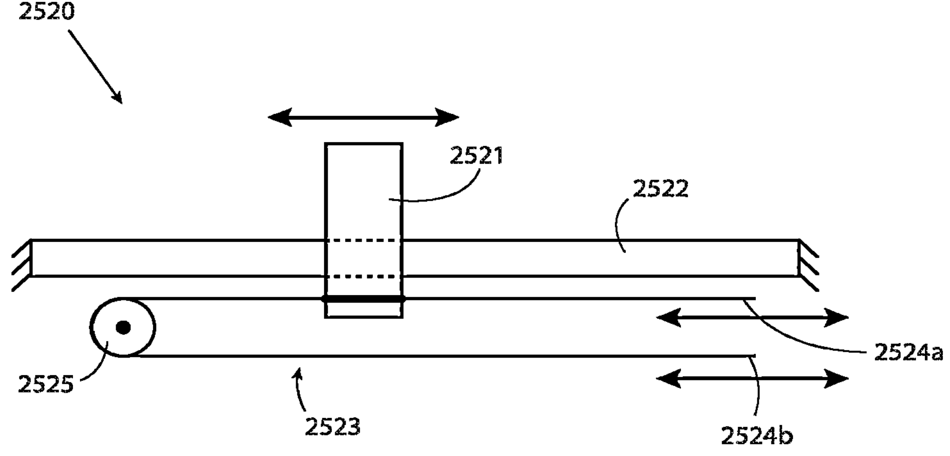
FIGS. 23A-23B illustrate schematic views of remotely actuated linear drive assemblies, consistent with the present inventive concepts.
Figure 23B:
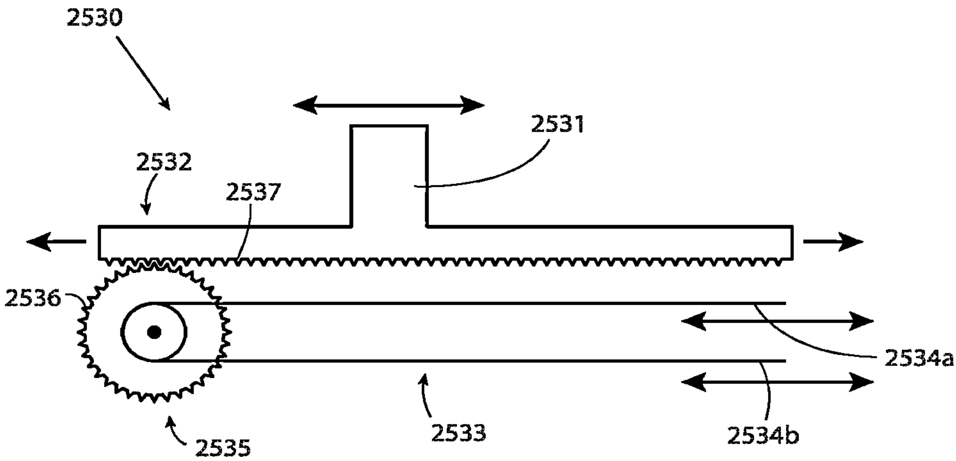

Referring additionally to FIGS. 23A and 23*b*, schematics view of various remotely actuated linear drive assemblies are illustrated, consistent with the present inventive concepts. In some embodiments, syringe drive assembly 2500 comprises control assembly 2550 operably attached to console 200 via conduit 2555, and one or more linkages extend through conduit 2555 from control assembly 2550 and console 200. In some embodiments, syringe drive assembly 2500 comprises a linear drive assembly, such as linear drive assemblies 2520 and/or 2530 shown in FIGS. 23A and 23B, respectively.

Drive assembly 2520 includes a translating component, cart 2521, that attaches (e.g. removably attaches) to a plunger of a syringe (not shown), such that as cart 2521 advances and/or retracts (e.g. advances to the left as shown on the page), the plunger advances and/or retracts. Cart 2521 can be slidingly positioned on a linear guide, rail 2522, that is fixedly positioned relative to other fixed components of drive assembly 2520 (e.g. fixed relative to console 200). A linkage, wire 2523, can be fixedly attached to cart 2521 and loop around a fixed pulley, pulley 2525 as shown, such that when ends 2524*a,b* are pulled and/or released (e.g. by a control assembly as described herein), cart 2521 retracts and/or advances, respectively.

Drive assembly 2530 includes a translating component, rack 2532, including an attachment mechanism, mount 2531, that attaches (e.g. removably attaches) to a plunger of a syringe (not shown), such that as rack 2532 advances and/or retracts, the plunger advances and/or retracts. Rack 2532 can be slidingly fixed relative to other fixed components of drive assembly 2530 (e.g. slidingly fixed to console 200), such that rack 2532 is free to translate left and right as shown on the page. A linkage, belt 2523, can be looped around a fixed pulley assembly, pulley 2535. Pulley 2535 can comprise one or more circumferential projections, teeth 2536, such that when pulley 2535 rotates, teeth 2356 engage one or more mating projections of rack 2532, teeth 2537. When teeth 2536 engage teeth 2537, and pulley 2635 is rotated, rack 2532 translates left or right. When ends 2534*a,b* of belt 2533 are pulled and/or released, (e.g. by a control assembly as described herein), pulley 2535 rotates, and rack 2532 retracts and/or advances, respectively. In some embodiments, belt 2533 comprises a toothed belt and/or a chain that engages pulley 2535.

Figure 24:
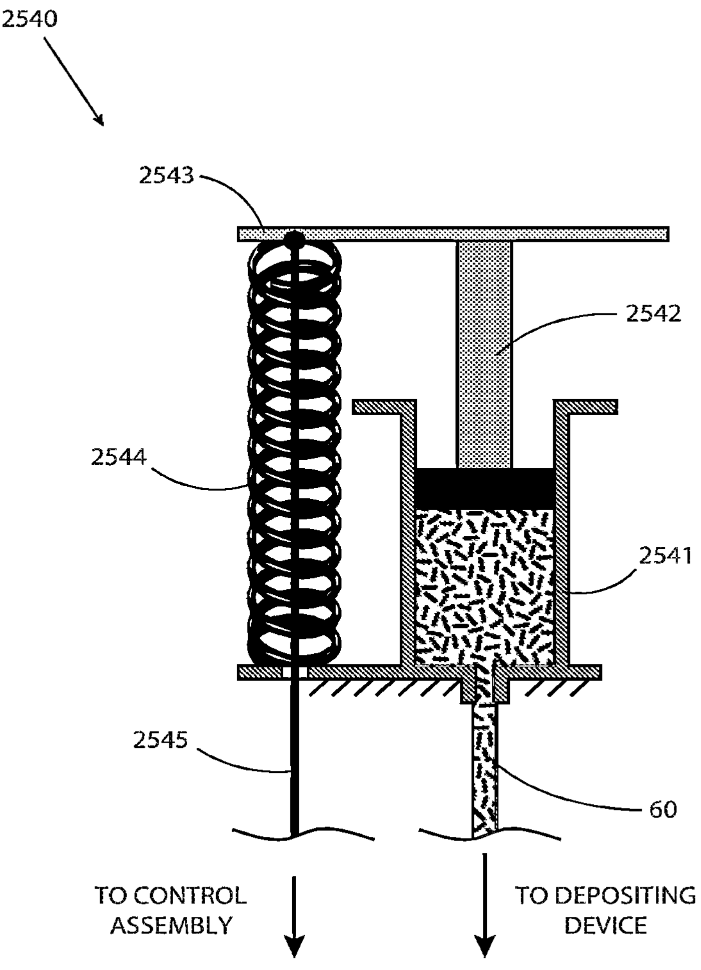
FIG. 24 illustrates a schematic view of a spring-loaded syringe drive, consistent with the present inventive concepts.

Referring now to FIG. 24, a schematic view of a spring-loaded syringe drive is illustrated, consistent with the present inventive concepts. Syringe drive assembly 2540 can comprises a spring-loaded drive assembly as shown. In some embodiments, a spring can bias the plunger of a syringe in a retracted position (as shown), or a spring can bias the plunger of a syringe in an advanced position. As shown in FIG. 24, syringe drive assembly 2540 can comprises a syringe 2541, and a plunger 2542 configured to deliver material 60 from and/or draw material 60 into syringe 2541. Plunger 2542 can include an attachment portion, control bar 2543. Syringe 2541 can be fixedly positioned relative to other fixed components of drive assembly 2520 (e.g. fixed relative to console 200). For example, syringe 2541 can comprise a standard (e.g. commercially available) syringe that is removably attached to a syringe holder that is fixedly positioned relative to console 200, and/or syringe 2541 can comprise an integral, fixed syringe (e.g. integral to console 200). Alternatively, plunger 2542 can be fixedly positioned relative to other fixed components of drive assembly 2520, and syringe 2541 can be configured to be translated (e.g. advanced and/or retracted) relative to fixed plunger 2542.

A biasing mechanism, spring 2544, can be positioned between a fixed location and control bar 2543, such as to apply a bias to control bar 2543 (e.g. biased toward a retracted position of plunger 2542, as shown). A linkage, cable 2545, can be fixedly attached to control bar 2543, and it can extend in a direction opposite the bias of spring 2544, such that a pulling force applied to cable 2545 acts against the bias of spring 2545 and causes the translation (e.g. advancement) of plunger 2542. In some embodiments, syringe drive assembly 2540 comprises a motor and bobbin, a linear drive, or other force applying assembly that applies a pulling force to cable 2545. Alternatively or additionally, a control assembly, not shown but described herein, can comprise a mechanism configured to enable the operator to apply a pulling force to cable 2545 to actuate plunger 2542. In some embodiments, spring 2544 comprises a compression spring configured to apply a pushing force on control bar 2543 to apply a bias (e.g. as shown). Alternatively, spring 2533 can comprise an extension spring configured to apply a pulling force on control bar 2543 to apply a bias. In some embodiments, spring 2543 comprises a compression spring with a fully expanded length less than the translation distance of plunger 2542, such as less than 20%, less than 10%, or less than 5% of the translation distance of plunger 2542, such that spring 2543 only applies a biasing force to control bar 2543 if plunger is advanced within 20%, 10%, or 5% (respectively) of the fully advanced position.

The above-described embodiments should be understood to serve only as illustrative examples; further embodiments are envisaged. Any feature described herein in relation to any one embodiment can be used alone, or in combination with other features described, and may also be used in combination with one or more features of any other of the embodiments, or any combination of any other of the embodiments. Furthermore, equivalents and modifications not described hereabove may also be employed without departing from the scope of the invention, which is defined in the accompanying claims.

What is claimed is:

1. A method of treating a medical condition of a patient, comprising:

advancing an access device through a mouth of the patient, the access device comprising an ultrasonically guided endoscope comprising a working channel sized to slidingly receive a depositing device, the depositing device comprising a depositing element; and performing at least one injection comprising:

advancing the depositing element through the working channel of the ultrasonically guided endoscope and through a wall of a gastrointestinal tract of the patient to a location proximate at least one deposit site in the patient; and delivering a treatment agent into the at least one deposit site via the depositing element, wherein the at least one deposit site is the intraparenchymal space of the pancreas of the patient, wherein the treatment agent comprises gene therapy material, and wherein the method treats a medical condition of the patient selected from the group consisting of: type one diabetes; type two diabetes; obesity; and combinations thereof.

2. The method according to claim 1, wherein the at least one deposit site comprises the body and tail of the pancreas.

3. The method according to claim 1, wherein the gene therapy material comprises adeno-associated virus-based gene therapy material.

4. The method according to claim 1, wherein the treatment agent is delivered at a flow rate of no more than 5 mL/min.

5. The method according to claim 1, wherein performing the at least one injection comprises performing two or more injections in which the depositing element is advanced two or more times.

6. The method according to claim 1, wherein the depositing element comprises one or more needles, wherein each needle comprises a distal segment, and wherein the distal segment comprises a maximum size of 25 gauge.

7. The method according to claim 6, wherein the distal segment comprises a maximum size of 27 gauge.

8. The method according to claim 6, wherein the distal segment comprises a length of at least 2 cm.

9. The method according to claim 1, wherein the at least one deposit site comprises a first deposit site and a second deposit site different than the first deposit site, and wherein the performing of the at least one injection comprises performing a first injection at the first deposit site and a second injection at the second deposit site.

10. The method according to claim 1, wherein the at least one deposit site comprises a non-cancerous portion of the pancreas.

11. The method according to claim 1, wherein the at least one deposit site comprises normal parenchymal tissue.

12. The method according to claim 1, wherein the treatment agent is delivered at a pressure of no more than 25 mmHg.

13. The method according to claim 1, wherein the depositing element comprises a surface modification configured to increase visibility under ultrasonic imaging.

* * * * *